US008314152B2

(12) United States Patent
Widder et al.

(10) Patent No.: US 8,314,152 B2
(45) Date of Patent: Nov. 20, 2012

(54) METHODS AND COMPOSITIONS FOR TREATING OPHTHALMIC CONDITIONS WITH RETINYL DERIVATIVES

(75) Inventors: Kenneth Widder, Rancho Santa Fe, CA (US); Jay Lichter, San Diego, CA (US); Nathan L. Mata, La Jolla, CA (US)

(73) Assignee: Acucela, Inc., Seattle, WA (US)

( * ) Notice: Subject to any disclaimer, the term of this patent is extended or adjusted under 35 U.S.C. 154(b) by 1885 days.

(21) Appl. No.: 11/150,641

(22) Filed: Jun. 10, 2005

(65) Prior Publication Data
US 2006/0167088 A1    Jul. 27, 2006

Related U.S. Application Data

(60) Provisional application No. 60/582,293, filed on Jun. 23, 2004, provisional application No. 60/629,695, filed on Nov. 19, 2004, provisional application No. 60/660,904, filed on Mar. 11, 2005, provisional application No. 60/672,405, filed on Apr. 18, 2005.

(51) Int. Cl.
*A01N 33/18* (2006.01)
*A01N 33/24* (2006.01)
*A61K 31/12* (2006.01)
(52) U.S. Cl. ...................................... 514/676
(58) Field of Classification Search ............... 514/676
See application file for complete search history.

(56) References Cited

U.S. PATENT DOCUMENTS

| 4,190,594 A | 2/1980 | Gander et al. |
| 4,323,581 A | 4/1982 | Gander |
| 4,665,098 A | 5/1987 | Gibbs et al. |
| 4,743,400 A | 5/1988 | Maryanoff |
| 4,874,795 A | 10/1989 | Yessair |
| 5,023,252 A | 6/1991 | Hseih |
| 5,314,909 A | 5/1994 | Dollerup |
| 5,399,757 A | 3/1995 | Maryanoff |
| 5,596,011 A | 1/1997 | Repine et al. |
| 5,776,915 A | 7/1998 | Peterson et al. |
| 5,814,612 A | 9/1998 | Buck et al. |
| 6,034,211 A | 3/2000 | Kelly |
| 6,051,692 A | 4/2000 | Bandman et al. |
| 6,075,032 A | 6/2000 | Campochiaro et al. |
| 6,482,802 B1 | 11/2002 | Hu et al. |

(Continued)

FOREIGN PATENT DOCUMENTS

DE          3610531 A1    10/1986

(Continued)

OTHER PUBLICATIONS

Cogan, U. et al., "Binding Affinities of Retinol and Related Compounds to Retinol Binding Proteins," Eur. J. Biochem. 65:71-78 (1976).

(Continued)

*Primary Examiner* — Benjamin Packard
(74) *Attorney, Agent, or Firm* — Wilson, Sonsini, Goodrich & Rosati

(57) ABSTRACT

Compounds that cause reversible night blindness may be used to treat ophthalmic conditions associated with the overproduction of waste products that accumulate during the course of the visual cycle. We describe methods and compositions using such compounds and their derivatives to treat, for example, the macular degenerations and dystrophies or to alleviate symptoms associated with such ophthalmic conditions. Such compounds and their derivatives may be used as single agent therapy or in combination with other agents or therapies.

7 Claims, 25 Drawing Sheets

U.S. PATENT DOCUMENTS

| | | |
|---|---|---|
| 6,503,242 B1 | 1/2003 | Ellsberry |
| 6,506,917 B1 | 1/2003 | Evans et al. |
| 6,599,891 B2 | 7/2003 | North et al. |
| 6,696,606 B2 | 2/2004 | Curley, Jr. et al. |
| 6,875,767 B2 | 4/2005 | Bilodeau et al. |
| 2002/0031539 A1 | 3/2002 | Plutzky et al. |
| 2002/0128291 A1 | 9/2002 | Campochiaro et al. |
| 2002/0143062 A1 | 10/2002 | Lopez-Berestein et al. |
| 2002/0183394 A1 | 12/2002 | Gupta et al. |
| 2003/0022831 A1 | 1/2003 | Rothbard et al. |
| 2003/0032078 A1 | 2/2003 | Travis |
| 2004/0014131 A1 | 1/2004 | Benson |
| 2004/0092435 A1 | 5/2004 | Peyman |
| 2004/0102650 A1 | 5/2004 | Curley, Jr. et al. |
| 2004/0177387 A1 | 9/2004 | Jayakrishna |
| 2006/0069078 A1 | 3/2006 | Rando |
| 2006/0094063 A1 | 5/2006 | Mata et al. |
| 2006/0135460 A1 | 6/2006 | Widder et al. |
| 2007/0015827 A1 | 1/2007 | Widder et al. |

FOREIGN PATENT DOCUMENTS

| | | |
|---|---|---|
| EP | 2277516 | 1/2011 |
| EP | 2289500 | 3/2011 |
| JP | 11-503998 | 6/1999 |
| WO | WO-91-01745 A | 2/1991 |
| WO | WO-98-27972 A3 | 7/1998 |
| WO | WO-99-08682 A1 | 2/1999 |
| WO | WO-01-19770 A2 | 3/2001 |
| WO | WO 02/067917 A1 | 9/2002 |
| WO | WO-02-096857 A1 | 12/2002 |
| WO | WO-01-38344 A2 | 5/2004 |
| WO | WO-01-38344 A3 | 5/2004 |
| WO | WO-2004-050101 A2 | 6/2004 |
| WO | WO-2004-050101 A3 | 6/2004 |
| WO | WO 2004/069203 A2 | 8/2004 |
| WO | WO 2004-084883 A1 | 10/2004 |
| WO | WO-2004-098506 A2 | 11/2004 |
| WO | WO-2004-098506 A3 | 11/2004 |
| WO | WO-2004-059564 A1 | 6/2005 |
| WO | WO-2005-059564 A | 6/2005 |
| WO | WO-2005-077176 A1 | 8/2005 |
| WO | WO-2005-079774 A2 | 9/2005 |
| WO | WO-2005-087210 A2 | 9/2005 |
| WO | WO-2007-019503 A2 | 9/2005 |
| WO | WO-2007-019503 A3 | 9/2005 |
| WO | WO-2006-002097 A2 | 1/2006 |
| WO | WO-2006-007314 A1 | 1/2006 |
| WO | WO-2006-012512 | 2/2006 |
| WO | WO-2006-033734 A2 | 3/2006 |
| WO | WO-2006-033734 A3 | 3/2006 |
| WO | WO-2006-052860 A2 | 5/2006 |
| WO | WO-2006-052860 A3 | 5/2006 |
| WO | WO-2006-063128 A | 6/2006 |

OTHER PUBLICATIONS

Gollapalli, D.R. et al. "RPE65 Operates in the Vertebrate Visual Cycle by Stereospecifically Binding All-*trans*-Retinyl Esters," (Correction) Biochem. 43:7226 (2004).

Gollapalli, D.R. et al., "RPE65 Operates in the Vertebrate Visual Cycle by Stereospecifically Binding All-*trans*-Retinyl Esters," Biochem. 42:11824-11830 (2003).

Lakowicz, J.R., in *Principles of Fluorescence Spectroscopy*, 2$^{nd}$ ed. Kluwer, Academic/Plenum, New York (1999) pp. 53-55.

Noy, N. "Retinoid-binding proteins: mediators of retinoid action," Biochem. J. 348:481-495 (2000).

Sani, B.P. et al., "N-(4-hydroxyphenyl)retinamide: interactions with retinoid-binding proteins/receptors," Carcinogenesis 16(10):2531-2534 (1995).

U.S. Appl. No. 60/578,324, filed Jun. 9, 2004, Robert R. Rando.
U.S. Appl. No. 60/567,604, filed Mar. 3, 2004, Robert R. Rando.
U.S. Appl. No. 60/545,456, filed Feb. 17, 2004, Robert R. Rando.

Jones, P.G. et al., "Specific binding of fluorescein labelled serum retinol-binding protein to its cell surface receptor in isolated, purified bovine pigment epithelial cells," Exp. Eye Res. 30(5):489-499 (1980).

Nilsson, S.F. et al., "Studies on thyroid hormone binding proteins Part 2. Binding of thyroid hormones retinol binding protein and fluorescent probes to prealbumin and effects of thyroxine on prealbumin subunit self association," J. Biol. Chem. 250(21):8554-8563 (1975).

EP 05817231 Supplemental Search Report dated Dec. 16, 2008.

Caruso, R. et al., "Effects of Fenretinide (4-HPR) on Dark Adaptation," Arch. Ophthalmol. 116:759-763 (1998).

Gollapalli, D.R. and Rando, R.R., "The specific binding of retinoic acid to RPE65 and approaches to the treatment of macular degeneration," PNAS 101(27):10030-10035 (2004).

Katz, M.L. et al., "Relationship between dietary retinol and lipofuscin in the retinal pigment epithelium," Mechanisms of Ageing and Development 35:291-305 (1986).

Law, W.C. and Rando, R.R., "The Molecular Basis of Retinoic Acid Induced Night Blindness," Biochem. Biophys. Res. Comm. 161(2):825-829 (1989).

Lewis, K.C. et al., "Effects of Chronic Administration of N-(4-hydroxyphenyl)retinamide (4-HPR) in Rats on Vitamin A Metabolism in the Eye," Eur. J. Cancer 32A(10):1803-1808 (1996).

Lewis, K.C. et al., "Effects of N-(4-Hydroxyphenyl)retinamide Supplementation on Vitamin A Metabolism," Cancer Res. 54:4112-4117 (1994).

Malpeli, G. et al., "Retinoid binding to retinol-binding protein and the interference with the interaction with transthyretin," Biochimica et Biophysica Acta 1294:48-54 (1996).

Radu, R.A. et al., "Treatment with isotretinoin inhibits lipofuscin accumulation in a mouse model of recessive Stargardt's macular degeneration," PNAS 100(8):4742-4747 (2003).

Sparrow, J. R., "Therapy for macular degeneration: Insights from acne," PNAS 100(8):4353-4354 (2003).

Vogel, S. et al., "Retinol-Binding Protein-Deficient Mice: Biochemical Basis for Impaired Vision," Biochemistry 41:15360-15368 (2002).

Supplementary Search Report EP 05853359 dated Apr. 14, 2008.

R. Allikmets, et al., "Mutation of the Stargardt Disease Gene (ABCR) in Age-Related Macular Degeneration" *Science*, vol. 277,( Sep. 19, 1997).

R. Allikmets, "Simple and Complex ABCR: Genetic Predisposition to Retinal Disease", *Am. J. Hum. Genet.* 67:793-799 Columbia University, New York (2000).

W. Baehr, S.M. Wu et al., "The retinoid cycle and retina disease," *Vision Research* 43(2003) 2957-2958.

L. Baglietto, MSc, et al., "Ocular Effects of Fenretinide, a Vitamin A Analog, in a Chemoprevention Trial of Bladder Cancer", *Cancer Detection and Prevention*, 24(4): 369-375 (2000).

D.R. Bergsma, B.N. Wiggert, et al., "Vitamin A Receptors in Normal and Dystrophic Human Retina", *Nature* vol. 265, (Jan. 6, 1977).

P.S. Bernstein, R.R. Rando, "In vivo isomerization of all-trans- to 11-cis-retinoids in the eye occurs at the alcohol oxidation state," *Biochemistry*, Oct. 21, 1986; 25(21):6473-6478.

J.W. Berkow, M.D. "Subretinal Neovascularization in Senile Macular Degeneration" *American Journal of Ophthamology* 97:143-147, (1984).

A. Bindewald, M.D.,et al. "Visualization of Retinal Pigment Epithelial Cells in Vivo Using Digital High-Resolution Confocal Scanning Laser Ophthalmology" *American Journal of Ophthalmology*, (Mar. 2004, pp. 556-558).

D. Bok, "New insights and new approaches toward the study of age-related macular degeneration," *PNAS*, Nov. 12, 2002, vol. 99, No. 23, 14619-14621.

R. C. Caruso, M.D., et al., "Effects of Fenretinide (4-HPR) on Dark Adoption" *Arch Ophthalmology*/vol. 116, (Jun. 1998), pp. 739, 760-763.

S. Chen, et al. "Differentation of Human Retinal Pigment Epithelial Cells into Neuronal Phenotype by N-(4-Hydroxyphenyl) Retinamide", *J. Neurochem.* (2003) 84, 972-981.

J. W. Crabb,et al. "Drusen Proteome Analysis: An Approach to the Etiology of Age-Related Macular Degeneration" 14682-14687, *PNAS*, (Nov. 12, 2002), vol. 99 No. 23.

F.P.M. Cremers,et al., "Autosomal Recessive Retinitis Pigmentosa and Cone-Rod Dystrophy Caused by Splice Site Mutations in the Stargardt's Disease Gene ABCR" *Human Molecular Genetics*, (1998), vol. 7, No. 3, pp. 355-362.

R.K. Crouch and P. Goletz, "Fenretinide Does Not Block Visual Pigment Formation in the Rat", *J. of Ocular Pharmacology*, vol. 4, No. 3, 1988, pp. 253-256.

L. Cy, C.L. Zimmerman, et al., "Solubilization of retinoids by bile salt/phospholipid aggregates," *Pharm. Res.* Jun. 1996; 13(6): 907-913.

A. Decensi, R. Torrisi, et al. "Effect of the Synthetic Retinoid Fenretinide on Dark Adaption and the Occular Surface" *Journal of the National Cancer Institute*, vol. 86, No. 2, (Jan. 19, 1994), pp. 105-110.

A. Decensi, V. Fontana, et al. "Long-Term Effects of Fenretinide on Retinal Function" *Eur F Cancer*, vol. 33, No. 1, pp. 80-84, (1997).

S.E. Dew, et al., "Effects of Pharmacological Retinoids on Several Vitamin A—Metabolizing Enzymes," *Cancer Research* 53, 2965-2969 (Jul. 1, 1993).

F.L. Ferris, III, M.D. and R.D. Sperduto, M.D., "Standardized Illumination for Visual Activity Testing in Clinical Research, "*American J. of Opthalmology* 94:97-98 (1982).

S.C. Finneman, et al., The Lipfuscin Component A2E Selectively Inhibits Phagolysosomal Degradation of Photoreceptor Phospholipid by the Retinal Pigment Epithelium, 3842-3847 *PNAS* Mar. 19, 2002 vol. 99, No. 6.

F. Formelli, et al., "Five-Year Administration of Fenretinide: Pharmacokinetics and Effects on Plasma Retinol Concentrations,"*J. of Clinial Oncology*, vol. 11 No. 10 (Oct. 1993) pp. 2036-2042.

F. Formelli, et al., "Plasma Retinol Level Reduction by Synthetic Retinoid Fenretinide: A One Year Follow-Up Study of Breast Cancer Patients," *Canceer Research* 49, 6149-6152, Nov. 1, 1999.

F.T. Franfelder, M.D., et al., "Ocular Side Effects Possibly Associated with Isotretinoin Usage," *American J. of Ophthalmology*, Sep. 2001, pp. 299-305.

L. Garcia-Marcos and A. Schuster, "New perspectives for asthma treatment: Anti-leukotriene drugs," *Pediatr. Allergy Immunol.* 1999:10:77-88.

D.R. Gollapalli and R.R. Rando, "The Specific Binding of Retinoic Acid to RPE65 and Approaches tot he Treatment of Macular Degeneration," 10030-10035, *PNAS*, Jul. 6, 2004, vol. 101, No. 27.

M.H. Green and J.B. Green, "Model-Based Compartmental Analysis of Retinol Kinetics in Organs of Rats at Different Levels of Vitamin A Status," *Networks: New Trends in Research and Clinical Applications*, Livera, M.A., Packer, L., eds., Marcel-Dekker, Inc. New York 1993, pp. 185-204.

E.G. Gross, M.D. and M.A. Helfgott M.D., "Retinoids and the Eye," *Dermatologic Clinics*, vol. 10 No. 3 Jul. 1992, pp. 521-531.

M. Hammer, et al., "Spektrale Differenzieuring in Eigenfluoreszenzbildern des Augenhintergrunds von Patienten mit altersabhangiger Mankuladegerations," *Online* publiziert: (Apr. 7, 2004) Germany (with English abstract).

T. Hultin, et al., N-(4-Hydroxyphenyl)-all trans-Retinamide Pharmacokinetics in Female Rats and Mice, *Drug, Metabolism and Disposition* vol. 14 No. 6 1986 pp. 714-717.

L.J. Ignarro, et al., "Endothelium-derived Relaxing Factor Produced and Released from Artery and Vein is Nitric Oxide,"*Proc. Natl. Acad. Sci. USA* vol. 84, pp. 9265-9269 (Dec. 1987) Medical Sciences.

M.L. Kaiser-Kupper, M.D., et al., Abnormal Retinal Function Associated with Fenretinide, a Synthetic Retinoid, *Arch Ophthalmol.*, vol. 104, Jan. 1986, pp. 69-70.

M.L. Katz, C.M. Drea and G.D Robinson, Jr., "Dietary Vitamins A and E Influence Retinyl Ester Composition and Content of the Retinal Pigment Epithelium" *Biochimica et Biophysica Acta* 924 (1987) 432-441.

M.L. Katz, G.E. Eldred and W.G. Robinson, Jr., "Lipofuscin Autofluorescence: Evidence for Vitamin A Involvement in the Retina" *Mechanisms of Ageing and Development*, 39(1987) 81-90 Elsevier Scientific Publishers Ireland, Ltd.

M.L. Katz, C.M. Drea and W.G. Robinson, Jr., "Relationship Between Dietary Retinol and Lipofuscin in the Retinal Pigment Epithelium" *Mechanisms of Ageing and Development* 35 (1986) 291-305 Elsevier Scientific Publishers Ireland, Ltd.

W. Kedzierski, M.Lloyd, et al., "Generation and Analysis of Transgenic Mice Expressing P216L-Substituted Rds/Peripherin in Rod Photoreceptors" *Investigative Opthalmology & Visual Science*, (Feb. 1997), Vo. 38, No. 2, pp. 498-509.

B. Jeroen Klevering, M.D., A. Maugeri, Ph.D., et al., "Three Families Displaying the Combination of Stargardt's Disease with Cone-Rod Dystophy or Retinitis Pigmentosa", (2004) J. Ophtha. 2003, *By the American Academy of Opthamology Published by Elsevier, Inc.*

M.Kliffen, T.L. Van Der Schaft, et al., "Morphologic Changes in Age-Related Maculopathy", *Microscopy Research and Technique* 36:106-122 (1997).

W. C. Law and R.R. Rando, "The Molecular Basic of Retinoid Acid Induced Night Blindness" *Biochemical and Biophysical Research Communications*, p. 825-829, vol. 161, No. 2, (Jun. 15, 1989).

R.A. Lewis, N.F. Shoyer, et al., "Genotype/Phenotype Analysis of a Photoreceptor-Specific ATP-Binding Cassette Transporter Gene, ABCR, in Stargardt Disease", *Am. J. Hum. Genet.* 64:422-434, (1999).

K.C. Lewis, L.A. Zech and J.M. Phang, "Effects of Chronic Administration of N-(4-hyroxypheny) Retinamide (4-HRP) in Rats on Vitamin A Metabolism in the Eye" *Eupoean Journal of Cancer*, vol. 32A, No. pp. 1803-1808, (1996) (Printed in Great Britian).

K.C. Lewis and J.F. Hochadel, "Retinoid Metabolism in the Prostate: Effects of Administration of the Synthetic Retinoid N-(4-Hydroxyphenyl) retinamide," *Cancer Research* 59., 5947-5955, Dec. 1, 1999.

C.Yuan Li, C.L. Zimmerman and T.S. Wiedmann, "Solubilization of Retinoids by Bile Salt/Phospholipid Aggregates" *Pharmaceutical Research*, vol. 13, No. 6, (1996).

L. Mariani, F. Formelli, et al., "Chemoprevention of Breast Cancer with Fenretinide (4-HPR): Study of Long-Term Visual and Ophthalmologic Tolerability", *Istituto Nazionale per lo Studi e la Cura dei Tumori, Milan: Istituto Nazionale Neurologico Carol Besta Milan; and European Institute of Oncology*, Milan, Italy; Tumori, 82:444-449, (1996).

G. McGwin, Jr., C. Owsley, et al., "The Association Between Statin Use and Age Related Maculopathy", *Br J Ophthalmol* (2003); 87: 1121-1125.

M.R. Modiano, W.S. Dalton, et al., "Ocular Toxic Effects of Fenretinide," *Brief Communications*, vol. 82, No. 12, Jun. 20, 1990, p. 1063.

R.C. Moon, H.J. Thompson, et al., "n(4-Hydroxyphenyl) Retinimide, a New Retinoid for Preventon of Breast Cancer in the Rat", *Cancer Research* 39, 1339-1346, (Apr. 1979).

R.M. J. Palmer, A.G. Ferrige & S. Moncada, "Nitric Oxide Release Accounts for the Biological Activity of Endothelium-derived Relaxing Factor", *Nature* vol. 327 Jun. 11, 1987, pp. 524-526.

R.A. Radu, N.L. Mata, et al. , "Treatment with Isotretinoin Inhibits Lipofuscin Accumulation in a Mouse Model of Recessive Stargardt's Macular Degeneration", 4742-4747, *PNAS*, (Apr. 15, 2003), vol. 100, No. 8.

R.A. Radu, N.L. Mata, et al., "Light Exposure Stimulates Formation of A2E Oxinranes in a Mouse Model of Stargardt's Macular Degeneration", 5928-5933, *PNAS*, (Apr. 20, 2004), vol. 101, No. 16.

R.S. Rando, "The Biochemistry of the Visual Cycle", *Chem. Rev.* 2001, 101, 1881-1896.

R.R. Rando, "Small Molecule Approaches to the Management of Macular Degeneration by Short-Circuiting the Visual Cycle," http://www.techtransfer.harvard.edu/cgi-gin/TALSearch.cgi?full_report=1&case-2252, May 31, 2005.

H. Shaban and C. Richter, "A2E and Blue Light in the Retina: The Paradigm of Age-Related Macular Degeneration", *Biol. Chem.*, vol. 383, pp. 537-545, (Mar./Apr. 2002).

H. Shaban, C. Borras, et al., "Phosphatidylglycerol Potently Protects Human Retinal Pigment Epithelial Cells Against Apoptosis Induced by A2E, a Compound Suspected to Cause Age-Related Macula Degeneration"*Exp. Eye Res.* (2002) 75, 99-108.

P.A. Sieving, P. Chaudhry, et al., "Inhibition of the Visual Cycle in Vivo by 13-cis Retinoic Acid Protects from Light Damage and Provides a Mechanism for Night Blindness in Isotretinoin Therapy", *PNAS*, (Feb. 13, 2001), vol. 98 No. 4, 1835-1840.

J.R. Sparrow, H.R. Vollmer-Snarr, et al., "A2E-Epoxides Damage DNA in Retinal Pigment Epithelial Cells" *J. of Biological Chemistry*,vol. 278, No. 20, Issue of May 16, pp. 18207-18213, 2003.

R.L. Steinmetz, R. Haimovici, et al., "*Symptomatic Abnormalities of Dark Adaption in Patients with Age-Related Bruch's Membrane Change*", British Journal of Ophthalmology 1993:77:549-554.

J.L Wijnen, H. Van Der Klift, et al. "Allelic Variation in ABCR associated with Stargardt Disease but not Age-Related Macular Degeneration", *Nature Genetics* vol. 20, (Dec. 1998).

R. Torrisi, S. Parodi, et al., "Factors Affecting Plasma Retinol Decline during Long-Term Administration of the Synthetic Retinoid Fenretinide in Breast Cancer Patients", *Cancer, Epidemiology, Biomarkers & Prevention*, vol. 3, 507-510, (Sep. 1994).

J.L. Ubels, M.H. Dennis, et al., "Biological Activity of N-(4-hydroxyphenyl) Retinamide-O-Glucuronide in Corneal and Conjunctival Cells of Rabbits and Humans", *Current Eye Research*, received on May 3, 1995, accepted Aug. 14, 1995, Oxford University Press.

S. Jong Um, Y. Kwon, et al., "*Synthesis and Biological Activity of Novel Retinamide and Retinoate Derivatives*" Chem. Pharm. Bull. 52(5) 501-506 (2004).

G.B. Villeneuve and T.H. Chan, "A Rapid, Mild and Acid-Free Procedure for the Preparation of Acyl Chlorides including Formyl Chloride", *Tetrahedron Letters*, vol.38, No. 37, pp. 6489-6942, (1997).

J. Weng, N.L. Mata, et al., "Insights into the Function of Rim Protein in Photoreceptors and Etiology of Stargardt's Disease from the Phenotype in ABCR Knockout Mice", *Cell*, vol. 98, 13-23, (Jul. 9, 1999).

M. Whittaker, C.D. Floyd, et al., "Design and Therapeutic Application of Matrix Metalloproteinase Inhibitors", *Chem. Rev.* (1999)99, 2735-2776.

Areds Report No. 8, "A Randomized, Placebo-Controlled, Clinical Trial of High-Dose Supplementation with Vitamins C and E, Beta Carotene, and Zinc for Age-Related Macular Degeneration and Vision Loss", *Arch Ophthalmol*, vol. 119, (Oct. 2001)—Age Related Eye Disease Study Research Group.

B. Wiggert, et al., "Current Research, Biochemistry Section," http://www.nei.nih.gov/Intramural/biochem.htm, Jun. 14, 2004.

A.V. Cideciyan, et al., "Mutations in ABCA4 result in accumulation of lipofuscin before slowing of the retinoid cycle: a reappraisal of the human disease sequence," *Hum.Mol. Genet.* 13(5) (2004) pp. 525-534.

R.F. Spaide, "Fundus autofluorescence and age-related macular degeneration," *Ophthalmology* 110 (2003) pp. 392-399.

F.G. Holz et al., "Flundus autofluorescence and development of geographic atrophy in age-related macular degeneration," *Investigative Ophthalmology and Visual Science* 42 (2001) pp. 1051-1056.

G. Malpeli, et al., "Retinoid binding to retinol-binding protein and the interference with the interaction with transthyretin," *Biochim Biophys Acta*, May 2, 1996; 1294(1):48-54.

S. Vogel, et al., "Retinol-binding protein-deficient mice: biochemical basis for impaired vision," *Biochemistry*, Dec. 24, 2002;41(51):15360-8.

G. Karan, et al., "Lipfusin accumulation, abnormal electrophysiology, and photoreceptor degeneration in mutant ELOVL4 transgenic mice: a model for macular degeneration," *Proc. Natl. Acad. Sci. USA*, Mar. 15, 2005; 102(11)::4164-9.

D. Besch, et al., "Inherited multifocal RPE-diseases: mechanisms defects for local dysfuntion in global retinioid cycle gene defects," *Vision Res.* Dec. 2003;43(28):3095-108.

M.L. Katz, et al., "RPE65 gene mutation prevents development of autofluorescence in retinal pigment epithelial phagosomes," *Mech. Ageing Dev.* Apr. 2005;126(4);513-21.

Supplemental EP Search Report for EP06800032.2 dated Aug. 12, 2008.

Chen, S. et al., "Differentiation of cultured human retinal pigment epithelial (RPE) cells into neuronal phenotypes induced by fenretinide," Annual Meeting of the Association for Research in Vision and Ophthalmology, 2002, Abstract No. 4556.

Mata, N.L. et al., Effects of N-(4-hydroxyphenyl) retinamide on vitamin A homeostasis and A2E biosynthesis in abcr null mutant mice, Annual Meeting of the Association for Research in Vision and Ophthalmology, May 1, 2005, 46, 1744 (Abstract only).

Nedelkov, D. and Nelson, R., "Delineation of in vivo assembled multiprotein complexes via biomolecular interaction analysis mass spectrometry," Proteomics 2001, 1, 1441-1446.

Noy, N. et al., "Interactions of Retinol with Binding Proteins: Studies with Retinol-Binding Protein and with Transthyretin," Biochemistry 1992, 31, 11118-11124.

Sharara, N.A. et al., "The potential clinical utility of fenretinide in the treatment of retinoblastoma; in vitro study," Annual Meeting of the Association for Research in Vision and Ophthalmology, 2003, Abstract No. 1581.

Zheng, W. et al., "Transthyretin, Thyroxine, and Retinol-Binding Protein in Human Cerebrospinal Fluid: Effect of Lead Exposure," Toxicological Sciences 61, 107-114 (2001).

EP 10181656.9 Search Report mailed Dec. 29, 2010.
EP 10181763.3 Search Report mailed Jan. 3, 2011.
U.S. Appl. No. 11/296,909 Office Action mailed Jan. 21, 2010.
U.S. Appl. No. 11/296,909 Office Action mailed Jul. 2, 2009.
U.S. Appl. No. 11/267,395 Office Action mailed Nov. 21, 2007.
U.S. Appl. No. 11/267,395 Office Action mailed Mar. 26, 2008.
U.S. Appl. No. 12/189,695 Office Action mailed Dec. 27, 2010.
U.S. Appl. No. 11/484,228 Office Action mailed Nov. 12, 2010.
U.S. Appl. No. 11/484,228 Office Action mailed May 26, 2010.
Lovat, "GADD153 and 12-Lipoxygenase Mediate Fenretinide-induced Apoptosis of Neuroblastoma," Can. Res. 62:5158-5167 (2002).

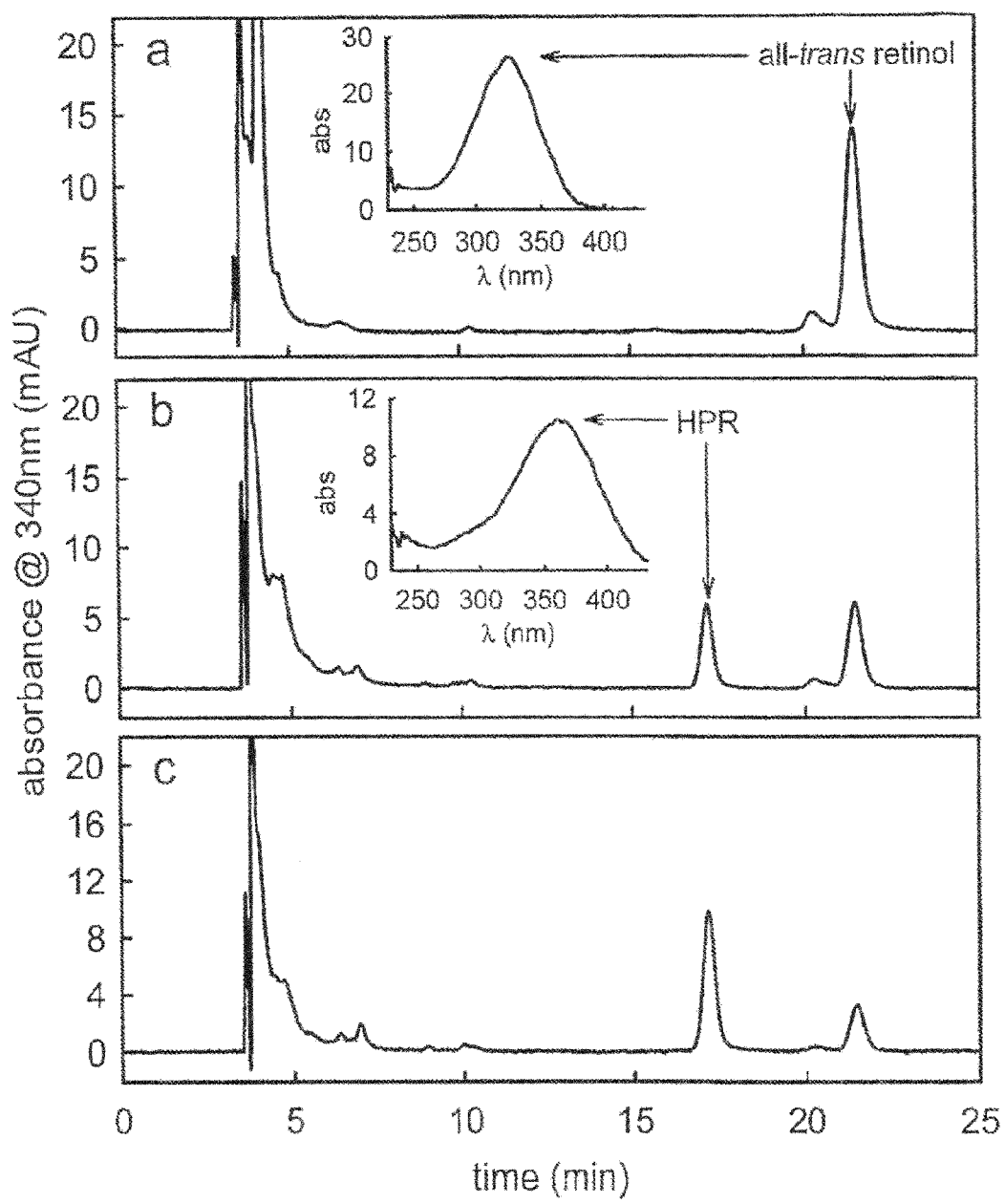
Figure 1 a - c

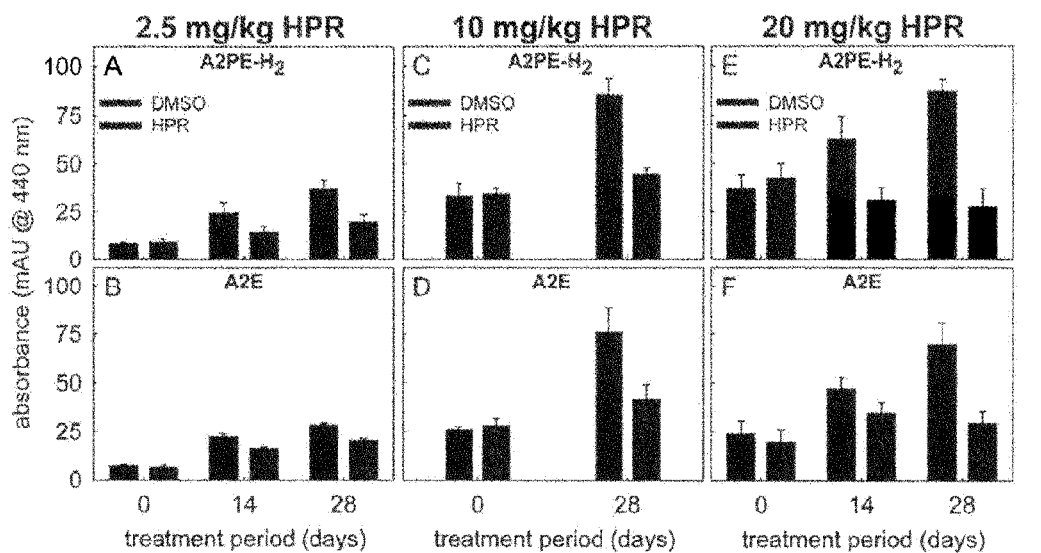
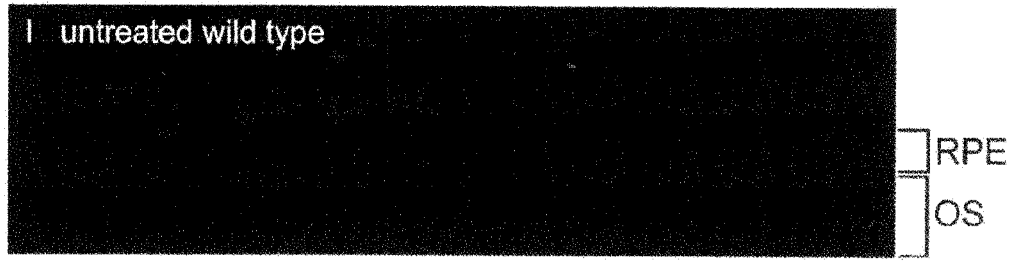
Figure 18

METHODS AND COMPOSITIONS FOR TREATING OPHTHALMIC CONDITIONS WITH RETINYL DERIVATIVES

CROSS-REFERENCE TO RELATED APPLICATIONS

This Application claims the benefit of U.S. Provisional Application Ser. No. 60/582,293, filed on Jun. 23, 2004, U.S. Provisional Application Ser. No. 60/629,695, filed on Nov. 19, 2004, U.S. Provisional Application Ser. No. 60/660,904, filed on Mar. 11, 2005, U.S. Provisional Application Ser. No. 60/672,405, filed on Apr. 18, 2005, the disclosures of all of which are hereby incorporated by reference in their entirety.

FIELD OF THE INVENTION

The methods and compositions described herein are directed to the treatment of ophthalmic conditions.

BACKGROUND OF THE INVENTION

The visual cycle or retinoid cycle is a series of light-driven and enzyme catalyzed reactions in which the active visual chromophore rhodopsin is converted to an all-trans-isomer that is then subsequently regenerated. Part of the cycle occurs within the outer segment of the rods and part of the cycle occurs in the retinal pigment epithelium (RPE). Components of this cycle include various dehydrogenases and isomerases, as well as proteins for transporting intermediates between the photoreceptors and the RPE.

Other proteins associated with the visual cycle are responsible for transporting, removing and/or disposing of compounds and toxic products that accumulate from excess production of visual cycle retinoids, such as all-trans-retinal (atRAL). For example, N-retinylidene-N-retinylethanolamine (A2E) arises from the condensation of all-trans-retinal with phosphatidylethanolamine. Although certain levels of this orange-emitting fluorophore are tolerated by the photoreceptors and the RPE, excessive quantities can lead to adverse effects, including the production of lipofuscin, and potentially drusen under the macula. See, e.g., Finnemann, S. C., *Proc. Natl. Acad. Sci.*, 99:3842-47 (2002). In addition, A2E can be cytotoxic to the RPE, which can lead to retinal damage and destruction. Drusen are extracellular deposits that accumulate below the RPE and are risk factors for developing age-related macular degeneration. See, e.g., Crabb, J. W., et al., *Proc. Natl. Acad. Sci.*, 99:14682-87 (2002). Thus, removal and disposal of toxic products that arise from side reactions in the visual cycle are important because several lines of evidence indicate that the over-accumulation of toxic products is partially responsible for the symptoms associated with the macular degenerations and retinal dystrophies.

There are two general categories of age-related macular degeneration: the wet and dry forms. Dry macular degeneration, which accounts for about 90 percent of all cases, is also known as atrophic, nonexudative, or drusenoid macular degeneration. With dry macular degeneration, drusen typically accumulate beneath the RPE tissue in the retina. Vision loss can then occur when drusen interfere with the function of photoreceptors in the macula. This form of macular degeneration results in the gradual loss of vision over many years.

Wet macular degeneration, which accounts for about 10 percent of cases, is also known as choroidal neovascularization, subretinal neovascularization, exudative, or disciform degeneration. In wet macular degeneration, abnormal blood vessel growth can form beneath the macula; these vessels can leak blood and fluid into the macula and damage photoreceptor cells. Studies have shown that the dry form of macular degeneration can lead to the wet form of macular degeneration. The wet form of macular degeneration can progress rapidly and cause severe damage to central vision.

Stargardt Disease, also known as Stargardt Macular Dystrophy or Fundus Flavimaculatus, is the most frequently encountered juvenile onset form of macular dystrophy. Research indicates that this condition is transmitted as an autosomal recessive trait in the ABCA4 gene (also known as the ABCR gene). This gene is a member of the ABC Super Family of genes that encode for transmembrane proteins involved in the energy dependent transport of a wide spectrum of substances across membranes.

Symptoms of Stargardt Disease include a decrease in central vision and difficulty with dark adaptation, problems that generally worsen with age so that many persons afflicted with Stargardt Disease experience visual loss of 20/100 to 20/400. Persons with Stargardt Disease are generally encouraged to avoid bright light because of the potential over-production of all-trans-retinal.

Methods for diagnosing Stargardt Disease include the observation of an atrophic or "beaten-bronze" appearance of deterioration in the macula, and the presence of numerous yellowish-white spots that occur within the retina surrounding the atrophic-appearing central macular lesion. Other diagnostic tests include the use of an electroretinogram, electrooculogram, and dark adaptation testing. In addition, a fluorescein angiogram can be used to confirm the diagnosis. In this latter test, observation of a "dark" or "silent" choroid appears associated with the accumulation of lipofuscin in the retinal pigment epithelium of the patient, one of the early symptoms of macular degeneration.

Currently, treatment options for the macular degenerations and macular dystrophies are limited. Some patients with dry form AMD have responded to high doses of vitamins and minerals. In addition, a few studies have indicated that laser photocoagulation of drusen prevents or delays the development of drusen that can lead to the more severe symptoms of dry form AMD. Finally, certain studies have shown that extracorporeal rheopheresis benefits patients with dry form AMD.

However, successes have been limited and there continues to be a strong desire for new methods and treatments to manage and limit vision loss associated with the macular degenerations and dystrophies.

SUMMARY OF THE INVENTION

Presented herein are methods, compostions and formulations for (a) treating ophthalmic conditions, and (b) controlling symptoms that presage (e.g., risk factors) or are associated with such ophthalmic conditions. In one aspect, such methods and formulations comprise the use of retinyl derivatives. In other aspects the ophthalmic conditions are macular degenerations, macular dystrophies and retinal dystrophies. In other aspects, the methods and formulations are used to protect eyes of a mammal from light; in other aspects the methods and formulations are used to limit the formation of all-trans-retinal, N-retinylidene-N-retinylethanolamine, N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, N-retinylidene-phosphatidylethanolamine, lipofuscin, geographic atrophy (of which scotoma is one non-limiting example), photoreceptor degeneration and/or drusen in the eye of a mammal. In other aspects, such methods and formulations comprise the use of agents that can impair night vision. In other aspects, such methods and formulations comprise the use of agents to treat ophthalmic conditions by (a) lowering the levels of serum retinol in the body of a patient, (b) modulating the activity of enzymes or proteins in the eye of a patient wherein such enzymes or proteins are involved in the visual cycle, such as, by way of example, lecithin-retinol acyltransferase and/or cellular retinaldehyde binding protein, or (c) combining the effects of (a) and (b). In yet other aspects, the methods and formulations are used in combination with other treatment modalities.

In one aspect are methods for reducing the formation of all-trans-retinal in an eye of a mammal comprising administering to the mammal at least once an effective amount of a first compound having the structure of Formula (I):

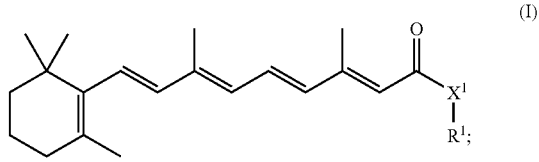

(I)

wherein $X_1$ is selected from the group consisting of $NR^2$, O, S, $CHR^2$; $R^1$ is $(CHR^2)_x$-$L^1$-$R^3$, wherein x is 0, 1, 2, or 3; $L^1$ is a single bond or —C(O)—; $R^2$ is a moiety selected from the group consisting of H, $(C_1$-$C_4)$alkyl, F, $(C_1$-$C_4)$fluoroalkyl, $(C_1$-$C_4)$alkoxy, —C(O)OH, —C(O)—$NH_2$, —$(C_1$-$C_4)$alkylamine, —C(O)—$(C_1$-$C_4)$alkyl, —C(O)—$(C_1$-$C_4)$fluoroalkyl, —C(O)—$(C_1$-$C_4)$alkylamine, and —C(O)—$(C_1$-$C_4)$alkoxy; and $R^3$ is H or a moiety, optionally substituted with 1-3 independently selected substituents, selected from the group consisting of $(C_2$-$C_7)$alkenyl, $(C_2$-$C_7)$alkynyl, aryl, $(C_3$-$C_7)$cycloalkyl, $(C_5$-$C_7)$cycloalkenyl, and a heterocycle, provided that $R^3$ is not H when both x is 0 and $L^1$ is a single bond; or an active metabolite, or a pharmaceutically acceptable prodrug or solvate thereof.

In another aspect are methods for reducing the formation of N-retinylidene-N-retinylethanolamine, N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine, in an eye of a mammal comprising administering to the mammal at least once an effective amount of a first compound having the structure of Formula (I).

In another aspect are methods for reducing the formation of lipofuscin in an eye of a mammal comprising administering to the mammal an effective amount of a first compound having the structure of Formula (I).

In another aspect are methods for reducing the formation of drusen in an eye of a mammal comprising administering to the mammal an effective amount of a first compound having the structure of Formula (I).

In another aspect are methods for modulating lecithin-retinol acyltransferase in an eye of a mammal comprising administering to the mammal an effective amount of a first compound having the structure of Formula (I).

In another aspect are methods for treating macular degeneration in an eye of a mammal comprising administering to the mammal an effective amount of a first compound having the structure of Formula (I). In a further embodiment of this aspect, the macular degeneration is juvenile macular degeneration, including Stargardt Disease. In a further embodiment of this aspect, (a) the macular degeneration is dry form age-related macular degeneration, or (b) the macular degeneration is cone-rod dystrophy. In a further embodiment of this aspect, the macular degeneration is the wet form of age-related macular degeneration. In a further embodiment of this aspect, the macular degeneration is choroidal neovascularization, subretinal neovascularization, exudative, or disciform degeneration.

In another aspect are methods for reducing the formation or limiting the spread of geographic atrophy (of which scotoma is one non-limiting example) and/or photoreceptor degeneration in an eye of a mammal comprising administering to the mammal an effective amount of a first compound having the structure of Formula (I).

In another aspect are methods for reducing the formation of abnormal blood vessel growth beneath the macula in an eye of a mammal comprising administering to the mammal an effective amount of a first compound having the structure of Formula (I).

In another aspect are methods for protecting the photoreceptors in any eye of a mammal comprising administering to the mammal an effective amount of a first compound having the structure of Formula (I).

In another aspect are methods for protecting an eye of a mammal from light comprising administering to the mammal an effective amount of a compound having the structure of Formula (I).

In another aspect are methods for disrupting the visual cycle in an eye of a mammal comprising administering to the mammal an effective amount of a compound having the structure of Formula (I).

In another aspect is the use of a compound of Formula (I) in the manufacture of a medicament for treating an ophthalmic disease or condition in an animal in which the activity of at least one visual cycle protein contributes to the pathology and/or symptoms of the disease or condition. In one embodiment of this aspect, the visual cycle protein is selected from the group consisting of lecithin-retinol acyltransferase and cellular retinaldehyde binding protein. In another or further embodiment of this aspect, the ophthalmic disease or condition is a retinopathy. In a further or alternative embodiment, the retinopathy is a macular degeneration. In a further or alternative embodiment, the symptom of the disease or condition is formation of all-trans-retinal, N-retinylidene-N-retinylethanolamine, N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, N-retinylidene-phosphatidylethanolamine, lipofuscin, photoreceptor degeneration, geographic atrophy (of which scotoma is one non-limiting example), choroidal neovascularization, and/or drusen in the eye of a mammal.

In any of the aforementioned aspects are further embodiments in which (a) $X^1$ is $NR^2$, wherein $R^2$ is H or $(C_1$-$C_4)$ alkyl; (b) wherein x is 0; (c) x is 1 and $L^1$ is —C(O)—; (d) $R^3$ is an optionally substituted aryl; (e) $R^3$ is an optionally substituted heteroaryl; (f) $X^1$ is NH and $R^3$ is an optionally substituted aryl, including yet further embodiments in which (i) the aryl group has one substituent, (ii) the aryl group has one substituent selected from the group consisting of halogen, OH, $O(C_1$-$C_4)$alkyl, $NH(C_1$-$C_4)$alkyl, $O(C_1$-$C_4)$fluoroalkyl, and $N[(C_1$-$C_4)$alkyl$]_2$, (iii) the aryl group has one substituent, which is OH, (v) the aryl is a phenyl, or (vi) the aryl is naphthyl; (g) the compound is

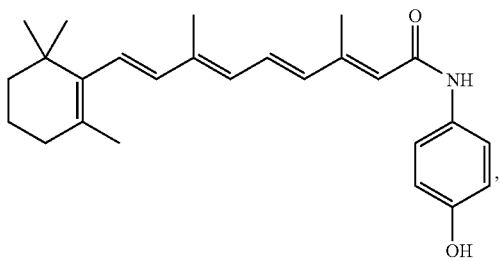

or an active metabolite, or a pharmaceutically acceptable prodrug or solvate thereof; (h) the compound is 4-hydroxyphenylretinamide, or a metabolite, or a pharmaceutically acceptable prodrug or solvate thereof; (i) the compound is 4-methoxyphenylretinamide, or (j) 4-oxo fenretinide, or a metabolite, or a pharmaceutically acceptable prodrug or solvate thereof.

In any of the aforementioned aspects are further embodiments in which (a) the effective amount of the compound is systemically administered to the mammal; (b) the effective amount of the compound is administered orally to the mammal; (c) the effective amount of the compound is intravenously administered to the mammal; (d) the effective amount of the compound is ophthalmically administered to the mammal; (e) the effective amount of the compound is administered by iontophoresis; or (f) the effective amount of the compound is administered by injection to the mammal.

In any of the aforementioned aspects are further embodiments in which the mammal is a human, including embodiments wherein (a) the human is a carrier of the mutant ABCA4 gene for Stargardt Disease or the human has a mutant ELOV4 gene for Stargardt Disease, or has a genetic variation in complement factor H associated with age-related macular degeneration, or (b) the human has an ophthalmic condition or trait selected from the group consisting of Stargardt Disease, recessive retinitis pigmentosa, geographic atrophy (of which scotoma is one non-limiting example), photoreceptor degeneration, dry-form AMD, recessive cone-rod dystrophy, exudative age-related macular degeneration, cone-rod dystrophy, and retinitis pigmentosa. In any of the aforementioned aspects are further embodiments in which the mammal is an animal model for retinal degeneration, examples of which are provided herein.

In any of the aforementioned aspects are further embodiments comprising multiple administrations of the effective amount of the compound, including further embodiments in which (i) the time between multiple administrations is at least one week; (ii) the time between multiple administrations is at least one day; and (iii) the compound is administered to the mammal on a daily basis; or (iv) the compound is administered to the mammal every 12 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned aspects are further embodiments comprising administering at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, 13-cis-retinoic acid (including derivatives of 13-cis-retinoic acid), 11-cis-retinoic acid (including derivatives of 11-cis-retinoic acid), 9-cis-retinoic acid (including derivatives of 9-cis-retinoic acid), and retinylamine derivatives. In further embodiments:

(a) the additional agent is an inducer of nitric oxide production, including embodiments in which the inducer of nitric oxide production is selected from the group consisting of citrulline, ornithine, nitrosated L-arginine, nitrosylated L-arginine, nitrosated N-hydroxy-L-arginine, nitrosylated N-hydroxy-L-arginine, nitrosated L-homoarginine and nitrosylated L-homoarginine;

(b) the additional agent is an anti-inflammatory agent, including embodiments in which the anti-inflammatory agent is selected from the group consisting of a nonsteroidal anti-inflammatory drug, a lipoxygenase inhibitor, prednisone, dexamethasone, and a cyclooxygenase inhibitor;

(c) the additional agent is at least one physiologically acceptable antioxidant, including embodiments in which the physiologically acceptable antioxidant is selected from the group consisting of Vitamin C, Vitamin E, beta-carotene, Coenzyme Q, and 4-hydroxy-2,2,6,6-tetramethylpiperadine-N-oxyl, or embodiments in which (i) the at least one physiologically acceptable antioxidant is administered with the compound having the structure of Formula (I), or (ii) at least two physiologically acceptable antioxidants are administered with the compound having the structure of Formula (I);

(d) the additional agent is at least one physiologically acceptable mineral, including embodiments in which the physiologically acceptable mineral is selected from the group consisting of a zinc (II) compound, a Cu(II) compound, and a selenium (II) compound, or embodiments further comprising administering to the mammal at least one physiologically acceptable antioxidant;

(e) the additional agent is a negatively charged phospholipid, including embodiments in which the negatively charged phospholipid is phosphatidylglycerol;

(f) the additional agent is a carotenoid, including embodiments in which the carotenoid is selected from the group consisting of lutein and zeaxanthin;

(g) the additional agent is a statin, including embodiments in which the statin is selected from the group consisting of rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium, and dihydrocompactin;

(h) the additional agent is an anti-angiogenic drug, including embodiments in which the the anti-angiogenic drug is Rhufab V2, Tryptophanyl-tRNA synthetase, an Anti-VEGF pegylated aptamer, Squalamine, anecortave acetate, Combretastatin A4 Prodrug, Macugen™, mifepristone, subtenon triamcinolone acetonide, intravitreal crystalline triamcinolone acetonide, AG3340, fluocinolone acetonide, and VEGF-Trap;

(i) the additional agent is a matrix metalloproteinase inhibitor, including embodiments in which the matrix metalloproteinase inhibitor is a tissue inhibitors of metalloproteinases, $\alpha_2$-macroglobulin, a tetracycline, a hydroxamate, a chelator, a synthetic MMP fragment, a succinyl mercaptopurine, a phosphonamidate, and a hydroxaminic acid;

(j) the additional agent is 13-cis-retinoic acid (including derivatives of 13-cis-retinoic acid), 11-cis-retinoic acid (including derivatives of 11-cis-retinoic acid), or 9-cis-retinoic acid (including derivatives of 9-cis-retinoic acid);
(k) the additional agent is a retinylamine derivative, including an all-trans-retinylamine derivative, a 13-cis-retinylamine derivative, a 11-cis-retinylamine derivative, or a 9-cis-retinylamine derivative;
(l) the additional agent is administered (i) prior to the administration of the compound having the structure of Formula (I), (ii) subsequent to the administration of the compound having the structure of Formula (I), (iii) simultaneously with the administration of the compound having the structure of Formula (I), or (iv) both prior and subsequent to the administration of the compound having the structure of Formula (I); or
(m) the additional agent and the compound having the structure of Formula (I),are administered in the same pharmaceutical composition.

In any of the aforementioned aspects are further embodiments comprising administering extracorporeal rheopheresis to the mammal.

In any of the aforementioned aspects are further embodiments comprising administering to the mammal a therapy selected from the group consisting of limited retinal translocation, photodynamic therapy, drusen lasering, macular hole surgery, macular translocation surgery, Phi-Motion, Proton Beam Therapy, Retinal Detachment and Vitreous Surgery, Scleral Buckle, Submacular Surgery, Transpupillary Thermotherapy, Photosystem I therapy, MicroCurrent Stimulation, anti-inflammatory agents, RNA interference, administration of eye medications such as phospholine iodide or echothiophate or carbonic anhydrase inhibitors, microchip implantation, stem cell therapy, gene replacement therapy, ribozyme gene therapy, photoreceptor/retinal cells transplantation, and acupuncture.

In any of the aforementioned aspects are further embodiments comprising the use of laser photocoagulation to remove drusen from the eye of the mammal.

In any of the aforementioned aspects are further embodiments comprising administering to the mammal at least once an effective amount of a second compound having the structure of Formula (I), wherein the first compound is different from the second compound.

In any of the aforementioned aspects are further embodiments comprising (a) monitoring formation of drusen in the eye of the mammal; (b) measuring levels of lipofuscin in the eye of the mammal by autofluorescence; (c) measuring visual acuity in the eye of the mammal; (d) conducting a visual field examination on the eye of the mammal, including embodiments in which the visual field examination is a HumDhrev visual field exam: (e) measuring the autofluorescence or absorption spectra of N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine in the eye of the mammal; (f) conducting a reading speed and/or reading acuity examination; (g) measuring scotoma size; or (h) measuring the size and number of the geographic atrophy lesions.

In any of the aforementioned aspects are further embodiments comprising determining whether the mammal is a carrier of the mutant ABCA4 allele for Stargardt Disease or has a mutant ELOV4 allele for Stargardt Disease or has a genetic variation in complement factor H associated with age-related macular degeneration.

In any of the aforementioned aspects are further embodiments comprising an additional treatment for retinal degeneration.

In another aspect are pharmaceutical compositions comprising an effective amount of compound having the structure:

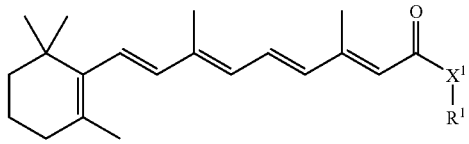

wherein $X_1$ is selected from the group consisting of $NR^2$, O, S, $CHR^2$; $R^1$ is $(CHR^2)_x$-$L^1$-$R^3$, wherein x is 0, 1, 2, or 3; $L^1$ is a single bond or —C(O)—; $R^2$ is a moiety selected from the group consisting of H, $(C_1$-$C_4)$alkyl, F, $(C_1$-$C_4)$fluoroalkyl, $(C_1$-$C_4)$alkoxy, —C(O)OH, —C(O)—$NH_2$, —$(C_1$-$C_4)$alkylamine, —C(O)—$(C_1$-$C_4)$alkyl, —C(O)—$(C_1$-$C_4)$fluoroalkyl, —C(O)—$(C_1$-$C_4)$alkylamine, and —C(O)—$(C_1$-$C_4)$alkoxy; and $R^3$ is H or a moiety, optionally substituted with 1-3 independently selected substituents, selected from the group consisting of $(C_2$-$C_7)$alkenyl, $(C_2$-$C_7)$alkynyl, aryl, $(C_3$-$C_7)$cycloalkyl, $(C_5$-$C_7)$cycloalkenyl, and a heterocycle; provided that R is not H when both x is 0 and $L^1$ is a single bond; or an active metabolite, or a pharmaceutically acceptable prodrug or solvate thereof; and a pharmaceutically acceptable carrier.

In further embodiment of the pharmaceutical composition aspect, (a) the pharmaceutically acceptable carrier is suitable for ophthalmic administration; (b) the pharmaceutically acceptable carrier comprises lysophosphatidylcholine, monoglyceride and a fatty acid; (c) the pharmaceutically acceptable carrier further comprises flour, a sweetener, and a humectant; (d) the pharmaceutically acceptable carrier comprises corn oil and a non-ionic surfactant; (e) the pharmaceutically acceptable carrier comprises dimyristoyl phosphatidylcholine, soybean oil, t-butyl alcohol and water; (f) the pharmaceutically acceptable carrier comprises ethanol, alkoxylated caster oil, and a non-ionic surfactant; (g) the pharmaceutically acceptable carrier comprises an extended release formulation; or (h) the pharmaceutically acceptable carrier comprises a rapid release formulation.

In further embodiment of the pharmaceutical composition aspect, the pharmaceutical composition further comprising an effective amount of at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, 13-cis-retinoic acid (including derivatives of 13-cis-retinoic acid), 11-cis-retinoic acid (including derivatives of 11-cis-retinoic acid), 9-cis-retinoic acid (including derivatives of 9-cis-retinoic acid), and retinylamine derivatives. In further embodiments, (a) the additional agent is a physiologically acceptable antioxidant; (b) the additional agent is an inducer of nitric oxide production; (c) the additional agent is an anti-inflammatory agent; (d) the additional agent is a physiologically acceptable mineral; (e) the additional agent is a negatively charged phospholipid; (f) the additional agent is a carotenoid; (g) the additional agent is a statin; (h) the additional agent is an anti-angiogenic agent; (i) he additional agent is a matrix metalloproteinase inhibitor; or (j) the additional agent is a 13-cis-retinoic acid.

In another aspect are methods for treating a retinopathy comprising modulating the serum level of retinol in the body of a mammal, including embodiments wherein (a) the retinopathy is juvenile macular degeneration, including Stargardt Disease; (b) the retinopathy is dry form age-related macular degeneration; (c) the retinopathy is cone-rod dystrophy; (d) the retinopathy is retinitis pigmentosa; (e) the retinopathy is wet-form age-related macular degeneration; (f) the retinopathy is or presents geographic atrophy and/or photoreceptor degeneration; or (g) the retinopathy is a lipofuscin-based retinal degeneration.

In a embodiment of the aforementioned aspect, the method further comprises administering to the mammal at least once an effective amount of a first compound having the structure:

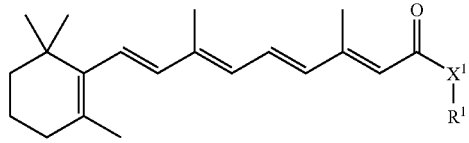

wherein $X_1$ is selected from the group consisting of $NR^2$, O, S, $CHR^2$; $R^1$ is $(CHR^2)_x$-$L^1$-$R^3$, wherein x is 0, 1, 2, or 3; $L^1$ is a single bond or —C(O)—; $R^2$ is a moiety selected from the group consisting of H, $(C_1$-$C_4)$alkyl, F, $(C_1$-$C_4)$fluoroalkyl, $(C_1$-$C_4)$alkoxy, —C(O)OH, —C(O)—$NH_2$, —$(C_1$-$C_4)$alkylamine, —C(O)—$(C_1$-$C_4)$alkyl, —C(O)—$(C_1$-$C_4)$fluoroalkyl, —C(O)—$(C_1$-$C_4)$alkylamine, and —C(O)—$(C_1$-$C_4)$alkoxy; and $R^3$ is H or a moiety, optionally substituted with 1-3 independently selected substituents, selected from the group consisting of $(C_2$-$C_7)$alkenyl, $(C_2$-$C_7)$alkynyl, aryl, $(C_3$-$C_7)$cycloalkyl, $(C_5$-$C_7)$cycloalkenyl, and a heterocycle; provided that R is not H when both x is 0 and $L^1$ is a single bond; or an active metabolite, or a pharmaceutically acceptable prodrug or solvate thereof.

In yet a further embodiment, the method further comprises administering at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, 13-cis-retinoic acid (including derivatives of 13-cis-retinoic acid), 11-cis-retinoic acid (including derivatives of 11-cis-retinoic acid), 9-cis-retinoic acid (including derivatives of 9-cis-retinoic acid), and retinylamine derivatives. Further embodiments include methods wherein: (a) the additional agent is an inducer of nitric oxide production; (b) the additional agent is an anti-inflammatory agent; (c) the additional agent is at least one physiologically acceptable antioxidant; (d) the additional agent is at least one physiologically acceptable mineral; (e) the additional agent is a negatively charged phospholipid; (f) the additional agent is a carotenoid; (g) the additional agent is a statin; (h) the additional agent is an anti-angiogenic drug; (i) the additional agent is a matrix metalloproteinase inhibitor; or (j) the additional agent is 13-cis-retinoic acid.

In a further embodiment of the aforementioned aspect, the method for treating a retinopathy further comprises modulating lecithin-retinol acyltransferase in an eye of a mammal, including embodiments wherein (a) the retinopathy is juvenile macular degeneration, including Stargardt Disease; (b) the retinopathy is dry form age-related macular degeneration; (c) the retinopathy is cone-rod dystrophy; (d) the retinopathy is retinitis pigmentosa; (e) the retinopathy is wet-form age-related macular degeneration; (f) the retinopathy is or presents geographic atrophy and/or photoreceptor degeneration; or (g) the retinopathy is a lipofuscin-based retinal degeneration. In yet a further embodiment, the method further comprises administering to the mammal at least once an effective amount of a first compound having the structure:

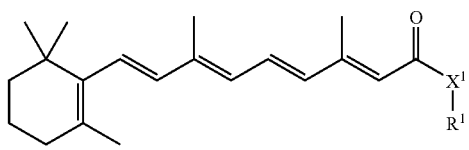

wherein $X_1$ is selected from the group consisting of $NR^2$, O, S, $CHR^2$; $R^1$ is $(CHR^2)_x$-$L^1$-$R^3$, wherein x is 0, 1, 2, or 3; $L^1$ is a single bond or —C(O)—; $R^2$ is a moiety selected from the group consisting of H, $(C_1$-$C_4)$alkyl, F, $(C_1$-$C_4)$fluoroalkyl, $(C_1$-$C_4)$alkoxy, —C(O)OH, —C(O)—$NH_2$, —$(C_1$-$C_4)$alkylamine, —C(O)—$(C_1$-$C_4)$alkyl, —C(O)—$(C_1$-$C_4)$fluoroalkyl, —C(O)—$(C_1$-$C_4)$alkylamine, and —C(O)—$(C_1$-$C_4)$alkoxy; and $R^3$ is H or a moiety, optionally substituted with 1-3 independently selected substituents, selected from the group consisting of $(C_2$-$C_7)$alkenyl, $(C_2$-$C_7)$alkynyl, aryl, $(C_3$-$C_7)$cycloalkyl, $(C_5$-$C_7)$cycloalkenyl, and a heterocycle; provided that R is not H when both x is 0 and $L^1$ is a single bond; or an active metabolite, or a pharmaceutically acceptable prodrug or solvate thereof.

In still a further embodiment, the method further comprises administering at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, 13-cis-retinoic acid (including derivatives of 13-cis-retinoic acid), 11-cis-retinoic acid (including derivatives of 11-cis-retinoic acid), 9-cis-retinoic acid (including derivatives of 9-cis-retinoic acid), and retinylamine derivatives. Further embodiments include methods wherein: (a) the additional agent is an inducer of nitric oxide production; (b) the additional agent is an anti-inflammatory agent; (c) the additional agent is at least one physiologically acceptable antioxidant; (d) the additional agent is at least one physiologically acceptable mineral; (e) the additional agent is a negatively charged phospholipid; (f) the additional agent is a carotenoid; (g) the additional agent is a statin; (h) the additional agent is an anti-angiogenic drug; (i) the additional agent is a matrix metalloproteinase inhibitor; or (j) the additional agent is 13-cis-retinoic acid.

In another aspect are methods for treating retinopathy comprising administering to a mammal an agent that impairs the night vision of the mammal, including embodiments wherein (a) the retinopathy is juvenile macular degeneration, including Stargardt Disease; (b) the retinopathy is dry form age-related macular degeneration; (c) the retinopathy is cone-rod dystrophy; (d) the retinopathy is retinitis pigmentosa; (e) the retinopathy is wet-form age-related macular degeneration; (f) the retinopathy is or presents geographic atrophy and/or photoreceptor degeneration; or (g) the retinopathy is a lipofuscin-based retinal degeneration. In yet a further embodiment, the method further comprises administering to the mammal at least once an effective amount of a first compound having the structure:

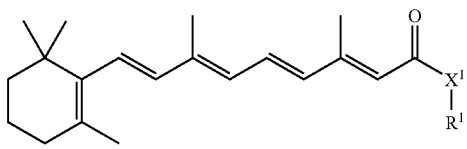

wherein $X_1$ is selected from the group consisting of $NR^2$, O, S, $CHR^2$; $R^1$ is $(CHR^2)_x$-$L^1$-$R^3$, wherein x is 0, 1, 2, or 3; $L^1$ is a single bond or —C(O)—; $R^2$ is a moiety selected from the group consisting of H, $(C_1$-$C_4)$alkyl, F, $(C_1$-$C_4)$fluoroalkyl, $(C_1$-$C_4)$alkoxy, —C(O)OH, —C(O)—$NH_2$, —$(C_1$-$C_4)$alkylamine, —C(O)—$(C_1$-$C_4)$alkyl, —C(O)—$(C_1$-$C_4)$fluoroalkyl, —C(O)—$(C_1$-$C_4)$alkylamine, and —C(O)—$(C_1$-$C_4)$alkoxy; and $R^3$ is H or a moiety, optionally substituted with 1-3 independently selected substituents, selected from the group consisting of $(C_2$-$C_7)$alkenyl, $(C_2$-$C_7)$alkynyl, aryl, $(C_3$-$C_7)$cycloalkyl, $(C_5$-$C_7)$cycloalkenyl, and a heterocycle; provided that R is not H when both x is 0 and $L^1$ is a single bond; or an active metabolite, or a pharmaceutically acceptable prodrug or solvate thereof.

In still a further embodiment, the method further comprises administering at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, 13-cis-retinoic acid (including derivatives of 13-cis-retinoic acid), 11-cis-retinoic acid (including derivatives of 11-cis-retinoic acid), 9-cis-retinoic acid (including derivatives of 9-cis-retinoic acid), and retinylamine derivatives. Further embodiments include methods wherein: (a) the additional agent is an inducer of nitric oxide production; (b) the additional agent is an anti-inflammatory agent; (c) the additional agent is at least one physiologically acceptable antioxidant; (d) the additional agent is at least one physiologically acceptable mineral; (e) the additional agent is a negatively charged phospholipid; (f) the additional agent is a carotenoid; (g) the additional agent is a statin; (h) the additional agent is an anti-angiogenic drug; (i) the additional agent is a matrix metalloproteinase inhibitor; or (j) the additional agent is 13-cis-retinoic acid.

In another aspect are pharmaceutical compositions for (a) reducing the formation of N-retinylidene-N-retinylethanolamine, N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine, in an eye of a mammal, (b) reducing the formation of lipofuscin in an eye of a mammal, (c) reducing the formation of drusen in an eye of a mammal, (d) preventing macular degeneration in an eye of a mammal, (e) reducing the formation of all-trans-retinal in an eye of a mammal, (f) disrupting the visual cycle in an eye of a mammal, and/or (g) protecting an eye of a mammal from light, comprising an effective amount of at least one compound having the structure of Formula (I) and a pharmaceutically acceptable carrier.

Compounds, including, but not limited to those having the structure of Formula (I), that find use in (a) reducing the formation of N-retinylidene-N-retinylethanolamine, N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine, in an eye of a mammal, (b) reducing the formation of lipofuscin in an eye of a mammal, (c) reducing the formation of drusen in an eye of a mammal, (d) preventing macular degeneration in an eye of a mammal, (e) reducing the formation of all-trans-retinal in an eye of a mammal, and/or (f) protecting an eye of a mammal from light, have at least one of the following properties: the ability to disrupt the visual cycle in the eye of a mammal, the ability to cause reversible night blindness in a mammal, acceptable bioavailability to the eye of a mammal, and the ability to cause only limited and acceptable irritation to the eye of a mammal.

In another or further aspect are methods for reducing the formation of or limiting the spread of geographic atrophy and/or photoreceptor degeneration in an eye of a mammal comprising administering to the mammal at least once an effective amount of a first compound having the structure of Formula (I). In further or alternative embodiments are methods further comprising administering at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, 13-cis-retinoic acid (including derivatives of 13-cis-retinoic acid), 11-cis-retinoic acid (including derivatives of 11-cis-retinoic acid), 9-cis-retinoic acid (including derivatives of 9-cis-retinoic acid), and retinylamine derivatives.

In further or alternative embodiments of any of the aforementioned methods involving the administration of a compound having the structure of Formula (I) are methods further comprising measuring the reading speed and/or reading acuity of the mammal.

In further or alternative embodiments of any of the aforementioned methods involving the administration of a compound having the structure of Formula (I) are methods further comprising measuring the number and/or size of the scotoma in the eye of the mammal.

In further or alternative embodiments of any of the aforementioned methods involving the administration of a compound having the structure of Formula (I) are methods further comprising measuring the size and/or number of the geographic atrophy lesions in the eye of the mammal.

In further or alternative embodiments of any of the aforementioned methods involving the administration of a compound having the structure of Formula (I) are methods further comprising reducing the esterification of vitamin A in the eye of the mammal.

In further or alternative embodiments of any of the aforementioned methods involving the administration of a compound having the structure of Formula (I) are methods further comprising ising lowering the autofluorescence of lipofuscin in the retinal pigment epithelium in the eye of the mammal.

In further or alternative embodiments of any of the aforementioned methods involving the administration of a compound having the structure of Formula (I) are methods further comprising reducing the concentration of a substrate for a visual cycle protein downstream from LRAT in the eye of the mammal. In further or alternative embodiments, the downstream visual cycle protein is selected from the group consisting of a chaperone protein, an isomerase, and a dehydrogenase.

In a further aspect are methods for reducing the concentration of a substrate for a visual cycle protein downstream from LRAT in an eye of a mammal comprising administering to the mammal at least once an effective amount of a first compound having the structure of Formula (I). In further or alternative embodiments, the downstream visual cycle protein is selected from the group consisting of a chaperone protein, an isomerase, and a dehydrogenase.

In a further aspect are methods for reducing the esterification of vitamin A in an eye of a mammal comprising administering to the mammal at least once an effective amount of a first compound having the structure of Formula (I).

In another aspect are methods for modulating the activity of Cellular Retinaldehyde Binding Protein (CRALBP) comprising contacting CRALBP with compounds having the structure of Formula (I). In a further embodiment, the compound directly contacts Cellular Retinaldehyde Binding Protein. In a further embodiment, such modulation occurs in vivo. In an alternative embodiment, such modulation occurs in vitro. In a further embodiment, such modulation occurs in the eye of a mammal. In a further embodiment, such modulation provides therapeutic benefit to a mammal having an ophthalmic disease or condition. In a further embodiment, such modulation improves or otherwise alleviates at least one symptom associated with an ophthalmic disease or condition in a mammal. In further or alternative embodiments, the disease or condition is selected from the group consisting of a macular degeneration, a macular dystrophy, a retinopathy. In further or alternative embodiments, the compound is 4-hydroxyphenylretinamide; or a metabolite, or a pharmaceutically acceptable prodrug or solvate thereof. In further or alternative embodiments, the compound is 4-methoxyphenylretinamide; or a metabolite, or a pharmaceutically acceptable prodrug or solvate thereof.

In another aspect are methods for indirectly modulating the activity of visual cycle proteins that are not directly modulated by the compounds of Formula (I). In one embodiment of such an aspect, the compounds of Formula (I) directly modulate one of the visual cycle proteins (by binding to such a protein or by binding to the ligand of such a protein, wherein the binding may be chemical binding, physical binding, or a combination thereof, including hydrogen bonding) so as to reduce the concentration of the expected reaction product of the that visual cycle protein. In a further embodiment, the visual cycle protein that is directly modulated by the compounds of Formula (I) is LRAT. In a further embodiment, the direct modulation of LRAT by a compound of Formula (I) reduces the concentration of all-trans-retinyl esters. In a further embodiment, reduction in the concentration of all-trans-retinyl esters indirectly modulates the activity of downstream visual cycle proteins by lowering the concentration of substrates for such downstream visual cycle proteins. In further embodiments, such downstream visual cycle proteins include isomerases, chaperone proteins, and dehydrogenases.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

All references cited herein, including patents, patent applications, and publications, are hereby incorporated by reference in their entirety.

BRIEF DESCRIPTION OF THE FIGURES

FIGS. 1a-1c illustrate various reverse phase LC analyses of acetonitrile extracts of serum. The serum was obtained from mice administered with either DMSO (FIG. 1a), 10 mg/kg N-4-(hydroxyphenyl)retinamide (HPR) (FIG. 1b), or 20 mg/kg HPR (FIG. 1c) for 14 days.

FIG. 18 illustrates the analysis of A2PE-$H_2$ and A2E levels as a function of fenretinide dose and treatment period (panels A-F) and lipofuscin autofluorescence in the RPE of ABCA4 null mutant mice as a function of fenretinide treatment (panels G-I).

DETAILED DESCRIPTION OF THE INVENTION

Figure 2A:
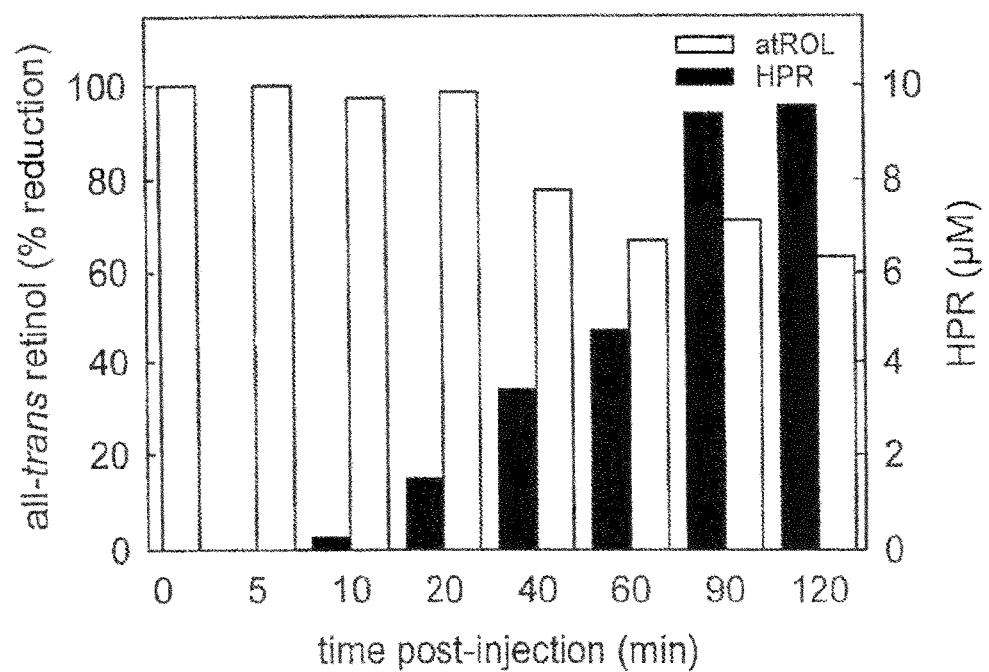
FIG. 2a illustrates ocular concentrations of all-trans retinol (atROL) and HPR as a function of time in mice following injection of 10 mg/kg HPR.
Figure 2B:
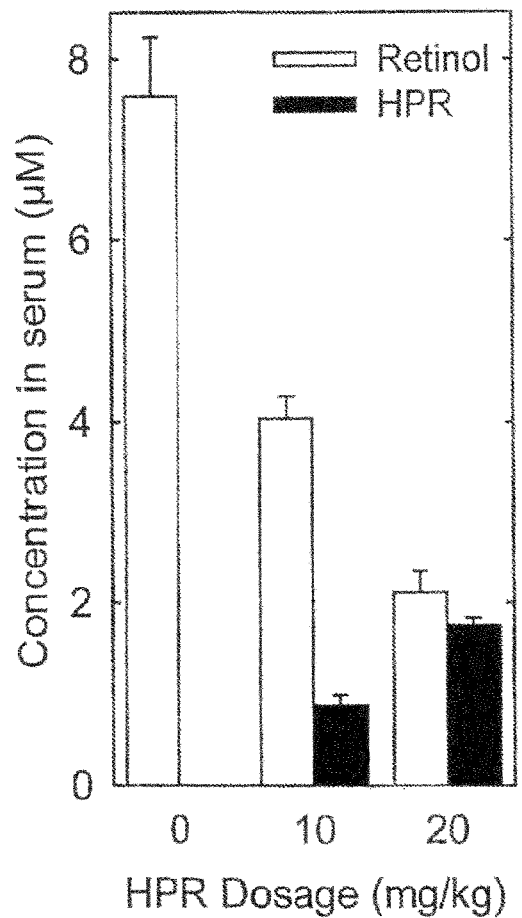
FIG. 2b illustrates serum concentrations of all-trans retinol and HPR in mice following 14-day treatment with DMSO, 10 mg/kg HPR, or 20 mg/kg HPR; see FIG. 11 for an updated and corrected version of this figure.

Compounds having the structure of Formula (I) have been used for the treatment of cancer. In particular, the compound N-(4-hydroxyphenyl)retinamide, also known as fenretinide, HPR or 4-HPR, has been extensively tested for the treatment of breast cancer. Moon, et al., *Cancer Res.*, 39:1339-46 (1979). Fenretinide is described in U.S. Pat. Nos. 4,190,594 and 4,323,581. In addition, other methods for preparing fenretinide are known, and further, numerous analogs of fenretinide have been prepared and tested for their effectiveness in treating cancer. See, e.g., U.S. Patent Application Publication 2004/0102650; U.S. Pat. No. 6,696,606; Villeneuve & Chan, *Tetrahedron Letters*, 38:6489-92 (1997); Um, S. J., et al., *Chem. Pharm. Bull.*, 52:501-506 (2004). Of concern, however, has been the general tendency of such compounds to produce certain side-effects in human patients, including impairment of night vision. See, e.g., Decensi, A., et al., *J. Natl. Cancer Inst.*, 86:1-5-110 (1994); Mariani, L., *Tumori.*, 82:444-49 (1996). A recent study has also provided some evidence that N-(4-hydroxyphenyl)retinamide can induce neuronal-like differentiation in certain cultured human RPE cells. See Chen, S., et al., *J. Neurochem.*, 84:972-81 (2003).

Surprisingly, the compounds of Formula (I) can be used to provide benefit to patients suffering from or susceptible to various macular degenerations and dystrophies, including but not limited to dry-form age-related macular degeneration and Stargardt Disease. Specifically, compounds of Formula (I) provide at least some of the following benefits to such human patients: reduction in the amount of all-trans-retinal (atRAL), reduction in the formation of A2E, reduction in the formation of lipofuscin, reduction in the formation of drusen, and reduction in light sensitivity. There is a reduced tendency to form A2E in ophthalmic and ocular tissues caused, in part, by a reduction in the over-accumulation of all-trans-retinal in these tissues. Because A2E itself is cytotoxic to the RPE (which can lead to retina cell death), administration of compounds having the structure of Formula (I) (alone, or in combination with other agents, as described herein) reduces the rate of accumulation of A2E, a cytotoxic agent, thus providing patient benefit. In addition, because A2E is the major fluorophore of lipofuscin, reduced quantities of A2E in ophthalmic and ocular tissues also results in a reduced tendency to accumulate lipofuscin in such tissues. Thus, in some respects the methods and compositions described herein can be considered to be lipofuscin-based treatments because administration of compounds having the structure of Formula (I) (alone, or in combination with other agents, as described herein) reduces, lowers or otherwise impacts the accumulation of lipofuscin in ophthalmic and/or ocular tissues. A reduction in the rate of accumulation of lipofuscin in ophthalmic and/or ocular tissues benefits patients that have diseases or conditions such as macular degenerations and/or dystrophies.

In addition, because dry-form age-related macular degeneration is often a precursor to wet-form age-related macular degeneration, the use of compounds of Formula (I) can also be used as a preventative therapy for this latter ophthalmic condition.

Interestingly, the compounds of Formula (I) and/or its derivatives also have an effect on enzymes or proteins in the visual cycle. For example esterification in the retinal pigment epithelium involves lecithin-retinol acyltransferase (LRAT) which catalyzes the transfer of an acyl group from lecithin to retinol. Administration of Formula (I) and/or its derivatives modifies the activity of LRAT which could benefit patients suffering from or susceptible to various macular degenerations and dystrophies.

Vitamin A in serum is delivered to extra-hepatic target tissues and immediately esterified by the membrane-bound enzyme LRAT. LRAT catalyzes the transfer of a fatty acid from membrane phospholipids to retinol thereby generating all-trans retinyl esters, the principal storage form of vitamin A in all tissues. In the RPE, all-trans retinyl esters are the sole substrate for a unique isomerase enzyme which generates a light-sensitive visual chromophore precursor, 11-cis retinol. Subsequent oxidation of this retinoid and conjugation to the opsin apoprotein in the retina yields rhodopsin.

N-4-(hydroxyphenyl)retinamide has been shown to cause marked inhibition of LRAT activity in membranes prepared from liver and small intestine. Additionally, we have demonstrated (e.g., Example 13) for the first time that LRAT activity in the RPE of the eye is inhibited by HPR. As discussed in the Examples, administration of HPR is also associated with decreased serum retinol and retinol binding protein (RBP). Thus, in addition to the systemic effects of HPR (e.g., decreased serum retinol levels), there is also an intracellular, enzyme-specific effect (e.g., LRAT activity in RPE cells). The fact that vitamin A homeostasis in the eye relies not only upon delivery of retinol from serum but also upon intracellular stores of retinyl esters to provide visual chromophore, suggests that effects of HPR may be most pronounced in this organ.

Figure 7:
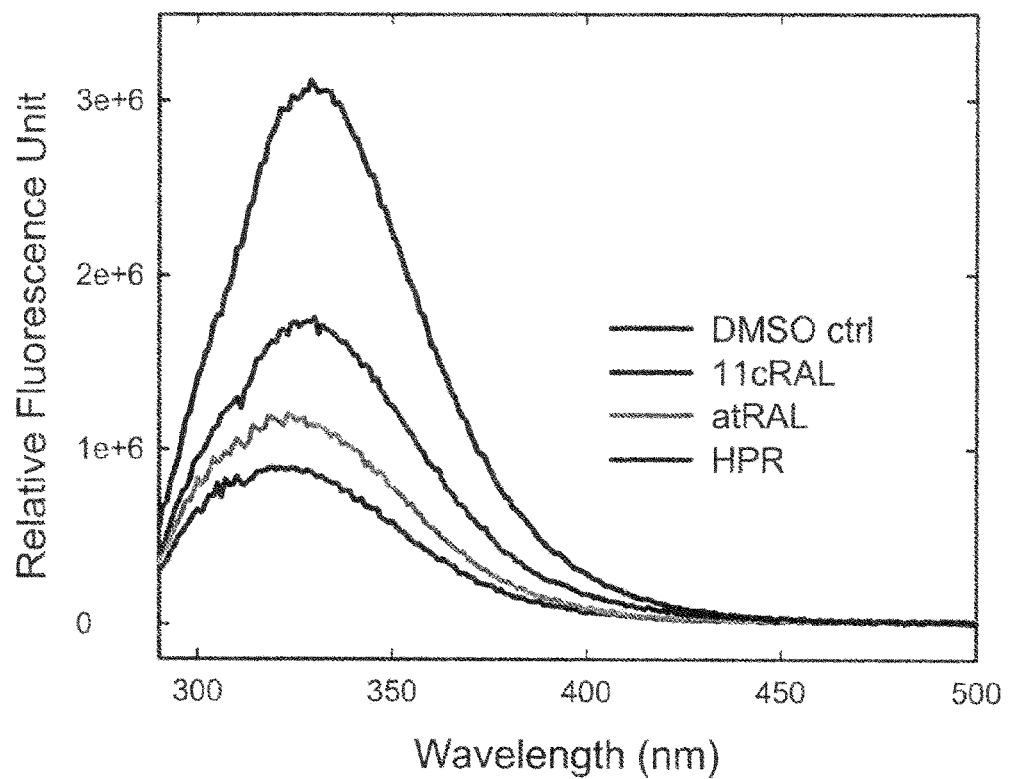
FIG. 7 illustrates the interaction of Cellular Retinaldehyde Binding Protein (CRALBP) with various ligands as measured by fluorescence quenching.
Figure 8:
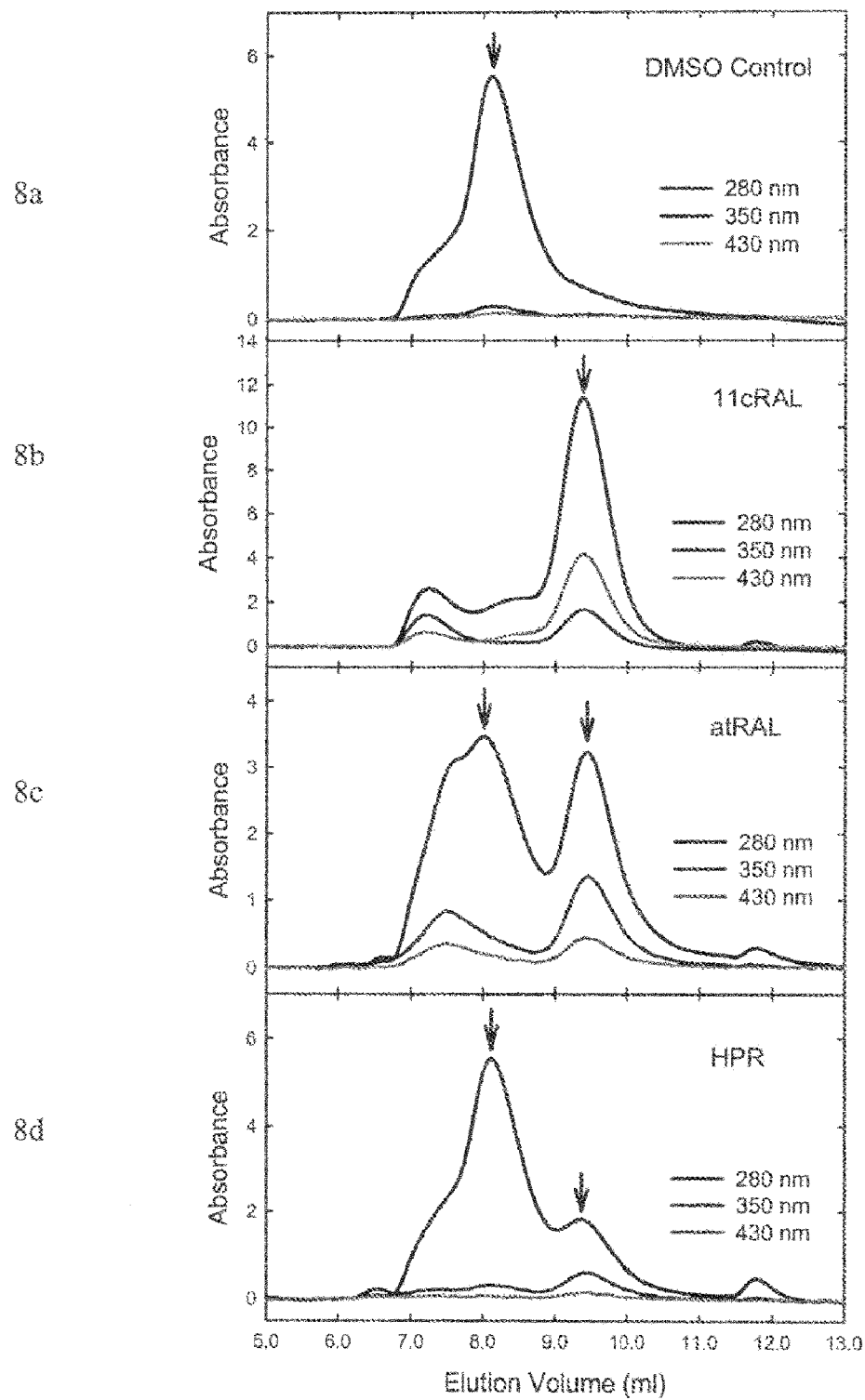
FIG. 8 illustrates the interaction of CRALBP with various ligands as measured by size exclusion chromatography and UV/Visible spectrophotometry.

In addition, compounds having the structure of Formula (I) also bind to Cellular Retinaldehyde Binding Protein (CRALBP), which is another visual cycle protein. To illustrate this effect, and by way of example only, the data presented in FIGS. 7 & 8 demonstrate that HPR binds to CRALBP. Thus, in ophthalmic tissues, where CRALBP can be found, compounds having the structure of Formula (I) are expected to bind to CRALBP, and consequently, (a) modulate the binding of other compounds, such as retinaldehyde, to CRALBP, (b) modulate the activity of CRALBP, (c) serve as a ligand to CRALBP, (d) undergo activity catalyzed by CRALBP, including transport activity, and/or (e) serve as a therapeutic agent in the methods and compositions described herein.

The Visual Cycle. The vertebrate retina contains two types of photoreceptor cells—rods and cones. Rods are specialized for vision under low light conditions. Cones are less sensitive, provide vision at high temporal and spatial resolutions, and afford color perception. Under daylight conditions, the rod response is saturated and vision is mediated entirely by cones. Both cell types contain a structure called the outer segment comprising a stack of membranous discs. The reactions of visual transduction take place on the surfaces of these discs. The first step in vision is absorption of a photon by an opsin-pigment molecule (rhodopsin), which involves 11-cis to all-trans isomerization of the chromophore. Before light sensitivity can be regained, the resulting all-trans-retinal must be converted back 11-cis-retinal in a multi-enzyme process which takes place in the retinal pigment epithelium, a monolayer of cells adjacent to the retina.

Macular or Retinal Degenerations and Dystrophies. Macular degeneration (also referred to as retinal degeneration) is a disease of the eye that involves deterioration of the macula, the central portion of the retina. Approximately 85% to 90% of the cases of macular degeneration are the "dry" (atrophic or non-neovascular) type. In dry macular degeneration, the deterioration of the retina is associated with the formation of small yellow deposits, known as drusen, under the macula; in addition, the accumulation of lipofuscin in the RPE leads to photoreceptor degeneration and geographic atrophy. This phenomena leads to a thinning and drying out of the macula. The location and amount of thinning in the retina caused by the drusen directly correlates to the amount of central vision loss. Degeneration of the pigmented layer of the retina and photoreceptors overlying drusen become atrophic and can cause a slow loss of central vision. Ultimately, loss of retinal pigment epithelium and underlying photoreceptor cells results in geographic atrophy. Administration of at least one compound having the structure of Formula (I) to a mammal can reduce the formation of, or limit the spread of, photoreceptor degeneration and/or geographic atrophy in the eye of the mammal. By way of example only, administration of HPR and/or MPR to a mammal, can be used to treat photoreceptor degeneration and/or geographic atrophy in the eye of the mammal.

In "wet" macular degeneration new blood vessels form (i.e., neovascularization) to improve the blood supply to retinal tissue, specifically beneath the macula, a portion of the retina that is responsible for our sharp central vision. The new vessels are easily damaged and sometimes rupture, causing bleeding and injury to the surrounding tissue. Although wet macular degeneration only occurs in about 10 percent of all macular degeneration cases, it accounts for approximately 90% of macular degeneration-related blindness. Neovascularization can lead to rapid loss of vision and eventual scarring of the retinal tissues and bleeding in the eye. This scar tissue and blood produces a dark, distorted area in the vision, often rendering the eye legally blind. Wet macular degeneration usually starts with distortion in the central field of vision. Straight lines become wavy. Many people with macular degeneration also report having blurred vision and blank spots (scotoma) in their visual field. Growth promoting proteins called vascular endothelial growth factor, or VEGF, have been targeted for triggering this abnormal vessel growth in the eye. This discovery has lead to aggressive research of experimental drugs that inhibit or block VEGF. Studies have shown that anti-VEGF agents can be used to block and prevent abnormal blood vessel growth. Such anti-VEGF agents stop or inhibit VEGF stimulation, so there is less growth of blood vessels. Such anti-VEGF agents may also be successful in anti-angiogenesis or blocking VEGF's ability to induce blood vessel growth beneath the retina, as well as blood vessel leakiness. Administration of at least one compound having the structure of Formula (I) to a mammal can reduce the formation of, or limit the spread of, wet-form age-related macular degeneration in the eye of the mammal. By way of example only, administration of HPR and/or MPR to a mammal, can be used to treat wet-form age-related macular degeneration in the eye of the mammal. Similarly, the compounds of Formula (I) (including by way of example only, HPR and/or MPR) can be used to treat choroidal neovascularization and the formation of abnormal blood vessels beneath the macula of the eye of a mammal.

Stargardt Disease is a macular dystrophy that manifests as a recessive form of macular degeneration with an onset during childhood. See e.g., Allikmets et al., Science, 277:1805-07 (1997); Lewis et al., Am. J. Hum. Genet., 64:422-34 (1999); Stone et al., Nature Genetics, 20:328-29 (1998); Allikmets, Am. J. Hum. Gen., 67:793-799 (2000); Klevering, et al, Ophthalmology, 111:546-553 (2004). Stargardt Disease is characterized clinically by progressive loss of central vision and progressive atrophy of the RPE overlying the macula. Mutations in the human ABCA4 gene for Rim Protein (RmP) are responsible for Stargardt Disease. Early in the disease course, patients show delayed dark adaptation but otherwise normal rod function. Histologically, Stargardt Disease is associated with deposition of lipofuscin pigment granules in RPE cells.

Mutations in ABCA4 have also been implicated in recessive retinitis pigmentosa, see, e.g., Cremers et al., Hum. Mol. Genet., 7:355-62 (1998), recessive cone-rod dystrophy, see id., and non-exudative age-related macular degeneration, see e.g., Allikmets et al., Science, 277:1805-07 (1997); Lewis et al., Am. J. Hum. Genet., 64:422-34 (1999), although the prevalence of ABCA4 mutations in AMD is still uncertain. See Stone et al., Nature Genetics, 20:328-29 (1998); Allikmets, Am. J. Hum. Gen., 67:793-799 (2000); Klevering, et al., Ophthalmology, 111:546-553 (2004). Similar to Stargardt Disease, these diseases are associated with delayed rod dark-adaptation. See Steinmetz et al., Brit. J. Ophthalm., 77:549-54 (1993). Lipofuscin deposition in RPE cells is also seen prominently in AMD, see Kliffen et al., Microsc. Res. Tech., 36:106-22 (1997) and some cases of retinitis pigmentosa. See Bergsma et al., Nature, 265:62-67 (1977). In addition, an autosomal dominant form of Stargardt Disease is caused by mutations in the ELOV4 gene. See Karan, et al., Proc. Natl. Acad. Sci. (2005).

In addition, there are several types of macular degenerations that affect children, teenagers or adults that are commonly known as early onset or juvenile macular degeneration. Many of these types are hereditary and are looked upon as macular dystrophies instead of degeneration. Some examples of macular dystrophies include: Cone-Rod Dystrophy, Corneal Dystrophy, Fuch's Dystrophy, Sorsby's Macular Dystrophy, Best Disease, and Juvenile Retinoschisis, as well as Stargardt Disease.

Chemical Terminology

An "alkoxy" group refers to a (alkyl)O-group, where alkyl is as defined herein.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 5 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkylamine" refers to the —N(alkyl)$_x$H$_y$ group, where x and y are selected from the group x=1, y=1 and x=2, y=0. When x=2, the alkyl groups, taken together, can optionally form a cyclic ring system.

The term "alkenyl" refers to a type of alkyl group in which the first two atoms of the alkyl group form a double bond that is not part of an aromatic group. That is, an alkenyl group begins with the atoms —C(R)=C—R, wherein R refers to the remaining portions of the alkenyl group, which may be the same or different. Non-limiting examples of an alkenyl group include —CH=CH$_2$, —C(CH$_3$)=CH$_2$, —CH=CCH$_3$ and —C(CH$_3$)=CCH$_3$. The alkenyl moiety may be branched, straight chain, or cyclic (in which case, it would also be known as a "cycloalkenyl" group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. Non-limiting examples of an alkynyl group include —C≡CH, —C≡CCH$_3$ and —C≡CCH$_2$CH$_3$. The "R" portion of the alkynyl moiety may be branched, straight chain, or cyclic.

An "amide" is a chemical moiety with formula —C(O)NHR or —NHC(O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "aromatic" or "aryl" refers to an aromatic group which has at least one ring having a conjugated pi electron system and includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon.

A "cyano" group refers to a —CN group.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

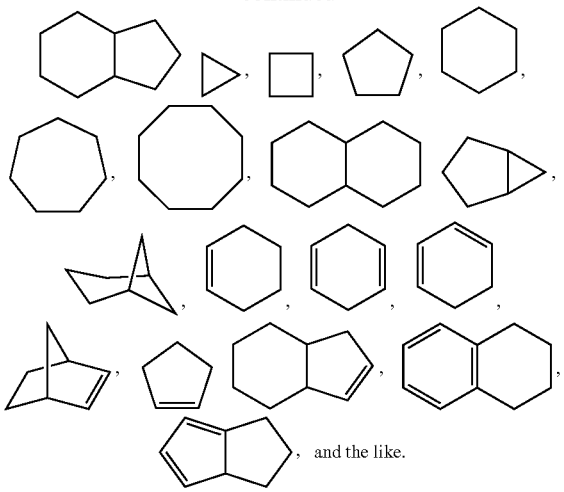

, and the like.

The term "ester" refers to a chemical moiety with formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "halo" or, alternatively, "halogen" means fluoro, chloro, bromo or iodo. Preferred halo groups are fluoro, chloro and bromo.

The terms "haloalkyl," "haloalkenyl," "haloalkynyl" and "haloalkoxy" include alkyl, alkenyl, alkynyl and alkoxy structures that are substituted with one or more halo groups or with combinations thereof. The terms "fluoroalkyl" and "fluoroalkoxy" include haloalkyl and haloalkoxy groups, respectively, in which the halo is fluorine.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

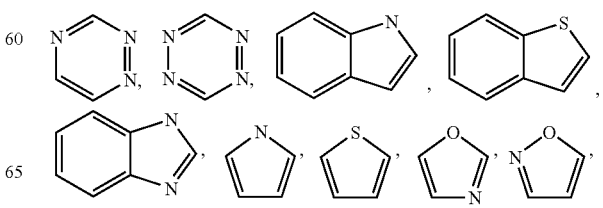

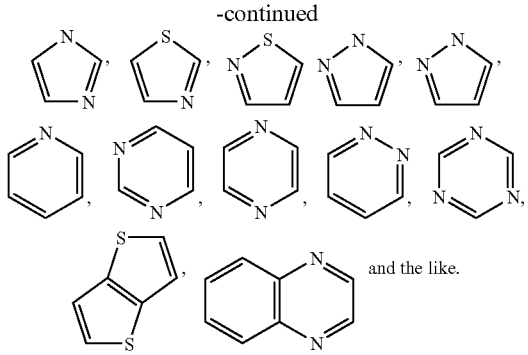

and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol4-yl or imidazol-5-yl (all C-attached). The heterocyclic groups include benzo-fused ring systems and ring systems substituted with one or two oxo (═O) moieties such as pyrrolidin-2-one.

A "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups include:

The term heteroalicyclic also includes all ring forms of the carbohydrates, including but not limited to the monosaccharides, the disaccharides and the oligosaccharides.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

An "isocyanato" group refers to a —NCO group.
An "isothiocyanato" group refers to a —NCS group.
A "mercaptyl" group refers to a (alkyl)S— group.

The terms "nucleophile" and "electrophile" as used herein have their usual meanings familiar to synthetic and/or physical organic chemistry. Carbon electrophiles typically comprise one or more alkyl, alkenyl, alkynyl or aromatic ($SP^3$, $Sp^2$, or sp hybridized) carbon atoms substituted with any atom or group having a Pauling electronegativity greater than that of carbon itself. Examples of carbon electrophiles include but are not limited to carbonyls (aldehydes, ketones, esters, amides), oximes, hydrazones, epoxides, aziridines, alkyl-, alkenyl-, and aryl halides, acyls, sulfonates (aryl, alkyl and the like). Other examples of carbon electrophiles include unsaturated carbon atoms electronically conjugated with electron withdrawing groups, examples being the 6-carbon in alpha-unsaturated ketones or carbon atoms in fluorine substituted aryl groups. Methods of generating carbon electrophiles, especially in ways which yield precisely controlled products, are known to those skilled in the art of organic synthesis.

The relative disposition of aromatic substituents (ortho, meta, and para) imparts distinctive chemistry for such stereoisomers and is well recognized within the field of aromatic chemistry. Para- and meta-substitutional patterns project the two substituents into different orientations. Ortho-disposed substituents are oriented at 60° with respect to one another; meta-disposed substituents are oriented at 120° with respect to one another; para-disposed substituents are oriented at 180° with respect to one another.

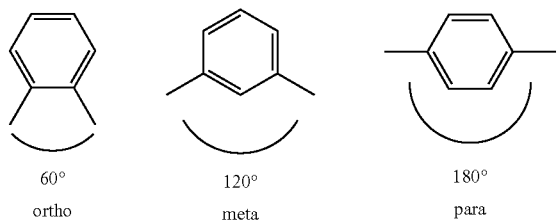

60°
ortho

120°
meta

180°
para

Relative dispositions of substituents, viz, ortho, meta, para, also affect the electronic properties of the substituents. Without being bound to any particular type or level of theory, it is known that ortho- and para-disposed substituents electronically affect one another to a greater degree than do corresponding meta-disposed substituents. Meta-disubstituted aromatics are often synthesized using different routes than are the esponding ortho and para-disubstituted aromatics.

The term "moiety" refers to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

A "sulfinyl" group refers to a —S(=O)—R, where R is selected from the group consisting of alkyl, cycloalkyl, aryl, heteroaryl (bonded through a ring carbon) and heteroalicyclic (bonded through a ring carbon)

A "sulfonyl" group refers to a —S(=O)$_2$—R, where R is selected from the group consisting of alkyl, cycloalkyl, aryl, heteroaryl (bonded through a ring carbon) and heteroalicyclic (bonded through a ring carbon)

A "thiocyanato" group refers to a —CNS group.

The term "optionally substituted" means that the referenced group may be substituted with one or more additional group(s) individually and independently selected from alkyl, cycloalkyl, aryl, heteroaryl, heteroalicyclic, hydroxy, alkoxy, aryloxy, mercapto, alkylthio, arylthio, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. The protecting groups that may form the protective derivatives of the above substituents are known to those of skill in the art and may be found in references such as Greene and Wuts, above.

The compounds presented herein may possess one or more chiral centers and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

The methods and formulations described herein include the use of N-oxides, crystalline forms (also known as polymorphs), or pharmaceutically acceptable salts of compounds having the structure of Formula (I), as well as active metabolites of these compounds having the same type of activity. By way of example only, a known metabolite of fenretinide is N-(4-methoxyphenyl)retinamide, also known as 4-MPR or MPR. Another known metabolite of fenretinide is 4-oxo fenretinide. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Pharmaceutical Compositions

Another aspect are pharmaceutical compositions comprising a compound of Formula (I) and a pharmaceutically acceptable diluent, excipient, or carrier.

The term "pharmaceutical composition" refers to a mixture of a compound of Formula (I) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "carrier" refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The term "physiologically acceptable" refers to a material, such as a carrier or diluent, that does not abrogate the biological activity or properties of the compound, and is nontoxic.

The term "pharmaceutically acceptable salt" refers to a formulation of a compound that does not cause significant irritation to an organism to which it is administered and does not abrogate the biological activity and properties of the compound. Pharmaceutically acceptable salts may be obtained by reacting a compound of Formula (I) with acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts may also be obtained by reacting a compound of Formula (I) with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods known in the art A "metabolite" of a compound disclosed herein is a derivative of that compound that is formed when the compound is metabolized. The term "active metabolite" refers to a biologically active derivative of a compound that is formed when the compound is metabolized. The term "metabolized" refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

By way of example only, MPR is a known metabolite of HPR, both of which are contained within the structure of Formula (I). MPR accumulates systemically in patients that have been chronically treated with HPR. One of the reasons that MPR accumulates systemically is that MPR is only (if at all) slowly metabolized, whereas HPR is metabolized to MPR. In addition, MPR may undergo relatively slow clearance. Thus, (a) the pharmacokinetics and pharmacodynamics of MPR must be taken into consideration when administering and determining the bioavailability of HPR, (b) MPR is more stable to metabolism than HPR, and (c) MPR can be more immediately bioavailable than HPR following absorption. Another known metabolite of fenretinide is 4-oxo fenretinide.

Figure 9:
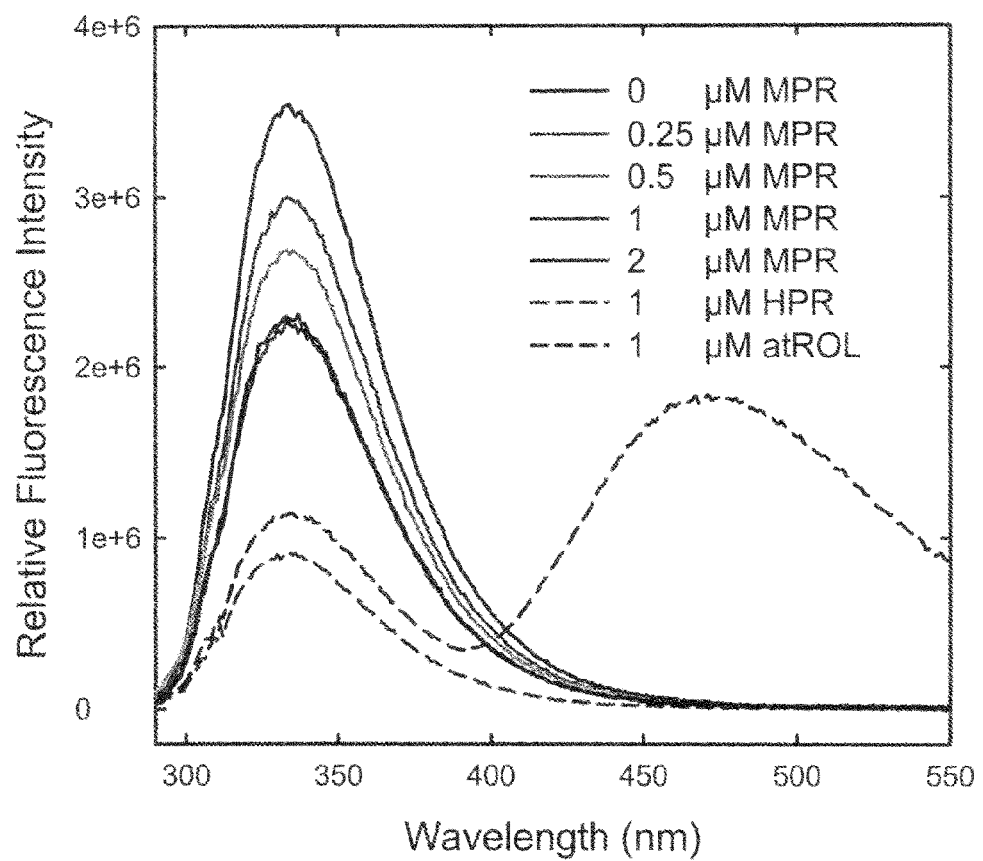
FIG. 9 illustrates the binding of N-4-(methoxyphenyl)retinamide (MPR) to retinol binding protein (RBP) as measured by fluorescence quenching.
Figure 10:
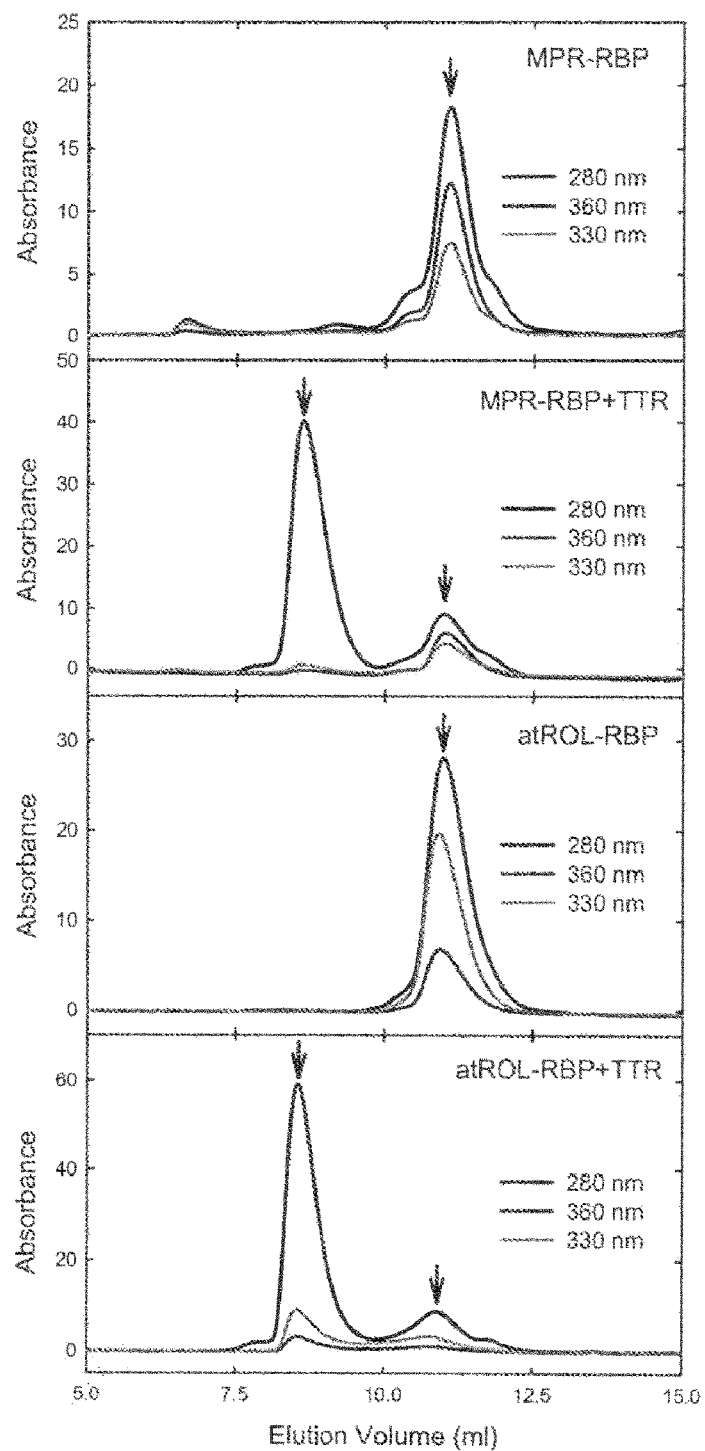
FIG. 10 illustrates the modulation of TTR binding to RBP-MPR as measured by size exclusion chromatography and UV/Visible spectrophotometry.

MPR may also be considered an active metabolite. As shown in FIGS. 9 and 10, MPR (like HPR) can bind to Retinol Binding Protein (RBP) and prevent the binding of RBP to Transerythrin (TTR). As a result, when either HPR or MPR is administered to a patient, one of the resulting expected features is that MPR will accumulate and bind to RBP and inhibit binding of retinol to RBP, as well as the binding of RBP to TTR. Accordingly, MPR can (a) serve as an inhibitor of retinol binding to RBP, (b) serve as an inhibitor of RBP to TTR, (c) limit the transport of retinol to certain tissues, including ophthalmic tissues, and (d) be transported by RBP to certain tissues, including ophthalmic tissues. MPR appears to bind more weakly to RBP than HPR, and is thus a less strong inhibitor of retinol binding to RBP. Nevertheless, both MPR and HPR are expected to inhibit, approximately equivalently, the binding of RBP to TTR. Furthermore, it is expected that MPR (like HPR) will bind to visual cycle proteins, including LRAT and CRALBP. MPR has, in these respects, the same mode of action as HPR and can serve as a therapeutic agent in the methods and compositions described herein.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of Formula (I) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The compounds described herein can be administered to a human patient per se, or in pharmaceutical compositions where they are mixed with other active ingredients, as in combination therapy, or suitable carrier(s) or excipient(s). Techniques for formulation and administration of the compounds of the instant application may be found in "Remington: The Science and Practice of Pharmacy," 20th ed. (2000).

Routes Of Administration

Suitable routes of administration may, for example, include oral, rectal, transmucosal, transdermal, pulmonary, ophthalmic or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into an organ, often in a depot or sustained release formulation. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Composition/Formulation

Pharmaceutical compositions comprising a compound of Formula (I) may be manufactured in a manner that is itself known, e.g., by means of conventional mixing, dissolving, granulating, dragee-making, levigating, emulsifying, encapsulating, entrapping or compression processes.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

The compounds of Formula (I) can be administered in a variety of ways, including all forms of local delivery to the eye. Additionally, the compounds of Formula (I) can be administered systemically, such as orally or intravenously. The compounds of Formula (I) can be administered topically to the eye and can be formulated into a variety of topically administrable ophthalmic compositions, such as solutions, suspensions, gels or ointments. Thus, "ophthalmic administration" encompasses, but is not limited to, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the fornix).

Administration of a composition to the eye generally results in direct contact of the agents with the cornea, through which at least a portion of the administered agents pass. Often, the composition has an effective residence time in the eye of about 2 to about 24 hours, more typically about 4 to about 24 hours and most typically about 6 to about 24 hours.

A composition comprising a compound of Formula (I) can illustratively take the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition may include a gel formulation. In other embodiments, the liquid composition is aqueous. Alternatively, the composition can take the form of an ointment.

Useful compositions can be an aqueous solution, suspension or solution/suspension, which can be presented in the form of eye drops. A desired dosage can be administered via a known number of drops into the eye. For example, for a drop volume of 25 µl, administration of 1-6 drops will deliver 25-150 µl of the composition. Aqueous compositions typically contain from about 0.01% to about 50%, more typically about 0.1% to about 20%, still more typically about 0.2% to about 10%, and most typically about 0.5% to about 5%, weight/volume of a compound of Formula (I).

Typically, aqueous compositions have ophthalmically acceptable pH and osmolality. "Ophthalmically acceptable" with respect to a formulation, composition or ingredient typically means having no persistent detrimental effect on the treated eye or the functioning thereof, or on the general health of the subject being treated. Transient effects such as minor irritation or a "stinging" sensation are common with topical ophthalmic administration of agents and consistent with the formulation, composition or ingredient in question being "ophthalmically acceptable."

Useful aqueous suspension can also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions can also comprise an ophthalnically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful compositions may also include ophthalmically acceptable solubilizing agents to aid in the solubility of a compound of Formula (I). The term "solubilizing agent" generally includes agents that result in formation of a micellar solution or a true solution of the agent. Certain ophthalmically acceptable nonionic surfactants, for example polysorbate 80, can be useful as solubilizing agents, as can ophthalmically acceptable glycols, polyglycols, e.g., polyethylene glycol 400, and glycol ethers.

Useful compositions may also include one or more ophthalmically acceptable pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

Useful compositions may also include one or more ophthalmically acceptable salts in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful compositions may also include one or more ophthalmically acceptable preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions may include one or more ophthalmically acceptable surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions may include one or more antioxidants to enhance chemical stability where required. Suitable antioxidants include, by way of example only, ascorbic acid and sodium metabisulfite.

Aqueous suspension compositions can be packaged in single-dose non-reclosable containers. Alternatively, multiple-dose reclosable containers can be used, in which case it is typical to include a preservative in the composition.

The ophthalmic composition may also take the form of a solid article that can be inserted between the eye and eyelid or in the conjunctival sac, where it releases the agent. Release is to the lacrimal fluid that bathes the surface of the cornea, or directly to the cornea itself, with which the solid article is generally in intimate contact. Solid articles suitable for implantation in the eye in such fashion are generally composed primarily of polymers and can be biodegradable or non-biodegradable.

For intravenous injections, compounds of Formula (I) may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

One useful formulation for solubilizing higher quantities of the compounds of Formula (I) are, by way of example only, positively, negatively or neutrally charged phospholipids, or bile salt/phosphatidylcholine mixed lipid aggregate systems, such as those described in Li, C. Y., et al., *Pharm. Res.* 13:907-913 (1996). An additional formulation that can be used for the same purpose with compounds having the structure of Formula (I) involves use of a solvent comprising an alcohol, such as ethanol, in combination with an alkoxylated caster oil. See, e.g., U.S. Patent Publication Number 2002/0183394. Or, alternatively, a formulation comprising a compound of Formula (I) is an emulsion composed of a lipoid dispersed in an aqueous phase, a stabilizing amount of a non-ionic surfactant, optionally a solvent, and optionally an isotonic agent. See id. Yet another formulation comprising a compound of Formula (I) includes corn oil and a non-ionic surfactant. See U.S. Pat. No. 4,665,098. Still another formulation comprising a compound of Formula (I) includes lysophosphatidylcholine, monoglyceride and a fatty acid. See U.S. Pat. No. 4,874,795. Still another formulation comprising a compound of Formula (I) includes flour, a sweetener, and a humectant. See International Publication No. WO 2004/069203. And still another formulation comprising a compound of Formula (I) includes dimyristoyl phosphatidylcholine, soybean oil, t-butyl alcohol and water. See U.S. Patent Application Publication No. US 2002/0143062.

For oral administration, compounds of Formula (I) can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner.

Another useful formulation for administration of compounds having the structure of Formula (I) employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents. Still further, transdermal delivery of the compounds of Formula (I) can be accomplished by means of iontophoretic patches and the like. Transdermal patches can provide controlled delivery of the compounds. The rate of absorption can be slowed by using rate-controlling membranes or by trapping the compound within a polymer matrix or gel. Conversely, absorption enhancers can be used to increase absorption. Formulations suitable for transdermal administration can be presented as discrete patches and can be lipophilic emulsions or buffered, aqueous solutions, dissolved and/or dispersed in a polymer or an adhesive. Transdermal patches may be placed over different portions of the patient's body, including over the eye.

Additional iontophoretic devices that can be used for ocular administration of compounds having the structure of Formula (I) are the Eyegate applicator, created and patented by Optis France S. A., and the Ocuphor™ Ocular iontophoresis system developed Iomed, Inc.

For administration by inhalation, the compounds of Formula (I) are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as rectal gels, rectal foam, rectal aerosols, suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Injectable depot forms may be made by forming microencapsulated matrices (also known as microencapsule matrices) of the compound of Formula (I) in biodegradable polymers. Depending upon the ratio of drug to polymer and the nature of the particular polymer employed, the rate of drug release can be controlled. Depot injectable formulations may be also prepared by entrapping the drug in liposomes or microemulsions. By way of example only, posterior juxtascleral depots may be used as a mode of administration for compounds having the structure of Formula (I). The sclera is a thin avascular layer, comprised of highly ordered collagen network surrounding most of vertebrate eye. Since the sclera is avascular it can be utilized as a natural storage depot from which injected material cannot rapidly removed or cleared from the eye. The formulation used for administration of the compound into the scleral layer of the eye can be any form suitable for application into the sclera by injection through a cannula with small diameter suitable for injection into the scleral layer. Examples for injectable application forms are solutions, suspensions or colloidal suspensions.

A pharmaceutical carrier for the hydrophobic compounds of Formula (I) is a cosolvent system comprising benzyl alcohol, a nonpolar surfactant, a water-miscible organic polymer, and an aqueous phase. The cosolvent system may be a 10% ethanol, 10% polyethylene glycol 300, 10% polyethylene glycol 40 castor oil (PEG-40 castor oil) with 70% aqueous solution. This cosolvent system dissolves hydrophobic compounds well, and itself produces low toxicity upon systemic administration. Naturally, the proportions of a cosolvent system may be varied considerably without destroying its solubility and toxicity characteristics. Furthermore, the identity of the cosolvent components may be varied: for example, other low-toxicity nonpolar surfactants may be used instead of PEG40 castor oil, the fraction size of polyethylene glycol 300 may be varied; other biocompatible polymers may replace polyethylene glycol, e.g., polyvinyl pyrrolidone; and other sugars or polysaccharides maybe included in the aqueous solution.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

One formulation for the administration of compounds having the structure of Formula (I) has been used with fenretinide in the treatment of neuroblastoma, prostate and ovarian cancers, and is marketed by Avanti Polar Lipids, Inc. (Alabaster, Ala.) under the name Lym-X-Sorb™. This formulation, which comprises an organized lipid matrix that includes lysophosphatidylcholine, monoglyceride and fatty acid, is designed to improve the oral availability of fenretinide. Such a formulation, i.e., an oral formulation that includes lysophosphatidylcholine, monoglyceride and fatty acid, is proposed to also provide improved bioavailability of compounds having the structure of Formula (I) for the treatment of ophthalmic and ocular diseases and conditions, including but not limited to the macular degenerations and dystrophies.

All of the formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Many of the compounds of Formula (I) may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Treatment Methods, Dosages and Combination Therapies

The term "mammal" means all mammals including humans. Mammals include, by way of example only, humans, non-human primates, cows, dogs, cats, goats, sheep, pigs, rats, mice and rabbits.

The term "effective amount" as used herein refers to that amount of the compound being administered which will relieve to some extent one or more of the symptoms of the disease, condition or disorder being treated.

The compositions containing the compound(s) described herein can be administered for prophylactic and/or therapeutic treatments. The term "treating" is used to refer to either prophylactic and/or therapeutic treatments. In therapeutic applications, the compositions are administered to a patient already suffering from a disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial).

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more sub-doses per day.

In certain instances, it may be appropriate to administer at least one of the compounds described herein (or a pharmaceutically acceptable salt, ester, amide, prodrug, or solvate) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for macular degeneration involving administration of one of the compounds described herein, increased therapeutic benefit may result by also providing the patient with other therapeutic agents or therapies for macular degeneration. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of at least one compound of formula (I) with nitric oxide (NO) inducers, statins, negatively charged phospholipids, anti-oxidants, minerals, anti-inflammatory agents, anti-angiogenic agents, matrix metalloproteinase inhibitors, and carotenoids. In several instances, suitable combination agents may fall within multiple categories (by way of example only, lutein is an anti-oxidant and a carotenoid). Further, the compounds of Formula (I) may also be administered with additional agents that may provide benefit to the patient, including by way of example only cyclosporin A.

In addition, the compounds of Formula (I) may also be used in combination with procedures that may provide additional or synergistic benefit to the patient, including, by way of example only, the use of extracorporeal rheopheresis (also known as membrane differential filtration), the use of implantable miniature telescopes, laser photocoagulation of drusen, and microstimulation therapy.

The use of anti-oxidants has been shown to benefit patients with macular degenerations and dystrophies. See, e.g., *Arch. Ophthalmol.*, 119: 1417-36 (2001); Sparrow, et al., *J. Biol. Chem.*, 278:18207-13 (2003). Examples of suitable anti-oxidants that could be used in combination with at least one compound having the structure of Formula (I) include vitamin C, vitamin E, beta-carotene and other carotenoids, coenzyme Q, 4-hydroxy-2,2,6,6-tetramethylpiperidine-N-oxyl (also known as Tempol), lutein, butylated hydroxytoluene, resveratrol, a trolox analogue (PNU-83836-E), and bilberry extract.

The use of certain minerals has also been shown to benefit patients with macular degenerations and dystrophies. See, e.g., *Arch. Ophthalmol.*, 119: 1417-36 (2001). Examples of suitable minerals that could be used in combination with at least one compound having the structure of Formula (I) include copper-containing minerals, such as cupric oxide (by way of example only); zinc-containing minerals, such as zinc oxide (by way of example only); and selenium-containing compounds.

The use of certain negatively-charged phospholipids has also been shown to benefit patients with macular degenerations and dystrophies. See, e.g., Shaban & Richter, *Biol. Chem.*, 383:537-45 (2002); Shaban, et al., *Exp. Eye Res.*, 75:99-108 (2002). Examples of suitable negatively charged phospholipids that could be used in combination with at least one compound having the structure of Formula (I) include cardiolipin and phosphatidylglycerol. Positively-charged and/or neutral phospholipids may also provide benefit for patients with macular degenerations and dystrophies when used in combination with compounds having the structure of Formula (I).

The use of certain carotenoids has been correlated with the maintenance of photoprotection necessary in photoreceptor cells. Carotenoids are naturally-occurring yellow to red pigments of the terpenoid group that can be found in plants, algae, bacteria, and certain animals, such as birds and shellfish. Carotenoids are a large class of molecules in which more than 600 naturally occurring carotenoids have been identified. Carotenoids include hydrocarbons (carotenes) and their oxygenated, alcoholic derivatives (xanthophylls). They include actinioerythrol, astaxanthin, canthaxanthin, capsanthin, capsorubin, β-8'-apo-carotenal (apo-carotenal), β-12'-apo-carotenal, α-carotene, β-carotene, "carotene" (a mixture of α- and β-carotenes), γ-carotenes, β-cyrptoxanthin, lutein, lycopene, violerythrin, zeaxanthin, and esters of hydroxyl- or carboxyl-containing members thereof. Many of the carotenoids occur in nature as cis- and trans-isomeric forms, while synthetic compounds are frequently racemic mixtures.

In humans, the retina selectively accumulates mainly two carotenoids: zeaxanthin and lutein. These two carotenoids are thought to aid in protecting the retina because they are powerful antioxidants and absorb blue light. Studies with quails establish that groups raised on carotenoid-deficient diets had retinas with low concentrations of zeaxanthin and suffered severe light damage, as evidenced by a very high number of apoptotic photoreceptor cells, while the group with high zeaxanthin concentrations had minimal damage. Examples of suitable carotenoids for in combination with at least one compound having the structure of Formula (I) include lutein and zeaxanthin, as well as any of the aforementioned carotenoids.

Suitable nitric oxide inducers include compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosine, bradykinin, calreticulin, bisacodyl, and phenolphthalein. EDRF is a vascular relaxing factor secreted by the endothelium, and has been identified as nitric oxide or a closely related derivative thereof (Palmer et al, *Nature*, 327: 524-526 (1987); Ignarro et al, *Proc. Natl. Acad. Sci*. USA, 84:9265-9269 (1987)).

Statins serve as lipid-lowering agents and/or suitable nitric oxide inducers. In addition, a relationship has been demonstrated between statin use and delayed onset or development of macular degeneration. G. McGwin, et al., *British Journal of Ophthalmology*, 87:1121-25 (2003). Statins can thus provide benefit to a patient suffering from an ophthalmic condition (such as the macular degenerations and dystrophies, and the retinal dystrophies) when administered in combination with compounds of Formula (I). Suitable statins include, by way of example only, rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (which is the hemicalcium salt of atorvastatin), and dihydrocompactin.

Suitable anti-inflammatory agents with which the Compounds of Formula (I) may be used include, by way of example only, aspirin and other salicylates, cromolyn, nedocromil, theophylline, zileuton, zafirlukast, montelukast, pranlukast, indomethacin, and lipoxygenase inhibitors; non-steroidal antiinflammatory drugs (NSAIDs) (such as ibuprofen and naproxin); prednisone, dexamethasone, cyclooxygenase inhibitors (i.e., COX-1 and/or COX-2 inhibitors such as Naproxen™, or Celebrex™); statins (by way of example only, rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (which is the hemicalcium salt of atorvastatin), and dihydrocompactin); and disassociated steroids.

Suitable matrix metalloproteinases (MMPs) inhibitors may also be administered in combination with compounds of Formula (I) in order to treat ophthalmic conditions or symptoms associated with macular or retinal degenerations. MMPs are known to hydrolyze most components of the extracellular matrix. These proteinases play a central role in many biological processes such as normal tissue remodeling, embryogenesis, wound healing and angiogenesis. However, excessive expression of MMP has been observed in many disease states, including macular degeneration. Many MMPs have been identified, most of which are multidomain zinc endopeptidases. A number of metalloproteinase inhibitors are known (see for example the review of MMP inhibitors by Whittaker M. et al, *Chemical Reviews* 99(9):2735-2776 (1999)). Representative examples of MMP Inhibitors include Tissue Inhibitors of Metalloproteinases (TIMPs) (e.g., TIMP-1, TIMP-2, TIMP-3, or TIMP-4), $\alpha_2$-macroglobulin, tetracyclines (e.g., tetracycline, minocycline, and doxycycline), hydroxamates (e.g., BATIMASTAT, MARIMISTAT and TROCADE), chelators (e.g., EDTA, cysteine, acetylcysteine, D-penicillamine, and gold salts), synthetic MMP fragments, succinyl mercaptopurines, phosphonamidates, and hydroxaminic acids. Examples of MMP inhibitors that may be used in combination with compounds of Formula (I) include, by way of example only, any of the aforementioned inhibitors.

The use of antiangiogenic or anti-VEGF drugs has also been shown to provide benefit for patients with macular degenerations and dystrophies. Examples of suitable antiangiogenic or anti-VEGF drugs that could be used in combination with at least one compound having the structure of Formula (I) include Rhufab V2 (Lucentis™), Tryptophanyl-tRNA synthetase (TrpRS), Eye001 (Anti-VEGF Pegylated Aptamer), squalamine, Retaane™ 15 mg (anecortave acetate for depot suspension; Alcon, Inc.), Combretastatin A4 Prodrug (CA4P), Macugen™, Mifeprex™ (mifepristone—ru486), subtenon triamcinolone acetonide, intravitreal crystalline triamcinolone acetonide, Prinomastat (AG3340—synthetic matrix metalloproteinase inhibitor, Pfizer), fluocinolone acetonide (including fluocinolone intraocular implant, Bausch & Lomb/Control Delivery Systems), VEGFR inhibitors (Sugen), and VEGF-Trap (Regeneron/Aventis).

Other pharmaceutical therapies that have been used to relieve visual impairment can be used in combination with at least one compound of Formula (I). Such treatments include but are not limited to agents such as Visudyne™ with use of a non-thermal laser, PKC 412, Endovion (NeuroSearch A/S), neurotrophic factors, including by way of example Glial Derived Neurotrophic Factor and Ciliary Neurotrophic Factor, diatazem, dorzolamide, Phototrop, 9-cis-retinal, eye medication (including Echo Therapy) including phospholine iodide or echothiophate or carbonic anhydrase inhibitors, AE-941 (AEterna Laboratories, Inc.), Sirna-027 (Sirna Therapeutics, Inc.), pegaptanib (NeXstar Pharmaceuticals/Gilead Sciences), neurotrophins (including, by way of example only, NT-4/5, Genentech), Cand5 (Acuity Pharmaceuticals), ranibizumab (Genentech), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (Allergan, SUGEN, Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), and cyclosporin A. See U.S. Patent Application Publication No. 20040092435.

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; we envision the use of multiple therapeutic combinations. By way of example only, a compound having the structure of Formula (I) may be provided with at least one antioxidant and at least one negatively charged phospholipid; or a compound having the structure of Formula (I) may be provided with at least one antioxidant and at least one inducer of nitric oxide production; or a compound having the structure of Formula (I) may be provided with at least one inducer of nitric oxide productions and at least one negatively charged phospholipid; and so forth.

In addition, the compounds of Formula (I) may also be used in combination with procedures that may provide additional or synergistic benefit to the patient. Procedures known, proposed or considered to relieve visual impairment include but are not limited to 'limited retinal translocation', photodynamic therapy (including, by way of example only, receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; motexafin lutetium, Pharmacyclics, Inc.), antisense oligonucleotides (including, by way of example, products tested by Novagali Pharma SA and ISIS-13650, Isis Pharmaceuticals), laser photocoagulation, drusen lasering, macular hole surgery, macular translocation surgery, implantable miniature telescopes, Phi-Motion Angiography (also known as Micro-Laser Therapy and Feeder Vessel Treatment), Proton Beam Therapy, microstimulation therapy, Retinal Detachment and Vitreous Surgery, Scleral Buckle, Submacular Surgery, Transpupillary Thermotherapy, Photosystem I therapy, use of RNA interference (RNAi), extracorporeal rheopheresis (also known as membrane differential filtration and Rheotherapy), microchip implantation, stem cell therapy, gene replacement therapy, ribozyme gene therapy (including gene therapy for hypoxia response element, Oxford Biomedica; Lentipak, Genetix; PDEF gene therapy, GenVec), photoreceptor/retinal cells transplantation (including transplantable retinal epithelial cells, Diacrin, Inc.; retinal cell transplant, Cell Genesys, Inc.), and acupuncture.

Further combinations that may be used to benefit an individual include using genetic testing to determine whether that individual is a carrier of a mutant gene that is known to be correlated with certain ophthalmic conditions. By way of example only, defects in the human ABCA4 gene are thought to be associated with five distinct retinal phenotypes including Stargardt disease, cone-rod dystrophy, age-related macular degeneration and retinitis pigmentosa. See e.g., Allikmets et al., *Science*, 277:1805-07 (1997); Lewis et al., *Am. J. Hum. Genet.*, 64:422-34 (1999); Stone et al., *Nature Genetics*, 20:328-29 (1998); Allikmets, *Am. J Hum. Gen.*, 67:793-799 (2000); Klevering, et al, *Ophthalmology*, 11 1:546-553 (2004). In addition, an autosomal dominant form of Stargardt Disease is caused by mutations in the ELOV4 gene. See Karan, et al., *Proc. Natl. Acad. Sci.* (2005). Patients possessing any of these mutations are expected to find therapeutic and/or prophylactic benefit in the methods described herein.

Synthesis of the Compounds of Formula (I)

Compounds of Formula (I) may be synthesized using standard synthetic techniques known to those of skill in the art or using methods known in the art in combination with methods described herein. See, e.g., U.S. Patent Application Publication 2004/0102650; Um, S. J., et al., *Chem. Pharm. Bull.*, 52:501-506 (2004). In addition, several of the compounds of Formula (I), such as fenretinide, may be purchased from various commercial suppliers. As a further guide the following synthetic methods may also be utilized.

Formation of Covalent Linkages by Reaction of an Electrophile with a Nucleophile Selected examples of covalent linkages and precursor functional groups which yield them are given in the Table entitled "Examples of Covalent Linkages and Precursors Thereof." Precursor functional groups are shown as electrophilic groups and nucleophilic groups. The functional group on the organic substance may be attached directly, or attached via any useful spacer or linker as defined below.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Suitable carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage of being kinetically stable in water or polar organic solvents. Other carbori nucleophiles include phosphorus ylids, enol and enolate reagents; these carbon nucleophiles have the advantage of being relatively easy to generate from precursors well known to those skilled in the art of synthetic organic chemistry. Carbon nucleophiles, when used in conjunction with carbon electrophiles, engender new carbon-carbon bonds between the carbon nucleophile and carbon electrophile.

Non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a hetereoatom, e.g., oxygen or nitrogen.

Use of Protecting Groups

The term "protecting group" refers to chemical moieties that block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester derivatives as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd_0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

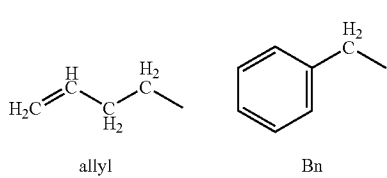

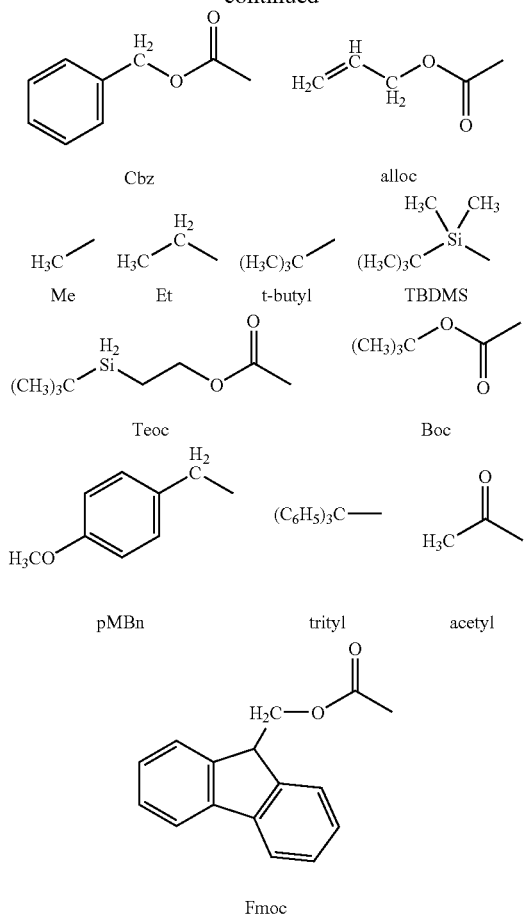

Other protecting groups are described in Greene and Wuts, Protective Groups in Organic Synthesis, 3rd Ed., John Wiley & Sons, New York, N.Y., 1999, which is incorporated herein by reference in its entirety.

Illustrative Examples

The following examples provide illustrative methods for testing the effectiveness and safety of the compounds of Formula (I). These examples are provided for illustrative purposes only and not to limit the scope of the claims provided herein.

Human Studies

Detection of Macular or Retinal Degeneration. Identification of abnormal blood vessels in the eye can be done with an angiogram. This identification can help determine which patients are candidates for the use of a candidate substance or other treatment method to hinder or prevent further vision loss. Angiograms can also be useful for follow-up of treatment as well as for future evaluation of any new vessel growth.

A fluorescein angiogram (fluorescein angiography, fluorescein angioscopy) is a technique for the visualization of choroidal and retinal circulation at the back of the eye. Fluorescein dye is injected intravenously followed by multiframe photography (angiography), ophthalmoscopic evaluation (angioscopy), or by a Heidelberg retina angiograph (a confocal scanning laser system). Additionally, the retina can be examined by OCT, a non-invasive way to obtain high-resolution cross-sectional images of the retina. Fluorescein angiograms are used in the evaluation of a wide range of retinal and choroidal diseases through the analysis of leakage or possible damage to the blood vessels that feed the retina. It has also been used to evaluate abnormalities of the optic nerve and iris by Berkow et al., *Am. J. Ophthalmol.* 97:143-7 (1984).

Similarly, angiograms using indocyanine green can be used for the visualization circulation at the back of the eye. Wherein fluorescein is more efficient for studying retinal circulation, indocyanine is better for observing the deeper choroidal blood vessel layer. The use of indocyanine angiography is helpful when neovascularization may not be observed with fluorescein dye alone.

Appropriate human doses for compounds having the structure of Formula (I) will be determined using a standard dose escalation study. However, some guidance is available from studies on the use of such compounds in the treatment of cancer. For example, a 4800 mg/m$^2$ dose of fenretinide, which is a compound having the structure of Formula (I), has been administered to patients with a variety of cancers. Such doses were administered three times daily and observed toxicities were minimal. However, the recommended dose for such patients was 900 mg/m$^2$ based on an observed ceiling on achievable plasma levels. In addition, the bioavailability of fenretinide is increased with meals, with the plasma concentration being three times greater after high fat meals than after carbohydrate meals.

The observation of occasional night blindness in humans suggests to us significant impairment of rhodopsin regeneration at normal therapeutic doses. Based on these data, we propose that inhibitory concentrations of fenretinide in RPE tissue is achieved at doses similar to, or possibly below, human therapeutic doses for the treatment of cancer.

EXAMPLE 1

Testing for the Efficacy of Compounds of Formula (I) to Treat Macular Degeneration For pre-testing, all human patients undergo a routine ophthalmologic examination including fluorescein angiography, measurement of visual acuity, electrophysiologic parameters and biochemical and rheologic parameters. Inclusion criteria are as follows: visual acuity between 20/160 and 20/32 in at least one eye and signs of AMD such as drusen, areolar atrophy, pigment clumping, pigment epithelium detachment, or subretinal neovascularization. Patients that are pregnant or actively breast-feeding children are excluded from the study.

Two hundred human patients diagnosed with macular degeneration, or who have progressive formations of A2E, lipofuscin, or drusen in their eyes are divided into a control group of about 100 patients and an experimental group of 100 patients. Fenretinide is administered to the experimental group on a daily basis. A placebo is administered to the control group in the same regime as fenretinide is administered to the experimental group.

Administration of fenretinide or placebo to a patient can be either orally or parenterally administered at amounts effective to inhibit the development or reoccurrence of macular degeneration. Effective dosage amounts are in the range of from about 1-4000 mg/m$^2$ up to three times a day.

One method for measuring progression of macular degeneration in both control and experimental groups is the best corrected visual acuity as measured by Early Treatment Diabetic Retinopathy Study (ETDRS) charts (Lighthouse, Long Island, N.Y.) using line assessment and the forced choice method (Ferris et al. *Am J Ophthalmol*, 94:97-98 (1982)). Visual acuity is recorded in logMAR. The change of one line on the ETDRS chart is equivalent to 0.1 logMAR. Further typical methods for measuring progression of macular degeneration in both control and experimental groups include use of visual field examinations, including but not limited to a Humphrey visual field examination, and measuring/monitoring the autofluorescence or absorption spectra of N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine in the eye of the patient. Autofluorescence is measured using a variety of equipment, including but not limited to a confocal scanning laser ophthalmoscope. See Bindewald, et al., *Am. J. Ophthalmol.*, 137: 556-8 (2004).

Additional methods for measuring progression of macular degeneration in both control and experimental groups include taking fundus photographs, observing changes in autofluorescence over time using a Heidelberg retina angiograph (or alternatively, techniques described in M. Hammer, et al. *Ophthalmologe* 2004 Apr. 7 [Epub ahead of patent]), and taking fluorescein angiograms at baseline, three, six, nine and twelve months at follow-up visits. Documentation of morphologic changes include changes in (a) drusen size, character, and distribution; (b) development and progression of choroidal neovascularization; (c) other interval fundus changes or abnormalities; (d) reading speed and/or reading acuity; (e) scotoma size; or (f) the size and number of the geographic atrophy lesions. In addition, Amsler Grid Test and color testing are optionally administered.

To assess statistically visual improvement during drug administration, examiners use the ETDRS (LogMAR) chart and a standardized refraction and visual acuity protocol. Evaluation of the mean ETDRS (LogMAR) best corrected visual acuity (BCVA) from baseline through the available post-treatment interval visits can aid in determining statistical visual improvement.

To assess the ANOVA (analysis of variance between groups) between the control and experimental group, the mean changes in ETDRS (LogMAR) visual acuity from baseline through the available post-treatment interval visits are compared using two-group ANOVA with repeated measures analysis with unstructured covariance using SAS/STAT Software (SAS Institutes Inc, Cary, N.C.).

Toxicity evaluation after the commencement of the study include check ups every three months during the subsequent year, every four months the year after and subsequently every six months. Plasma levels of fenretinide and its metabolite N-(4-methoxyphenyl)-retinamide can also be assessed during these visits. The toxicity evaluation includes patients using fenretinide as well as the patients in the control group.

EXAMPLE 2

Testing for the Efficacy of Compounds of Formula (I) to Reduce A2E Production

The same protocol design, including pre-testing, administration, dosing and toxicity evaluation protocols, that are described in Example 1 are also used to test for the efficacy of compounds of Formula (I) in reducing or otherwise limiting the production of A2E in the eye of a patient.

Methods for measuring or monitoring formation of A2E include the use of autofluorescence measurements of N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine in the eye of the patient.

Autofluorescence is measured using a variety of equipment, including but not limited to a confocal scanning laser ophthalmoscope, see Bindewald, et al., *Am. J. Ophthalmol.*, 137: 556-8 (2004), or the autofluorescence or absorption spectra measurement techniques noted in Example 1. Other tests that can be used as surrogate markers for the efficacy of a particular treatment include the use of visual acuity and visual field examinations, reading speed and/or reading acuity examinations, measurements on the size and number of scotoma and/or geographic atrophic lesions, as described in Example 1. The statistical analyses described in Example 1 is employed.

EXAMPLE 3

Testing for the Efficacy of Compounds of Formula (I) to Reduce Lipofuscin Production The same protocol design, including pre-testing, administration, dosing and toxicity evaluation protocols that are described in Example 1 are also used to test for the efficacy of compounds of Formula (I) in reducing or otherwise limiting the production of lipofuscin in the eye of a patient. The statistical analyses described in Example 1 may also be employed.

Tests that can be used as surrogate markers for the efficacy of a particular treatment include the use of visual acuity and visual field examinations, reading speed and/or reading acuity examinations, measurements on the size and number of scotoma and/or geographic atrophic lesions, and the measuring/monitoring of autofluorescence of certain compounds in the eye of the patient, as described in Example 1.

EXAMPLE 4

Testing for the Efficacy of Compounds of Formula (I) to Reduce Drusen Production The same protocol design, including pre-testing, administration, dosing and toxicity evaluation protocols, that are described in Example 1 are also used to test for the efficacy of compounds of Formula (I) in reducing or otherwise limiting the production or formation of drusen in the eye of a patient. The statistical analyses described in Example 1 may also be employed.

Methods for measuring progressive formations of drusen in both control and experimental groups include taking fundus photographs and fluorescein angiograms at baseline, three, six, nine and twelve months at follow-up visits. Documentation of morphologic changes may include changes in (a) drusen size, character, and distribution (b) development and progression of choroidal neovascularization and (c) other interval fundus changes or abnormalities. Other tests that can be used as surrogate markers for the efficacy of a particular treatment include the use of visual acuity and visual field examinations, reading speed and/or reading acuity examinations, measurements on the size and number of scotoma and/or geographic atrophic lesions, and the measuring/monitoring of autofluorescence of certain compounds in the eye of the patient, as described in Example 1.

EXAMPLE 5

Genetic Testing for Macular Dystrophies

Defects in the human ABCA4 gene are thought to be associated with five distinct retinal phenotypes including Stargardt Disease, cone-rod dystrophy, age-related macular degeneration (both dry form and wet form) and retinitis pigmentosa. See e.g., Allikmets et al., *Science*, 277:1805-07 (1997); Lewis et al., *Am. J. Hum. Genet.*, 64:422-34 (1999); Stone et al., *Nature Genetics*, 20:328-29 (1998); Allikmets, *Am. J. Hum. Gen.*, 67:793-799 (2000); Klevering, et al, *Ophthalmology*, 111:546-553 (2004). In addition, an autosomal dominant form of Stargardt Disease is caused by mutations in the ELOV4 gene. See Karan, et al., *Proc. Natl. Acad. Sci.* (2005). Patients can be diagnosed as having Stargardt Disease by any of the following assays:

A direct-sequencing mutation detection strategy which can involve sequencing all exons and flanking intron regions of ABCA4 or ELOV4 for sequence mutation(s);
  Genomic Southern analysis;
  Microarray assays that include all known ABCA4 or ELOV4 variants; and
  Analysis by liquid chromatography tandem mass spectrometry coupled with immunocytochemical analysis using antibodies and Western analysis.

Fundus photographs, fluorescein anigograms, and scanning laser ophthalmoscope imaging along with the history of the patient and his or her family can anticipate and/or confirm diagnosis.

Mice and Rat Studies

The optimal dose of compounds of Formula (I) to block formation of A2E in abca4$^{-/-}$ mice can be determined using a standard dose escalation study. One illustrative approach, utilizing fenretinide, which is a compound having the structure of Formula (I) is presented below. However, similar approaches may be utilized for other compounds having the structure of Formula (I).

The effects of fenretinide on all-trans-retinal in retinas from light-adapted mice would preferably be determined at doses that bracket the human therapeutic dose. The preferred method includes treating mice with a single morning intraperitoneal dose. An increased frequency of injections may be required to maintain reduced levels of all-trans-retinal in the retina throughout the day.

ABCA4 Knockout Mice. ABCA4 encodes rim protein (RmP), an ATP-binding cassette (ABC) transporter in the outer-segment discs of rod and cone photoreceptors. The transported substrate for RmP is unknown. Mice generated with a knockout mutation in the abca4 gene, see Weng et al., *Cell*, 98:13-23 (1999), are useful for the study of RmP function as well as for an in vivo screening of the effectiveness for candidate substances. These animals manifest the complex ocular phenotype: (i) slow photoreceptor degeneration, (ii) delayed recovery of rod sensitivity following light exposure, (iii) elevated atRAL and reduced atROL in photoreceptor outer-segments following a photobleach, (iv) constitutively elevated phosphatidylethanolamine (PE) in outer-segments, and (v) accumulation of lipofuscin in RPE cells. See Weng et al., *Cell*, 98:13-23 (1999).

Rates of photoreceptor degeneration can be monitored in treated and untreated wild-type and abca4$^{-/-}$ mice by two techniques. One is the study of mice at different times by ERG analysis and is adopted from a clinical diagnostic procedure. See Weng et al., *Cell*, 98:13-23 (1999). An electrode is placed on the corneal surface of an anesthetized mouse and the electrical response to a light flash is recorded from the retina. Amplitude of the α-wave, which results from light-induced hyperpolarization of photoreceptors, is a sensitive indicator of photoreceptor degeneration. See Kedzierski et al., *Invest. Ophthalmol. Vis. Sci.*, 38:498-509 (1997). ERGs are done on live animals. The same mouse can therefore be analyzed repeatedly during a time-course study. The definitive technique for quantitating photoreceptor degeneration is histological analysis of retinal sections. The number of photoreceptors remaining in the retina at each time point will be determined by counting the rows of photoreceptor nuclei in the outer nuclear layer.

Tissue Extraction. Eye samples were thawed on ice in 1 ml of PBS, pH 7.2 and homogeriized by hand using a Duall glass-glass homogenizer. The sample was further homogenized following the addition of 1 ml chloroform/methanol (2:1, v/v). The sample was transferred to a borosclicate tube and lipids were extracted into 4 mls of chloroform. The organic extract was washed with 3 mls PBS, pH 7.2 and the samples were then centrifuged at 3,000× g, 10 min. The choloroform phase was decanted and the aqueous phase was re-extracted with another 4 mls of chloroform. Following centrifugation, the chloroform phases were combined and the samples were taken to dryness under nitrogen gas. Samples residues were resuspended in 100 µl hexane and analyzed by HPLC as described below.

HPLC Analysis. Chromatographic separations were achieved on an Agilent Zorbax Rx-Sil Column (5 µm, 4.6× 250 mm) using an Agilent 1100 series liquid chromatograph equipped with fluorescence and diode array detectors. The mobile phase (hexane/2-propanol/ethanol/25 mM $KH_2PO_4$. pH 7.0/acetic acid; 485/376/100/50/0.275, v/v) was delivered at 1 ml/min. Sample peak identification was made by comparison to retention time and absorbance spectra of authentic standards. Data are reported as peak fluorescence (L.U.) obtained from the fluorescence detector.

EXAMPLE 6

Effect of Fenretinide on A2E Accumulation

Administration of fenretinide to an experimental group of mice and administration of DMSO alone to a control group of mice is performed and assayed for accumulation of A2E. The experimental group is given 2.5 to 20 mg/kg of fenretinide per day in 10 to 25 µl of DMSO. Higher dosages are tested if no effect is seen with the highest dose of 50 mg/kg. The control group is given 10 to 25 µl injections of DMSO alone. Mice are administered either experimental or control substances by intraperitoneal (i.p.) injection for various experimental time periods not to exceed one month.

To assay for the accumulation of A2E in abca4$^{-/-}$ mice RPE, 2.5 to 20 mg/kg of fenretinide is provided by i.p. injection per day to 2-month old abca4$^{-/-}$ mice. After 1 month, both experimental and control mice are killed and the levels of A2E in the RPE are determined by HPLC. In addition, the autofluorescence or absorption spectra of N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine may be monitored using a UV/Vis spectrophotometer.

EXAMPLE 7

Effect of Fenretinide on Lipofuscin Accumulation

Administration of fenretinide to an experimental group of mice and administration of DMSO alone to a control group of mice is performed and assayed for the accumulation of lipofuscin. The experimental group is given 2.5 to 20 mg/kg of fenretinide per day in 10 to 25 µl of DMSO. Higher dosages are tested if no effect is seen with the highest dose of 50 mg/kg. The control group are given 10 to 25 µl injections of DMSO alone. Mice are administered either experimental or control substances by i.p. injection for various experimental time periods not to exceed one month. Alternatively, mice can be implanted with a pump which delivers either experimental or control substances at a rate of 0.25 µl/hr for various experimental time periods not to exceed one month.

To assay for the effects of fenretinide on the formation of lipofuscin in fenretinide treated and untreated abca4$^{-/-}$ mice, eyes can be examined by electron or fluorescence microscopy.

EXAMPLE 8

Effect of Fenretinide on Rod Cell Death or Rod Functional Impairment

Administration of fenretinide to an experimental group of mice and administration of DMSO alone to a control group of mice is performed and assayed for the effects of fenretinide on rod cell death or rod functional impairment. The experimental group is given 2.5 to 20 mg/kg of fenretinide per day in 10 to 25 µl of DMSO. Higher dosages are tested if no effect is seen with the highest dose of 50 mg/kg. The control group is given 10 to 25 µl injections of DMSO alone. Mice are administered either experimental or control substances by i.p. injection for various experimental time periods not to exceed one month. Alternatively, mice can be implanted with a pump which delivers either experimental or control substances at a rate of 0.25 µl/hr for various experimental time periods not to exceed one month.

Mice that are treated to 2.5 to 20 mg/kg of fenretinide per day for approximately 8 weeks can be assayed for the effects of fenretinide on rod cell death or rod functional impairment by monitoring ERG recordings and performing retinal histology.

EXAMPLE 9

Testing for Protection from Light Damage

The following study is adapted from Sieving, P. A., et al, *Proc. Natl. Acad. Sci.*, 98:1835-40 (2001). For chronic light-exposure studies, Sprague-Dawley male 7-wk-old albino rats are housed in 12:12 h light/dark cycle of 5 lux fluorescent white light. Injections of 20-50 mg/kg fenretinide by i.p. injection in 0.18 ml DMSO are given three times daily to chronic rats for 8 wk. Controls receive 0.18 ml DMSO by i.p. injection. Rats are killed 2 d after final injections. Higher dosages are tested if no effect is seen with the highest dose of 50 mg/kg.

For acute light-exposure studies, rats are dark-adapted overnight and given a single i.p. injection of fenretinide 20-50 mg/kg in 0.18 ml DMSO under dim red light and kept in darkness for 1 h before being exposed to the bleaching light before ERG measurements. Rats exposed to 2,000 lux white fluorescent light for 48 h. ERGs are recorded 7 d later, and histology is performed immediately.

Rats are euthanized and eyes are removed. Column cell counts of outer nuclear layer thickness and rod outer segment (ROS) length are measured every 200 µm across both hemispheres, and the numbers are averaged to obtain a measure of cellular changes across the entire retina. ERGs are recorded from chronic rats at 4 and 8 wks of treatment. In acute rodents, rod recovery from bleaching light is tracked by dark-adapted ERGs by using stimuli that elicit no cone contribution. Cone recovery is tracked with photopic ERGs. Prior to ERGs, animals are prepared in dim red light and anaesthetized. Pupils are dilated and ERGs are recorded from both eyes simultaneously by using gold-wire corneal loops.

EXAMPLE 10

Combination Therapy Involving Fenretinide and Accutane

Mice and/or rats are tested in the manner described in Examples 6-9, but with an additional two arms. In one of the additional arms, groups of mice and/or rats are treated with increasing doses of Accutane, from 5 mg/kg per day to 50 mg/kg per day. In the second additional arm, groups of mice and/or rats are treated with a combination of 20 mg/kg per day of fenretinide and increasing doses of Accutane, from 5 mg/kg per day to 50 mg/kg per day. The benefits of the combination therapy are assayed as described in Examples 6-9.

EXAMPLE 11

Efficacy of Fenretinide on the Accumulation of Lipofuscin (and/or A2E) in abca4 Null Mutant Mice: Phase I—Dose Response and Effect on Serum Retinol The effect of HPR on reducing serum retinol in animals and human subjects led us to explore the possibility that reductions in lipofuscin and the toxic bis-retinoid conjugate, A2E, may also be realized. The rationale for this approach is based upon two independent lines of scientific evidence: 1) reduction in ocular vitamin A concentration via inhibition of a known visual cycle enzyme (11-cis retinol dehydrogenase) results in profound reductions in lipofuscin and A2E; 2) animals maintained on a vitamin A deficient diet demonstrate dramatic reductions in lipofuscin accumulation. Thus, the objective for this example was to examine the effect of HPR in an animal model which demonstrates massive accumulation of lipofuscin and A2E in ocular tissue, the abca4 null mutant mouse.

Figure 11:
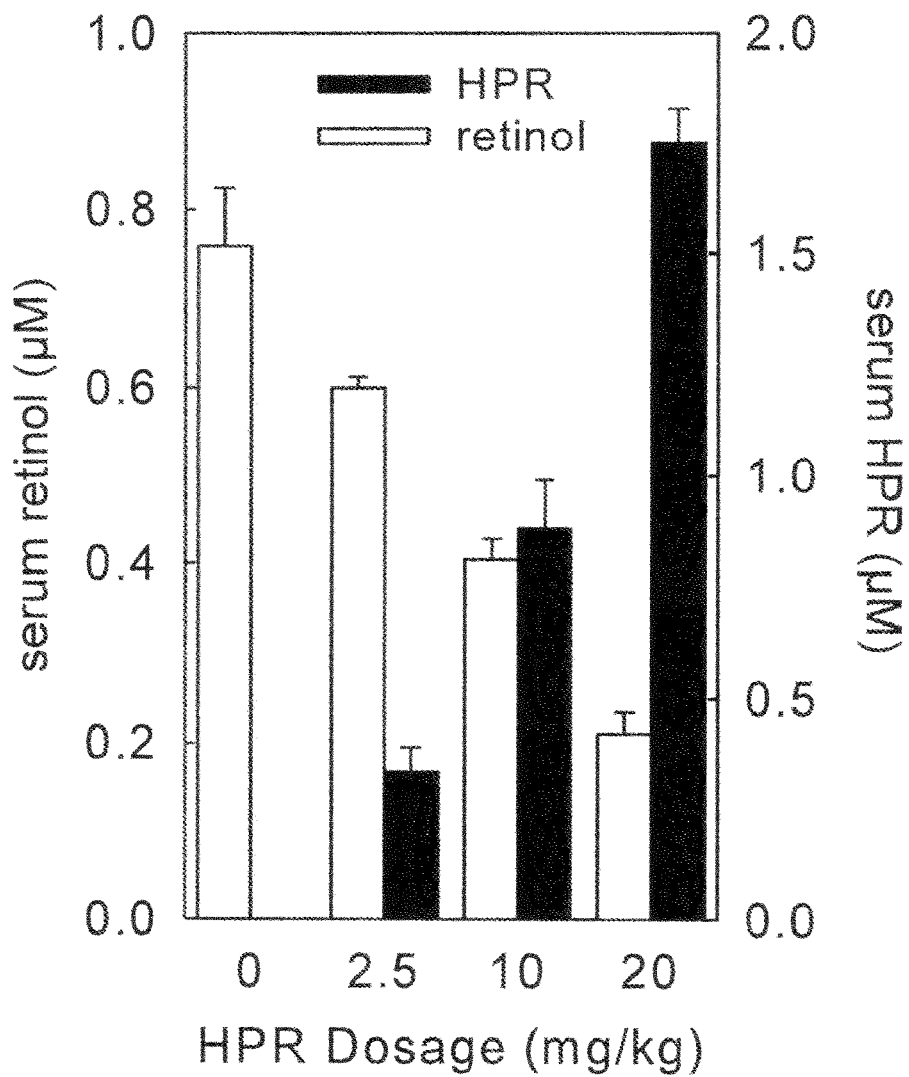
FIG. 11 illustrates the analysis of serum retinol as a function of fenretinide concentration.

Initial studies began by examining the effect of HPR on serum retinol. Animals were divided into three groups and given either DMSO, 10 mg/kg HPR, or 20 mg/kg HPR for 14 days. At the end of the study period, blood was collected from the animals, sera were prepared and an acetonitrile extract of the serum was analyzed by reverse phase LC/MS. UV-visible spectral and mass/charge analyses were performed to confirm the identity of the eluted peaks. Sample chromatograms obtained from these analyses are shown: FIG. 1a.—extract from an abca4 null mutant mouse receiving HPR vehicle, DMSO; FIG. 1b.—10 mg/kg HPR; FIG. 1c.—20 mg/kg HPR. The data clearly show a dose-dependent reduction in serum retinol. Quantitative data indicate that at 10 mg/kg HPR, all-trans retinol is decreased 40%, see FIG. 11. For 20 mg/kg HPR, serum retinol is decreased 72%, see FIG. 11. The steady state concentrations of retinol and HPR in serum (at 20 mg/kg HPR) were determined to be 2.11 µM and 1.75 µM, respectively.

Figure 3A:
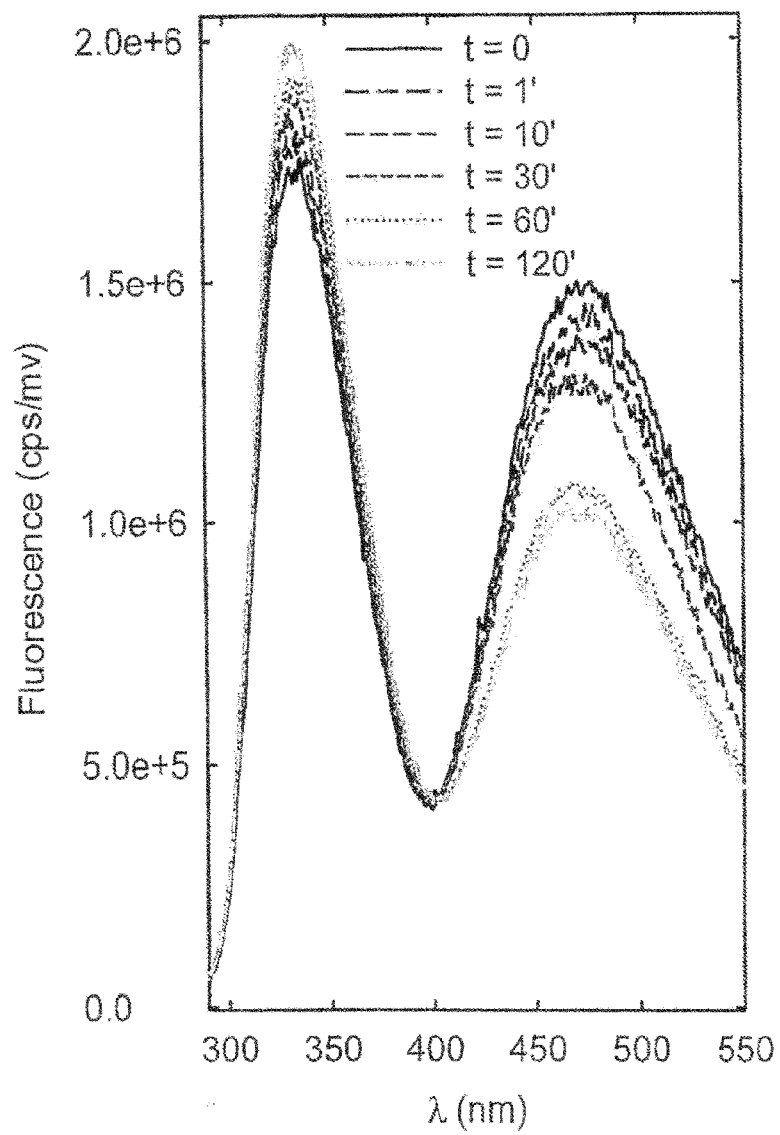
FIG. 3a illustrates a control binding assay for the interaction between retinol and retinol-binding protein as measured by fluorescence quenching.
Figure 3B:
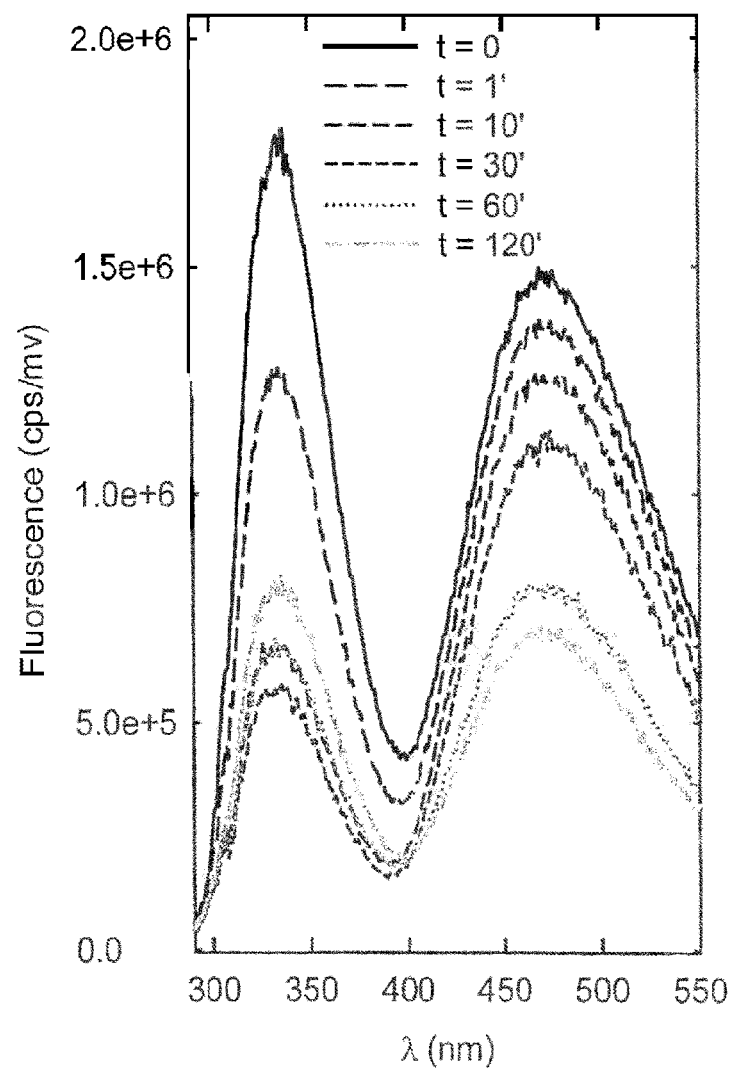
FIG. 3b illustrates a binding assay for the interaction between retinol and retinol-binding protein in the presence of HPR (2 µM) as measured by fluorescence quenching.

Based upon these findings, we sought to further explore the mechanism(s) of retinol reduction during HPR treatment. A tenable hypothesis is that HPR may displace retinol by competing at the retinol binding site on RBP. Like retinol, HPR will absorb (quench) light energy in the region of protein fluorescence; however, unlike retinol, HPR does not emit fluorescence. Therefore, one can measure displacement of retinol from the RBP holoprotein by observing decreases in both protein (340 nm) and retinol (470 nm) fluorescence. We performed a competition binding assay using RBP-retinol/HPR concentrations which were similar to those determined from the 14 day trial at 20 mg/kg HPR described above. Data obtained from these analyses reveal that HPR efficiently displaces retinol from the RBP-retinol holoprotein at physiological temperature, see FIG. 3b. The competitive binding of HPR to RBP was dose-dependent and saturable. In the control assays, decreases in retinol fluorescence were associated with concomitant increases in protein fluorescence, see FIG. 3a. This effect was determined to be due to temperature effects as the dissociation constant of RBP-retinol increases (decreased affinity) with increased time at 37C. In summary, these data suggest that increases of HPR beyond equimolar equivalents, relative to RBP holoprotein (e.g., 1.0 µM HPR, 0.5 µM RBP), will cause a significant fraction of retinol to be displaced from RBP in vivo.

EXAMPLE 12

Efficacy of Fenretinide on the Accumulation of Lipofuscin (and/or A2E) in abca4 Null Mutant Mice: Phase II—Chronic Treatment of abca4 Null Mutant Mice.

Figure 4A:
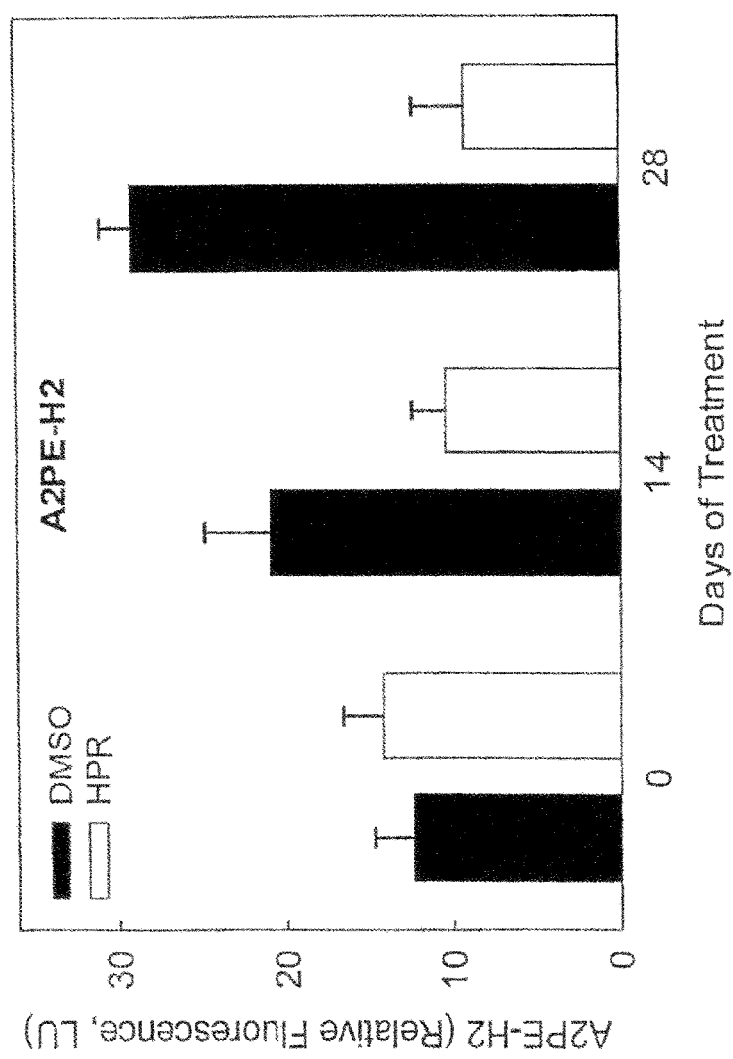
FIG. 4a illustrates the effect of HPR on A2PE-$H_2$ biosynthesis in abca4 null mutant mice.
Figure 4B:
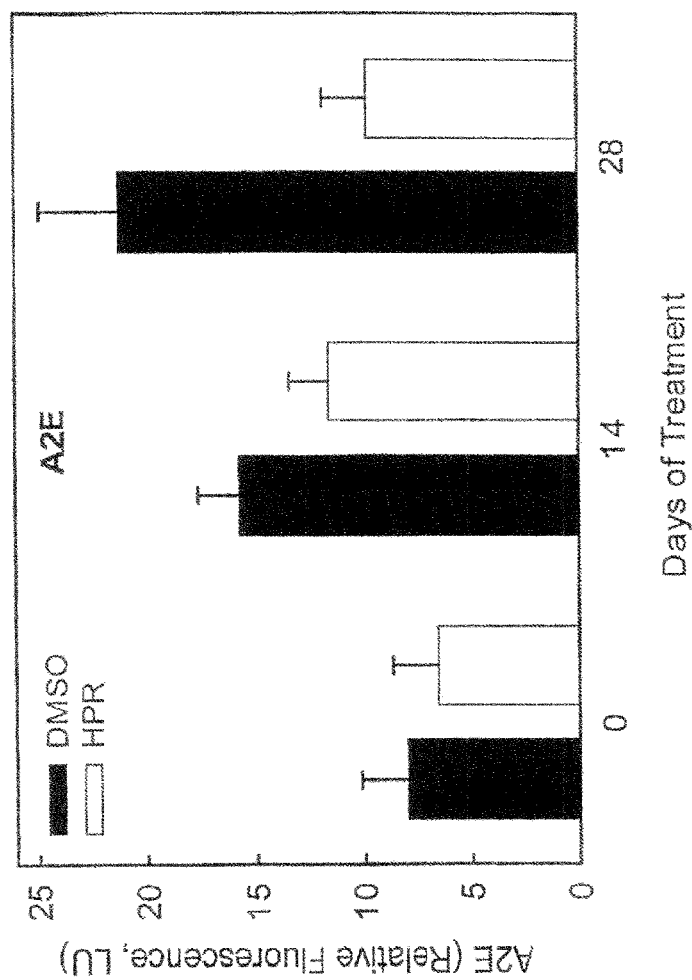
FIG. 4b illustrates the effect of HPR on A2E biosynthesis in abca4 null mutant mice.

We initiated a one-month study to evaluate the effects of HPR on reduction of A2E and A2E precursors in abca4 null mutant mice. HPR was administered in DMSO (20 mg/kg, ip) to abca4 null mutant mice (BL6/129, aged 2 months) daily for a period of 28 days. Control age/strain matched mice received only the DMSO vehicle. Mice were sampled at 0, 14, and 28 days (n=3 per group), the eyes were enucleated and chloroform-soluble constituents (lipids, retinoids and lipid-retinoid conjugates) were extracted. Mice were sacrificed by cervical dislocation, the eyes were enucleated and individually snap frozen in cryo vials. The sample extracts were then analyzed by HPLC with on-line fluorescence detection. Results from this study show remarkable, early reductions in the A2E precursor, A2PE-H2, see FIG. 4a, and subsequent reductions in A2E, see FIG. 4b. Ouantitative analysis revealed a 70% reduction of A2PE-H2 and 55% reduction of A2E following 28 days of HPR treatment. A similar study may be undertaken to ascertain effects of HPR treatment on the electroretinographic and morphological phenotypes.

EXAMPLE 13

Figure 5:
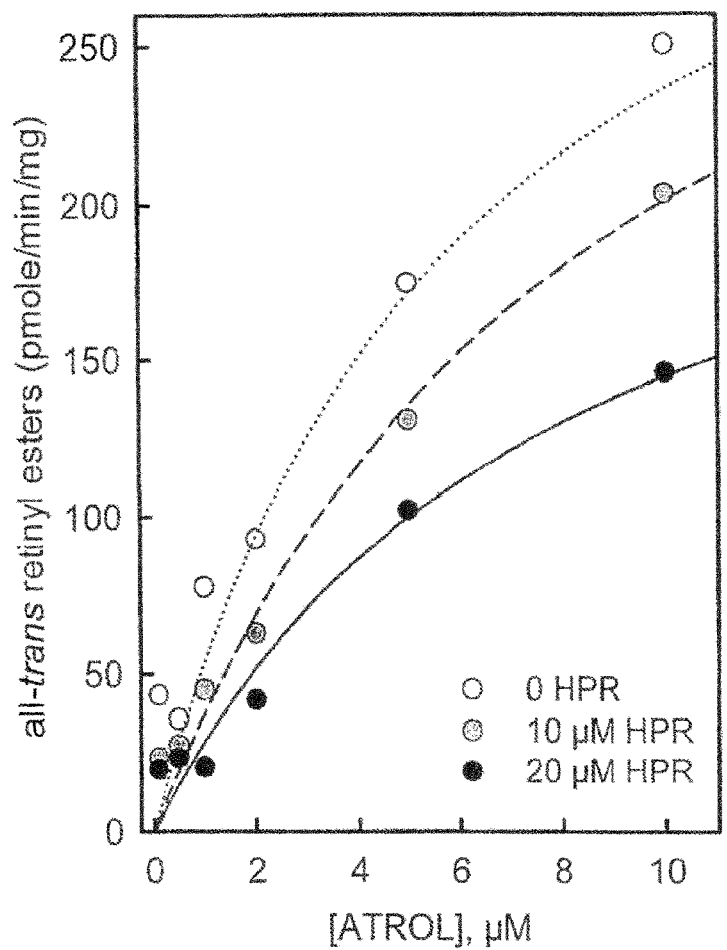
FIG. 5 illustrates the effect of HPR dosage on LRAT activity in the RPE using an in vitro biochemical assay.
Figure 6A:
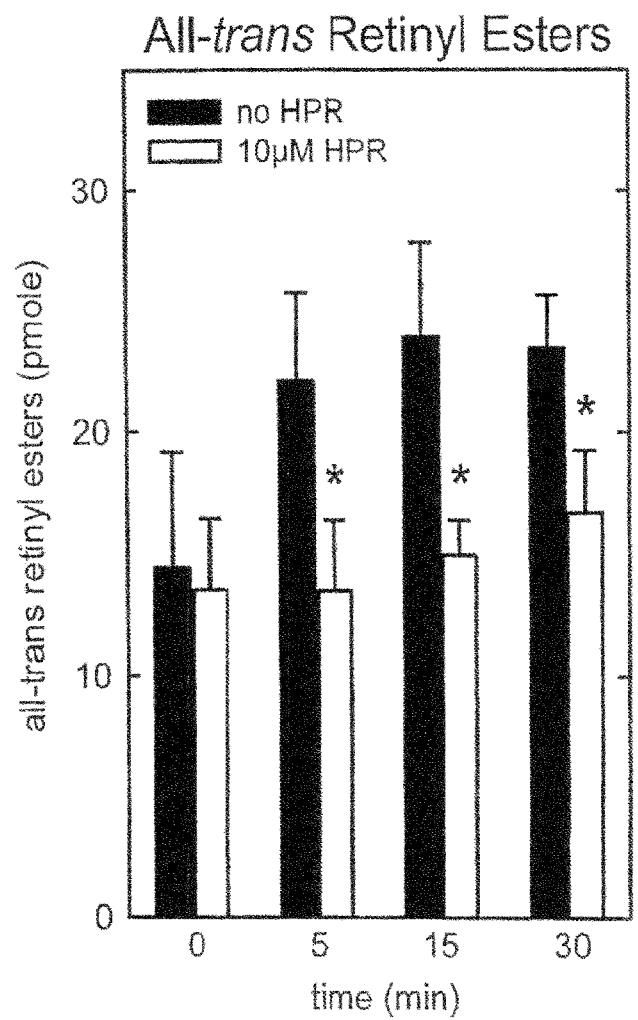
FIG. 6a illustrates the effect of HPR on all-trans retinyl ester biosynthesis using an in vitro biochemical assay.
Figure 6B:
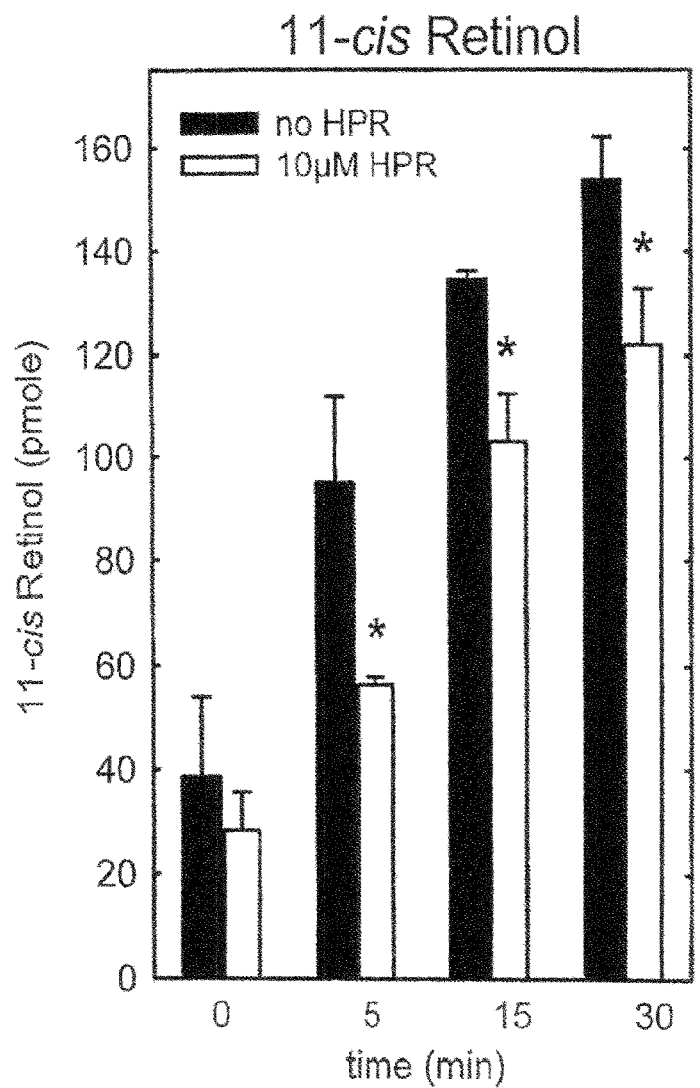
FIG. 6b illustrates the effect of HPR on 11-cis retinol biosynthesis using an in vitro biochemical assay.
Figure 6C:
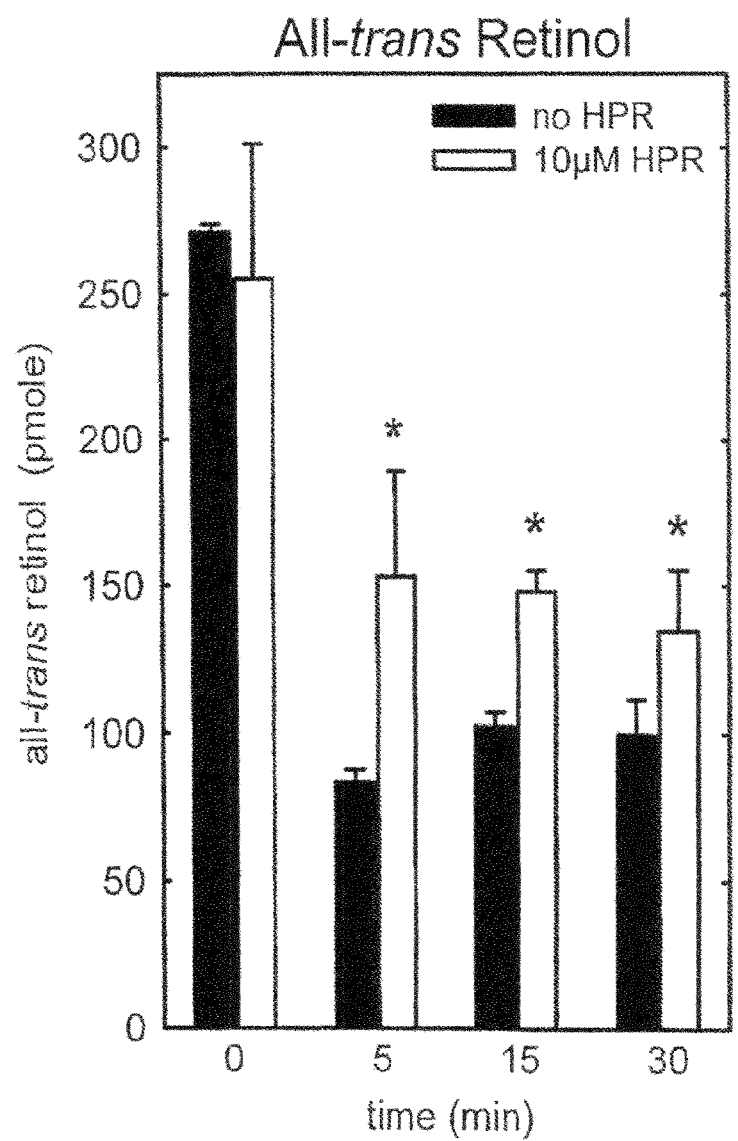
FIG. 6c illustrates the effect of HPR on all-trans retinol utilization using an in vitro biochemical assay.

Effects of Fenretinide on Vitamin A Homeostasis in the Retinal Pigment Epithelium We examined the effects on HPR on enzymes or proteins of the visual cycle using in vitro biochemical assays. Specifically, the utilization of exogenous all-trans retinol by membranes prepared from bovine RPE was studied. Representative data from our studies are shown in FIG. 5. Kinetic analyses of the inhibition data indicate that half-maximal inhibition of LRAT occurs at approximately 20 µM HPR. Steady-state levels of HPR in the RPE (determined from mice which have been given 20 mg/kg HPR, i.p., daily for 28 days) range from 5-10 µM. With this in mind, we examined the effects of 10 µM HPR on production of all-trans retinyl esters and 11-cis retinol in assays similar to those described above. In addition to decreases in all-trans retinol utilization (FIG. 6c) and all-trans retinyl ester synthesis (FIG. 6a), the data reveal a statistically significant inhibition of 11-cis retinol biosynthesis (p<0.05, indicated by asterisk), see FIG. 6b. In the presence of endogenous retinoids, utilization of exogenous all-trans retinol is extremely low and 11-cis retinol is produced solely from the endogenous all-trans retinyl esters.

In fact, when we perform our experiments in the presence of endogenous retinyl esters we do not observe an effect of HPR on 11-cis retinol production; however, inhibition of LRAT activity persists. Thus, the retinoic acids appear to affect at least two targets in the visual cycle. We have determined that HPR-induced reduction of 11-cis retinol biosynthesis occurs via LRAT inhibition and reduction in all-trans retinyl ester levels. In this situation, the isomerase enzyme is starved for substrate and 11-cis retinol production declines.

In the aggregate, it is clear from several studies that multiple targets exist for modulation of visual chromophore biosynthesis. Lowered visual chromophore then leads to a consequent decrease in all-trans retinal, the retinoid from which A2E is generated. Thus, treatment with HPR not only has systemic effects in lowering the amount of retinol delivered to the eye, but also intracellular effects on lowering steady state levels of all-trans retinal. The final outcome will be lowered A2E in the RPE, as evidenced above.

Thus, one of the outcomes of this study is that the treatment of the macular degenerations and dystrophies, including but not limited to controlling the formation of all-trans retinal, N-retinylidene-N-retinylethanolamine, N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, N-retinylidene-phosphatidylethanolamine, geographic atrophy, scotoma, lipofuscin and drusen in the eye of a mammal, may be effected by administration of an agent or agents that can both lower the levels of serum retinol and modulate at least one enzyme or protein in the visual cycle, including by way of example, LRAT activity. This dual action approach to the treatment of the macular or retinal dystrophies and degenerations, or the alleviation of symptoms associated with such diseases or conditions, is considered to be a generally applicable approach, and has been observed, as described herein, with fenretinide. In addition, (a) administration of an agent or agents that lower the levels of serum retinol in a patient without modulating at least one enzyme in the visual cycle or (b) administration of an agent or agents that modulate at least one enzyme in the visual cycle without lowering levels of serum retinol in a patient, by themselves, may also provide a treatment for such dystrophies and degenerations or the symptoms associated thereof. Assays, such as those described herein, may be used to select further agents possessing this dual action, including agents selected from compounds having the structure of Formula (I) as well as other agents. Putative lead compounds include other agents known or demonstrated to effect the serum level of retinol.

In order to determine the effects of HPR on visual cycle enzymes or proteins in vivo, the regeneration of rhodopsin from endogenous retinoid stores may be examined in HPR-treated mice and age/strain matched controls.

EXAMPLE 14

Combination Therapy Involving Fenretinide and a Statin

Mice and/or rats are tested in the manner described in Examples 6-9, but with an additional two arms. In one of the additional arms, groups of mice and/or rats are treated with a suitable statin such as: Lipitor® (Atorvastatin), Mevacor® (Lovastatin), Pravachol® (Pravastatin sodium), Zocor™ (Simvastatin), Leschol (fluvastatin sodium) and the like with optimal dosage based on weight. In the second additional arm, groups of mice and/or rats are treated with a combination of 20 mg/kg per day of fenretinide and increasing doses of the statin used in the previous step. Suggested human dosages of such statins are for example: Lipitor® (Atorvastatin) 10-80 mg/day, Mevacor® (Lovastatin) 10-80 mg/day, Pravachol® (Pravastatin sodium) 10-40 mg/day, Zocor™ (Simvastatin) 5-80 mg/day, Leschol (fluvastatin sodium) 20-80 mg/day. Dosage of statins for mice and/or rat subjects should be calculated based on weight. The benefits of the combination therapy are assayed as described in Examples 6-9.

EXAMPLE 15

Combination Therapy Involving Fenretinide, Vitamins and Minerals

Mice and/or rats are tested in the manner described in Example 14, but with selected vitamins and minerals. Administration of fenretinide in combination with vitamins and minerals can be either orally or parenterally administered at amounts effective to inhibit the development or reoccurrence of macular degeneration. Test dosages are initially in the range of about 20 mg/kg per day of fenretinide with 100-1000 mg vitamin C, 100-600 mg vitamin E, 10,000-40,000 IU vitamin A, 50-200 mg zinc and 1-5 mg copper for 15 to 20 weeks. The benefits of the combination therapy are assayed as described in Examples 6-9.

EXAMPLE 16

Fluorescence Quenching Study of Binding to Cellular Retinaldehyde Binding Protein (CRALBP)

Apo-CRALBP at 0.5 µM was incubated with 1 µM of 11-cis Retinal (11cRAL), all-trans retinal (atRAL) or N-4-hydroxyphenyl retinamide (HPR) in PBS at room temperature for 1 hour. As a control, same volume of DMSO was added to the Apo-CRABLP solution. The emission spectra were measured between 290 nm to 500 nm with excitation wavelength at 280 nm and 2 nm bandpass (See FIG. 7).

Compared to DMSO control, all three retinoids significantly quenched the fluorescence emission of CRALBP, with 11cRAL having the highest degree of quenching and HPR having the lowest, suggesting all three compounds bind to CRALBP. The fluorescence quenching likely results from the fluorescence resonance energy transfer between protein aromatic residues and bound retinoids

EXAMPLE 17

Size Exclusion Chromatography Study of Binding to CRALBP

Apo-CRALBP at 4 µM was incubated with 8 µM of 11cRAL, atRAL or HPR in PBS at room temperature for 1 hour. In control experiment, equivalent volume of DMSO was added to the CRALBP solution. 50 µl of each sample mixture was analyzed by BioRad Bio-Sil SEC125 Gel Filtration Column (300×7.8 mm).

In DMSO control (see FIG. 8a), apo-CRALBP eluted as multimers (elution peak at 8.1 ml); while ligand-bound holo-protein shifted to monomer form (elution peak at 9.4 ml). In the presence 11cRAL, a majority of the CRALBP is bound with ligand and displays strong 430 nm absorbance at the monomer elution position (see FIG. 8b). Less than half of the atRAL is bound to CRALBP (see FIG. 8c), and only small amount of HPR is bound to CRALBP, indicated by 350 nm absorbance peak (see FIG. 8d).

EXAMPLE 18

Fluorescence Quenching Study of MPR Binding to Retinol Binding Protein (RBP)

Apo-RBP at 0.5 µM was incubated with 0, 0.25, 0.5, 1 and 2 µM of MPR in PBS at room temperature for 1 hour, respectively. As controls, the same concentration of Apo-RBP was also incubated with 1 µM of HPR or 1 µM of atROL. All mixtures contained 0.2% Ethanol (v/v). The emission spectra were measured between 290 nm to 550 nm with excitation wavelength at 280 nm and 3 nm bandpass.

As shown in FIG. 9, MPR exhibited concentration-dependent quenching of RBP fluorescence, and the quenching saturated at 1 µM of MPR for 0.5 µM of RBP. Because the observed fluorescence quenching is likely due to fluorescence resonance energy transfer between protein aromatic residues and bound MPR molecule, MPR is proposed to bind to RBP. The degree of quenching by MPR is smaller than those by atROL and HPR, two other ligands that bind to RBP.

EXAMPLE 19

Size Exclusion Study of Transthyretin (TTR) Binding to RBP

Apo-RBP at 10 µM was incubated with 50 µM of MPR in PBS at room temperature for 1 hour. 10 µM of TTR was then added to the solution, and the mixture was incubated for another hour at room temperature. 50 µl of the sample mixtures with and without TTR addition were analyzed by Bio-Rad Bio-Sil SEC125 Gel Filtration Column (300×7.8 mm). In control experiments, atROL-RBP and atROL-RBP-TTR mixture were analyzed in the same manner.

As shown in FIG. 10a, the MPR-RBP sample exhibited an RBP elution peak (at 11 ml) with strong absorbance at 360 nm, indicating RBP binds to MPR; after incubation with TTR, this 360 nm absorbance stayed with the RBP elution peak, while TTR elution peak (at 8.6 ml) did not contain any apparent 360 nm absorbance (see FIG. 10b), indicating MPR-RBP did not bind to TTR. In atROL-RBP control experiment, RBP elution peak showed strong 330 nm absorbance (see FIG. 10c); after incubation with TTR, more than half of this 330 nm absorbance shifted to TTR elution peak (see FIG. 10d), indicating atROL-RBP binds to TTR. Thus, MPR inhibits the binding of TTR to RBP.

EXAMPLE 20

Analysis of Serum Retinol as a Function of HPR Concentration

ABCA4 null mutant mice were given the indicated dose of HPR in DMSO (i.p.) daily for 28 days (n=4 mice per dosage group). At the end of the study period, blood samples were taken and serum was prepared. Following acetonitrile precipitation of serum proteins, the concentrations of retinol and HPR were determined from the soluble phase by LC/MS (see FIG. 11). Identity of the eluted compounds was confirmed by UV-vis absorption spectroscopy and co-elution of sample peaks with authentic standards.

EXAMPLE 21

Figure 12:
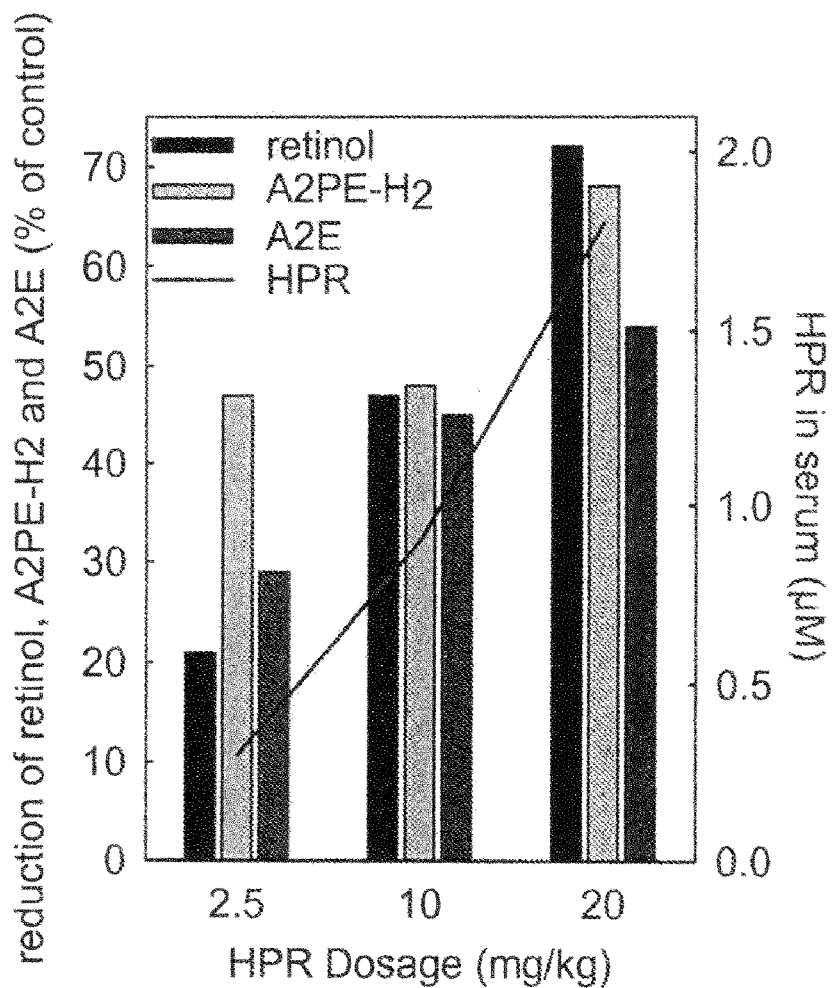
FIG. 12 illustrates a correlation plot relating fenretinide concentration to reductions in retinol, A2PE-$H_2$ and A2E in ABCA4 null mutant mice.

Correlation of HPR Concentration to Reductions in Retinol, $A2PE-H_2$ and A2E in ABCA4 Null Mutant Mice Group averages from the data shown in panels A - G of FIG. 18 in Example 25 (28 day time points) are plotted to illustrate the strong correlation between increases in serum HPR and decreases in serum retinol (see FIG. 12). Reductions in serum retinol are highly correlated with reductions in A2E and precursor compounds ($A2PE-H_2$). A pronounced reduction in $A2PE-H_2$ in the 2.5 mg/kg dosage group (~47%) is observed when the serum retinol reduction is only 20%. The reason for this disproportionate reduction is related to the inherently lower ocular retinoid content in this group of 2-month old animals compared to the other groups. It is likely that if these animals had been maintained on the 2.5 mg/kg dose for a more prolonged period, a greater reduction in A2E would also be realized.

EXAMPLE 22

Fluorescence Analysis of HPR Binding to Cellular Retinaldehyde Binding Protein (CRALBP)

Figure 13:
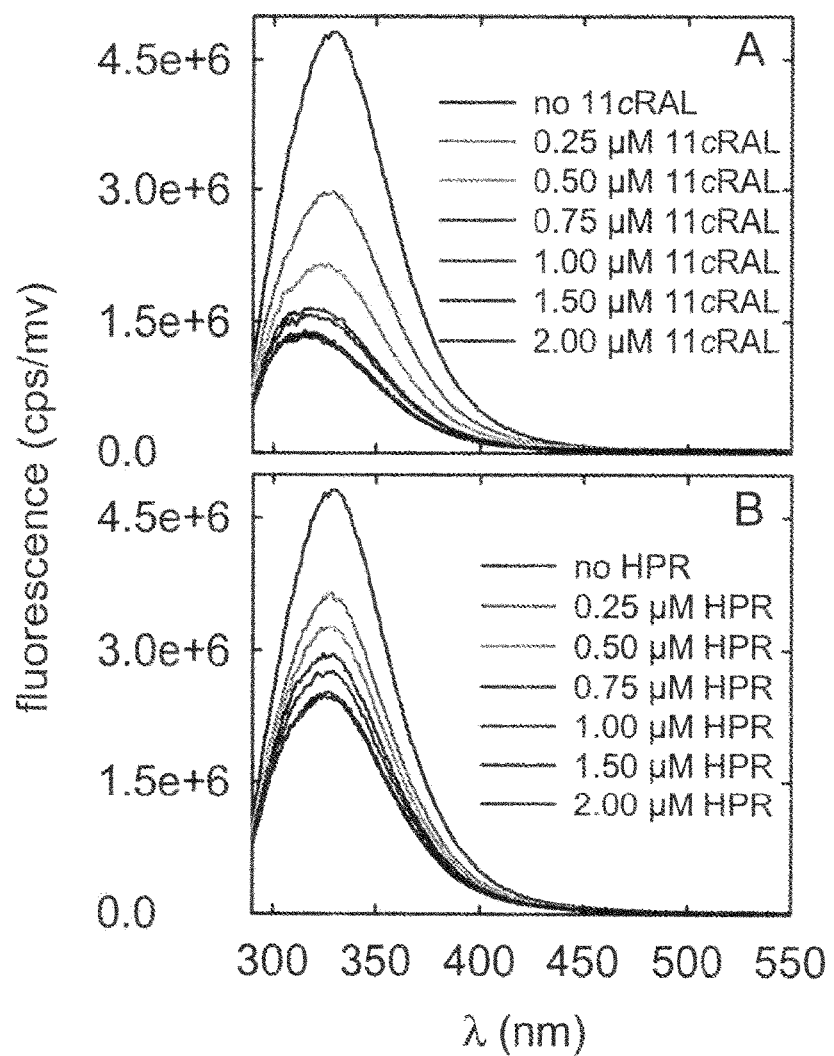
FIG. 13 illustrates (A) the quenching of CRALBP protein fluorescence with 11-cis-retinal (11 cRAL), and (B) the quenching of CRALBP protein fluorescence with fenretinide.

Quenching of CRALBP protein fluorescence with 11-cis retinal (11cRAL). The fluorescence emission of recombinant apo-CRALBP (0.5 µM) was measured using 280 nm excitation ("no 11cRAL"). Addition of the native ligand (11cRAL) quenched CRALBP protein fluorescence in a concentration dependent manner (see FIG. 13A). These data validate the technical approach used to confirm protein-ligand interaction.

Quenching of CRALBP protein fluorescence with HPR. The data shown were obtained using an experimental design identical to that described above. The fluorescence emission of recombinant apo-CRALBP was measured using 280 nm excitation ("no HPR"). Addition of HPR quenched CRALBP protein fluorescence in a concentration dependent manner similar to that observed with the native ligand (see FIG. 13b). These data strongly suggest that CRALBP binds HPR at physiological concentrations.

EXAMPLE 23

Spectroscopic Analysis of HPR Binding to Cellular Retinaldehyde Binding Protein (CRALBP)

Figure 14:
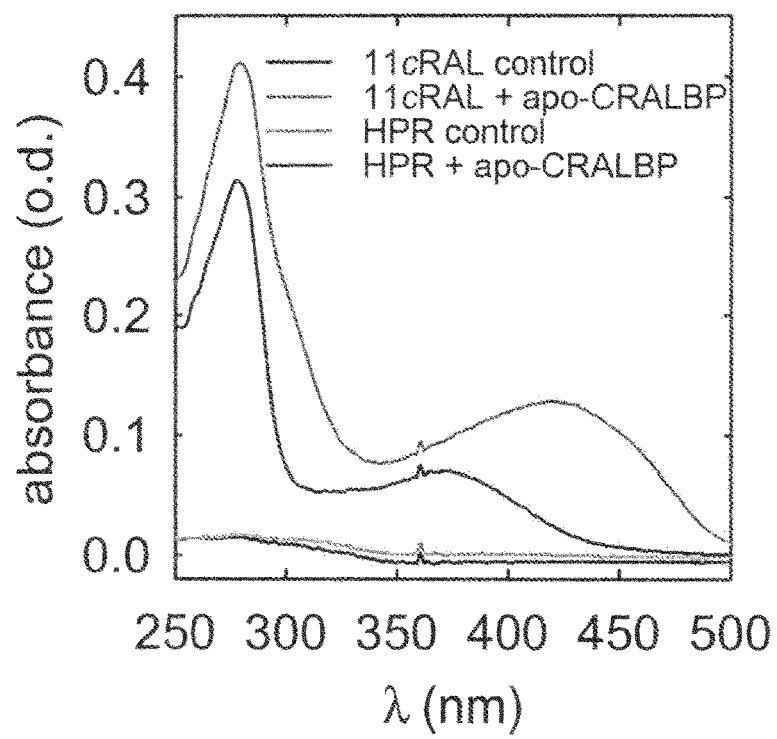
FIG. 14 illustrates a spectroscopic analysis of fenretinide binding to CRALBP.

In order to confirm data obtained during fluorescence analysis of HPR binding to CRALBP, a second analysis was performed using affinity chromatography and spectroscopic analysis. The recombinant apo-CRALBP was constructed with a histidine tag which is utilized to purify the protein on a Ni+ affinity column following expression cloning. Here, we utilized this feature of apo-CRALBP to specifically "trap" the protein and any protein-ligand species for spectroscopic analysis. Two binding mixtures were prepared containing apo-CRALBP (10 µM) and either 11cRAL (20 µM) or HPR (20 µM). In control experiments for the analysis of non-specific ligand binding onto the affinity matrix, we prepared two additional mixtures containing only 11cRAL (20 µM) or HPR (20µM) in binding buffer. The binding mixtures were passed through separate Ni+ affinity columns and the columns were washed extensively to elute unbound protein and ligand. Following the addition of elution buffer, the eluted fractions were analyzed by spectroscopy. Spectroscopic analysis of the 11cRAL+apo-CRALBP binding mixture (positive control) confirms that this technique is effective as the spectra are consistent with 11cRAL bound to CRALBP. Importantly, the data also show that HPR binds apo-CRALBP. If HPR did not bind apo-CRALBP only the protein absorbance (280 nm) would be observed in the eluted HPR+ apo-CRALBP sample. Instead, two absorption maxima are seen: one at 280 nm and a second at 360 nm, which is attributable to the absorption of HPR (see FIG. 14).

Figure 15:
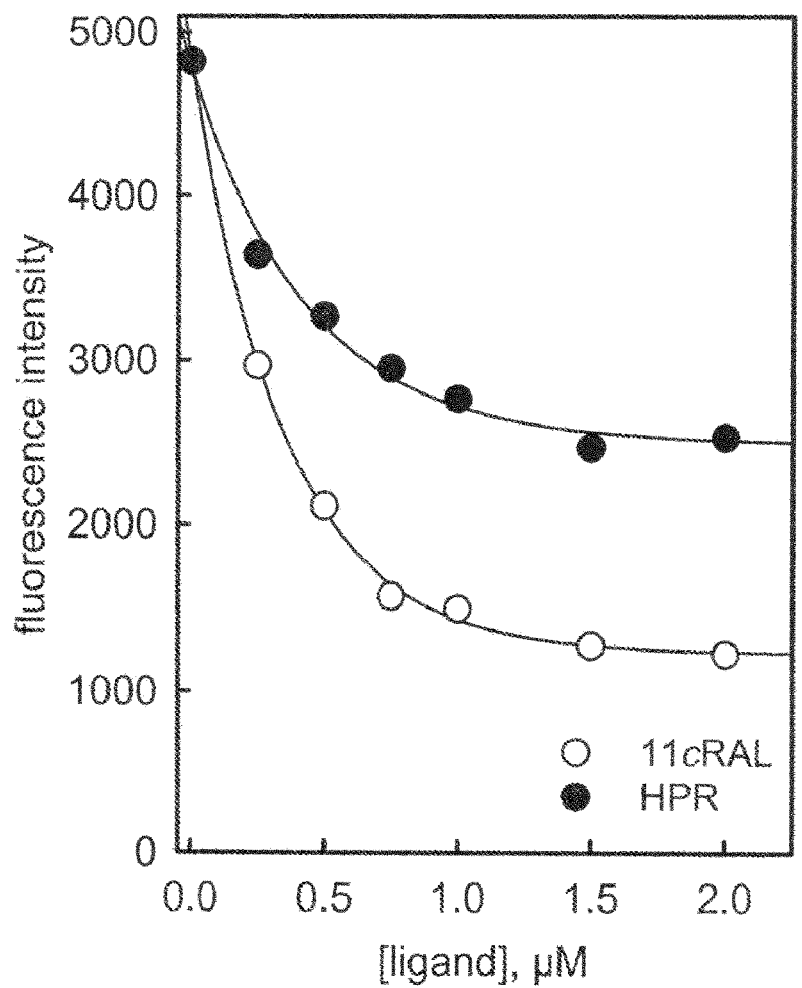
FIG. 15 illustrates the fluorescence quenching of apo-CRALBP as a function of the concentration of either 11 cRAL or fenretinide.

We performed an analysis of the dissociation constant ($K_D$) for 11 cRAL and HPR binding to apo-CRALBP (see FIG. 15). Transformation of the fluorescence quenching data revealed similar values (~30 nM) for each ligand. This calculation is based upon the ligand concentration necessary to fully quench the protein fluorescence. The data reveal that both 11cRAL and HPR quench apo-CRALBP fluorescence maximally at ~1.5 µM. Thus, although apo-CRALBP is described as an 11 cis-specific retinoid binding protein, it appears to bind HPR as well. The fact that concentrations of HPR in the RPE far exceed 30 nM during the animal trials (even at the lowest therapeutic dose of 2.5 mg/kg), suggests that some degree of HPR-mediated inhibition will be expected during biosynthesis of visual chromophore in the visual cycle.

EXAMPLE 24

Effects of HPR on Esterification of Vitamin A in the Retinal Pigment Epithelium (RPE)

Figure 16:
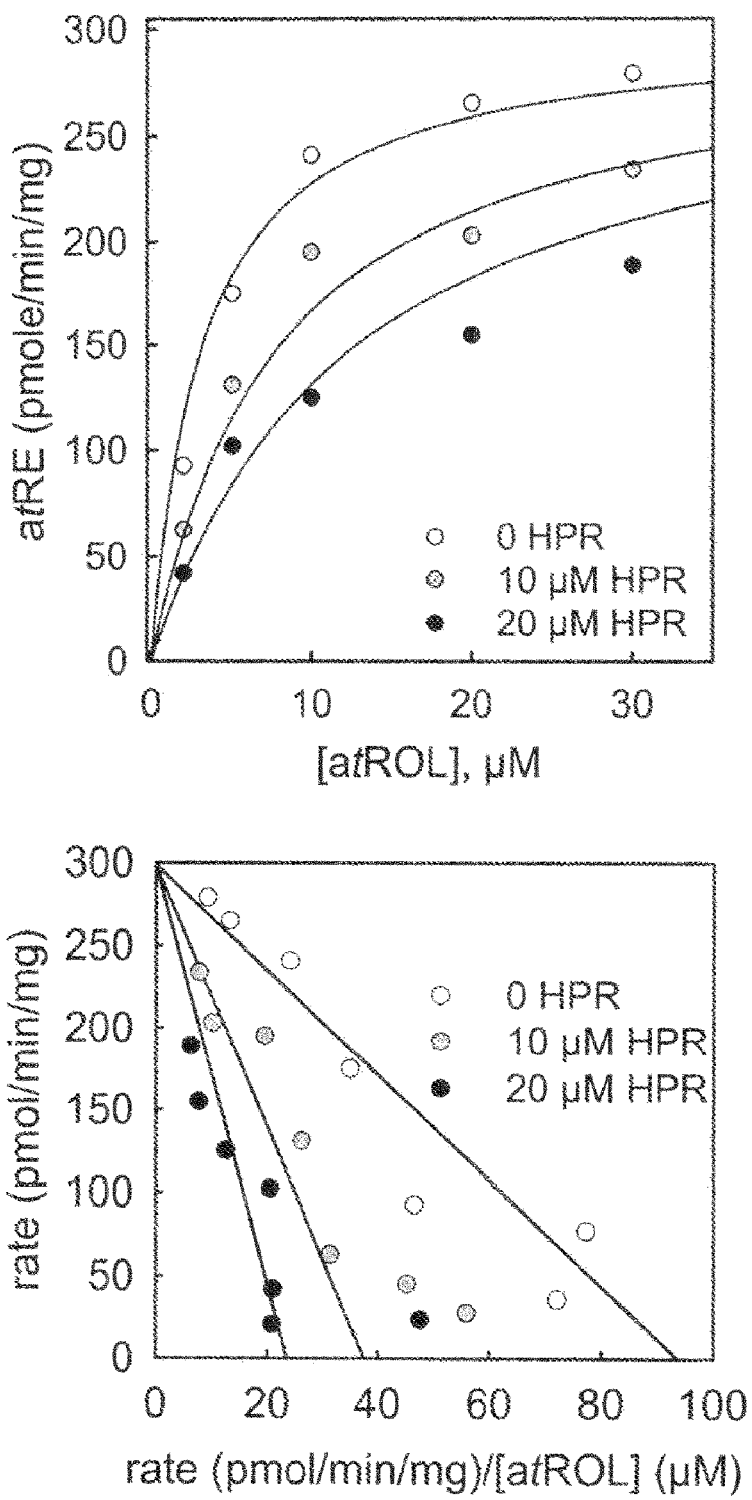
FIG. 16 illustrates the effect of fenretinide on the esterification of vitamin A in the retinal pigment epithelium.

A second target for HPR in the visual cycle was identified using in vitro biochemical assays. Lecithin retinol acyl transferase (LRAT) catalyzes the conversion of retinol into retinyl esters. LRAT is critical not only for retinol-retinyl ester homeostasis but also for generation of substrate for visual chromophore biosynthesis. The data shown in panel A of FIG. 16 illustrate the inhibitory effect of HPR on the rate of retinyl ester synthesis. In this assay, bovine RPE microsomes are used as an enzyme source and all-trans retinol (atROL) is the substrate. HPR decreases net retinyl ester synthesis in a concentration-dependent manner. A secondary transformation (Eadie-Hofstee) of the kinetic data in panel A reveal that the mode of inhibition is competitive (see FIG. 16, panel B). Therefore, HPR competes with atROL for binding sites on LRAT. The apparent inhibition constant ($K_i$) was determined to be ~6 µM. This means that at 6 µM HPR, the rate of retinyl ester synthesis would be decreased by 50%. In a separate study, we have determined that HPR concentrations in the RPE approach 10 µM with a 10 mg/kg dose of HPR.

In summary, it is clear from the data described in experiments 20-24 that the pronounced effect of HPR on reducing accumulation of A2E and its precursors during the animal trials was due to both systemic effects on lowering serum retinol and intracellular effects within the visual cycle.

EXAMPLE 25

Figure 17:
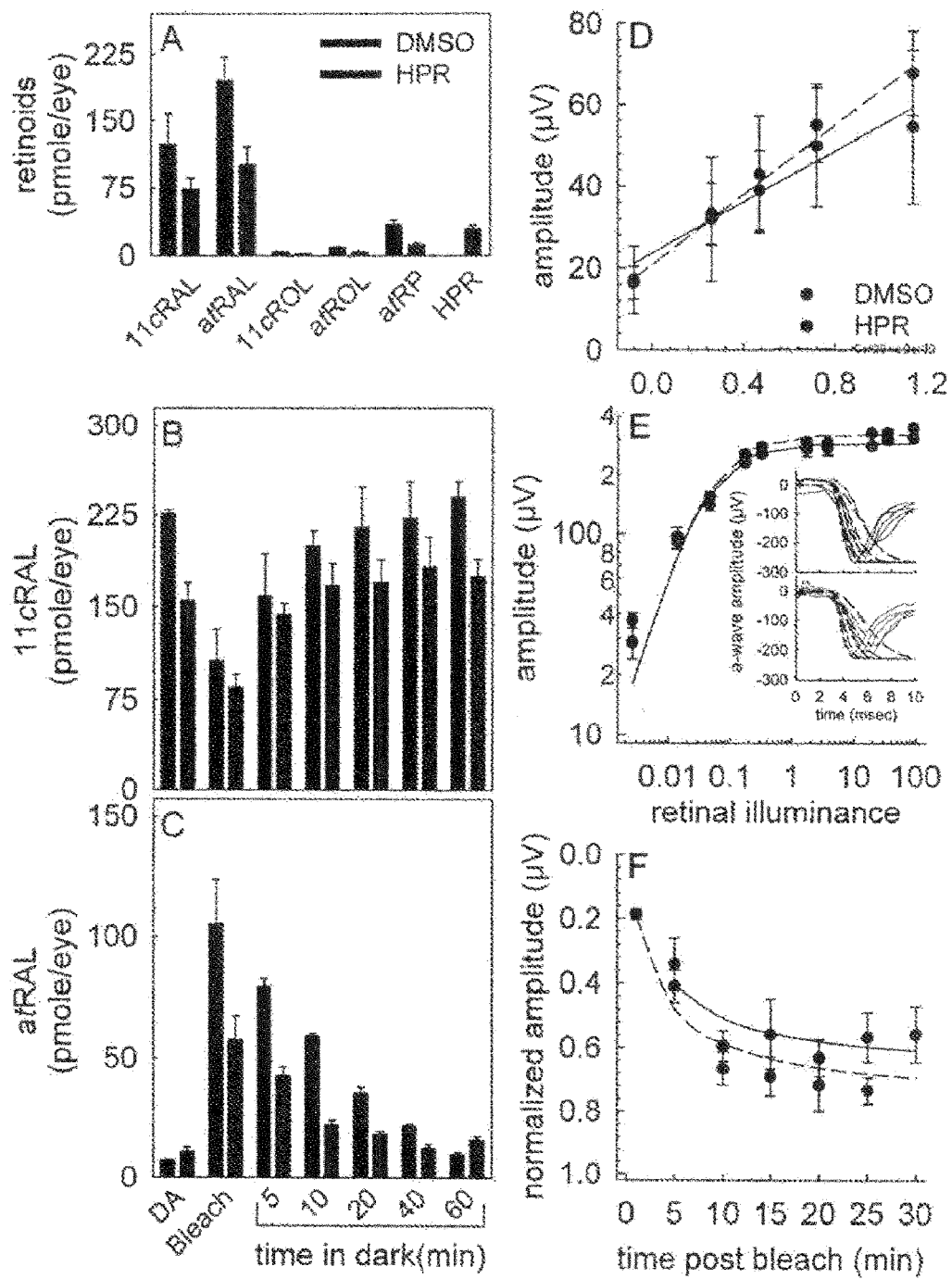
FIG. 17 illustrates retinoid composition in light adapted DMSO- and HPR-treated mice (panel A); the affect of HPR on the regeneration of visual chromophore (panel B); the effect of HPR on bleached chromophore recycling (panel C); and electrophysiological measurements of rod function (panel D), rod and cone function (panel E), and recovery from photobleaching (panel F).

Effects of HPR on Steady State Concentrations of Retinoids, A2E Fluorophores, and Retinal Physiology Analysis of retinoid composition in light adapted DMSO- and HPR-treated mice (FIG. 17, panel A) shows approximately 50% reduction of visual cycle retinoids as a result of HPR treatment (10 mg/kg daily for 28 days). Panels B and C of FIG. 17 show that HPR does not affect regeneration of visual chromophore in these mice (panel B is visual chromophore biosynthesis, panel C is bleached chromophore recycling). Panels D-F of FIG. 17 are electrophysiological measurements of rod function (panel D), rod and cone function (panel E) and recovery from photobleaching (panel F). The only notable difference is delayed dark adaptation in the HPR-treated mice (panel F).

ABCA4 null mutant mice were given the indicated dose of HPR in DMSO or DMSO alone daily for 28 days (n=16 mice per treatment group). At study onset, mice in the 2.5 mg/kg group were 2 months of age, mice in the other treatment groups were 3 months of age. At the indicated times representative mice were taken from each group (n=4) for analysis of A2E precursor compounds (see FIG. 18, A2PE-$H_2$, panels A, C and E) and A2E (see FIG. 18, panels B, D and F). Eyes were enucleated, hemisected and lipid soluble components were extracted from the posterior pole by chloroform/methanol-water phase partitioning. Sample extracts were analyzed by LC. Identity of the eluted compounds was confirmed by UV-vis absorption spectroscopy and co-elution of sample peaks with authentic standards. Note: limitations in appropriately age and strain-matched mice in the 10 mg/kg group prevented analysis at the 14-day interval. The data show dose-dependent reductions of A2PE-$H_2$ and A2E during the study period.

Figure 19:
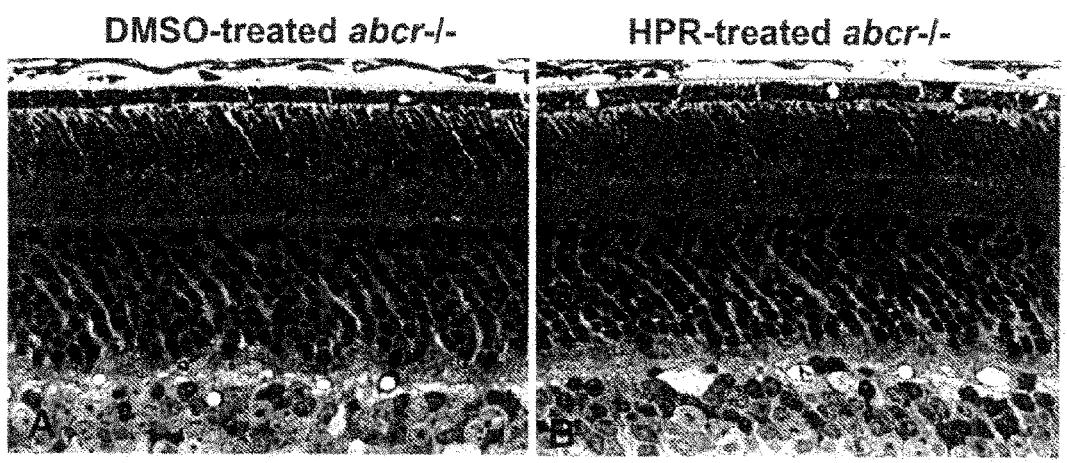
FIG. 19 illustrates light microscopy images of the retinas from DMSO- and HPR-treated animals.

Panels G-I in FIG. 18 show morphological/histological evidence that HPR significantly reduces lipofuscin autofluorescence in the RPE of abcr null mutant mice (Stargardt's animal model). Treatment conditions are as described above. The level of autofluorescence in the HPR-treated animal is comparable to that of an age-matched wild-type animal. FIG. 19 shows light microscopy images of the retinas from DMSO- and HPR-treated animals. No aberrant morphology or compromise of the integrity in retinal cytostructure was observed.

Accumulation of lipofuscin in the retinal pigment epithelium (RPE) is a common pathological feature observed in various degenerative diseases of the retina. A toxic vitamin A-based fluorophore (A2E) present within lipofuscin granules has been implicated in death of RPE and photoreceptor cells. In these experiments, we employed an animal model which manifests accelerated lipofuscin accumulation to evaluate the efficacy of a therapeutic approach based upon reduction of serum vitamin A (retinol). Fenretinide potently and reversibly reduces serum retinol. Administration of HPR to mice harboring a null mutation in the Stargardt's disease gene (ABCA4) produced profound reductions in serum retinol/retinol binding protein and arrested accumulation of A2E and lipofuscin autofluorescence in the RPE. Physiologically, HPR-induced reductions of visual chromophore were manifest as modest delays in dark adaptation; chromophore regeneration kinetics were normal. Importantly, specific intracellular effects of HPR on vitamin A esterification and chromophore mobilization were also identified. These findings demonstrate the vitamin A-dependent nature of A2E biosynthesis and validate a therapeutic approach which is readily transferable to human patients suffering from lipofuscin-based retinal diseases.

EXAMPLE 26

Benefits of HPR Therapy Persist During Drug Holiday

HPR (10 mg/kg in DMSO) was administered to ABCA4-/- mice daily for a period of 28 days. Control ABCA4-/- mice received only DMSO for the same period. Biochemical (HPLC) analysis of the A2E precursor (A2PE-$H_2$) and A2E following a 28-day treatment period revealed a reduction of these fluorophores in the eyes of HPR-treated mice (FIG. 18). Further analysis by fluorescence microscopy corroborated the biochemical data and revealed that lipofuscin autofluorescence levels of HPR-treated ABCA4-/- mice were comparable to levels observed in untreated wild type mice (FIG. 18). Histological examinations by light microscopy showed no alteration of retina cytostructure or morphology (FIG. 19). Importantly, the observed reductions in lipofuscin autofluorescence persist long after cessation of HPR therapy. HPR (10 mg/kg), or DMSO, administration was discontinued following 28 days of treatment and re-evaluated A2E and precursor levels after 2 weeks and after 4 weeks.

Figure 20:
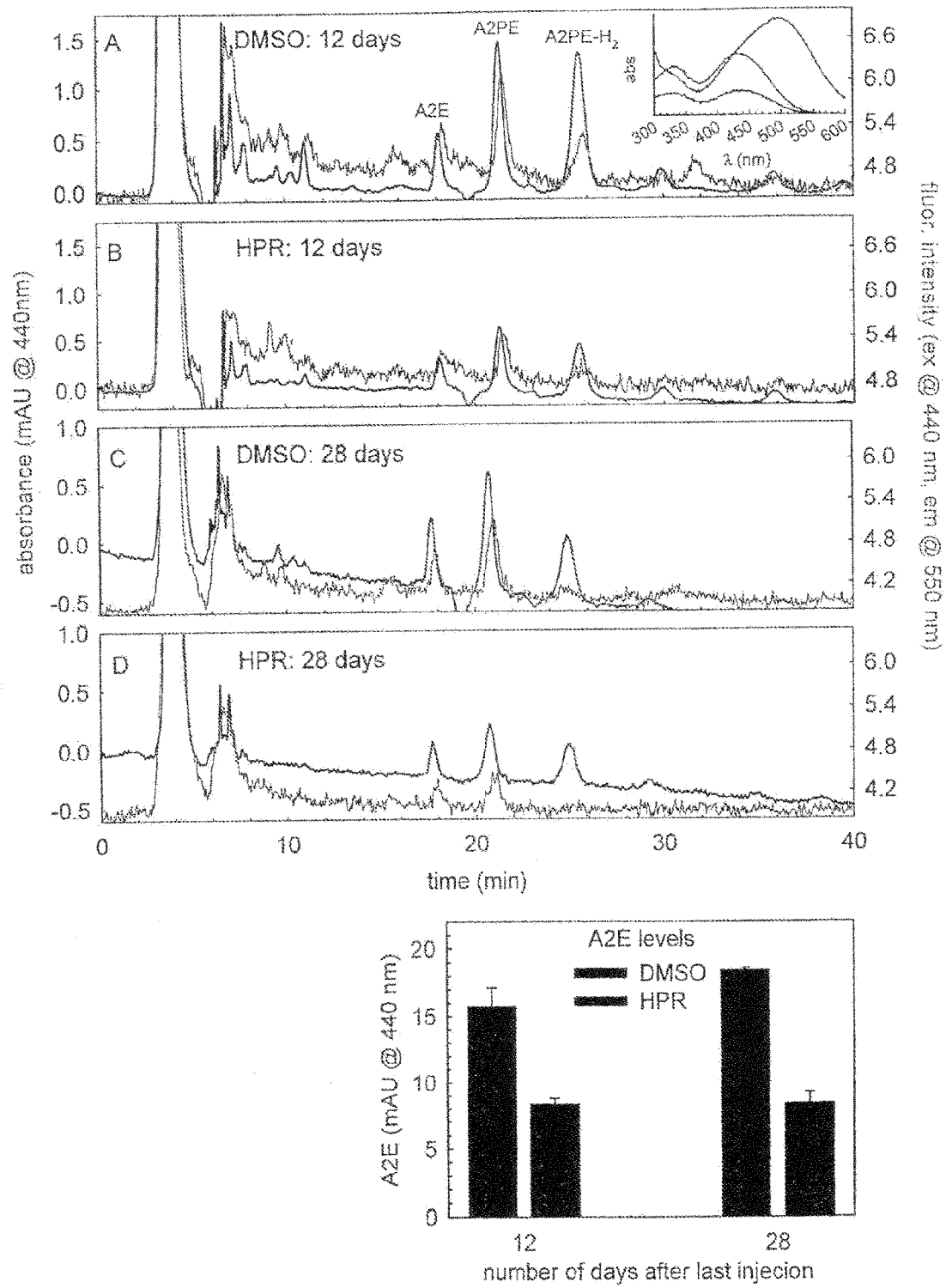
FIG. 20 illustrates absorbance and fluorescence chromatograms from eyecup extracts of control mice (panel A), and of mice previously maintained on HPR therapy (panel B) following a 12-day drug holiday; absorbance and fluorescence chromatograms from eyecup extracts of control mice (panel C), and of mice previously maintained on HPR therapy (panel D) following a 28-day drug holiday; the histogram presents the relative A2E levels for the mice described in panels A-D.

We examined eyecup extracts by HPLC and employed detection by absorbance and fluorimetry. Identity of the indicated peaks was confirmed by on-line spectral analysis and by co-elution with authentic standards. The data show that in animals that had been previously maintained on HPR therapy (FIG. 20, panel A), A2E and precursor (A2PE-$H_2$ and A2PE) levels remain significantly reduced relative to control mice (FIG. 20, panel B) even after 12 days without receiving a dose of HPR (i.e., a 12-day drug holiday). Similar results were observed in mice following a 28-day drug holiday: A2E and precursor (A2PE-$H_2$ and A2PE) levels remain significantly reduced relative to control mice (compare FIG. 20, panel C, treated mice, with FIG. 20, panel D, control mice). Further, the A2E and precursor (A2PE-$H_2$ and A2PE) levels after a 12- or 28-day drug holiday remained at or near the levels immediately following 28 days of treatment (i.e., ca. 50% reduction relative to control), although after the 28-day drug holiday, the amount of A2E and precursor (A2PE-$H_2$ and A2PE) had increased by a few percentage points relative to the 12-day drug holiday levels. Despite the persistent reduction in the levels of A2E and precursor (A2PE-$H_2$ and A2PE) in the eyes of animals on an HPR drug holiday, we were unable to detect either HPR or HPR metabolites (e.g., MPR) in the eyes of the animals on a 28-day drug holiday. The trace in FIG. 20, panels C and D, shows the intensity of autofluorescence associated with the indicated peaks. It is clear that peak fluorescence tracks with the abundance of A2E, A2PE and A2PE-$H_2$.

These data bear on toxicity during clinical trials by maintaining patients on a reduced HPR dose following proof of clinical efficacy at a higher dose. This analysis may obviate the need for additional corroboration by microscopy. To our knowledge this effect has not been observed with other methods for treating an ophthalmic condition or trait selected from the group consisting of Stargardt Disease, dry-form age-related macular degeneration, a lipofuscin-based retinal degeneration, photoreceptor degeneration, and geographic atrophy. Nor has this effect been observed with methods for reducing the formation of N-retinylidene-N-retinylethanolamine in an eye of a mammal, or methods for reducing the formation of lipofuscin in an eye of a mammal.

This effect cannot be attributed to long-term reductions in serum retinol as serum retinol had returned to baseline 48 hours following the last HPR dose. The fact that HPR accumulates within the RPE, and our identification of HPR-mediated inhibition of specific enzymes and proteins of the visual cycle, suggest that the latent, beneficial effects of HPR during the drug holiday are attributable to effects within the visual cycle. Furthermore, HPR reduces serum retinol levels, which leads to a reduction in the level of retinol in the eyes of treated animals. Once the level of retinol has been reduced in the eye, there is a time lag in the subsequent increase in retinol levels in the eye. Alone or in combination, the production of A2E, A2PE and A2PE-$H_2$ in the eye remains low despite the absence of HPR in the serum or the eye.

All of the methods disclosed and claimed herein can be made and executed without undue experimentation in light of the present disclosure. It will be apparent to those of skill in the art that variations may be applied to the methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

We claim:

1. A method for treating dry form age-related macular degeneration wherein there is geographic atrophy or photoreceptor degeneration in at least one eye comprising administering to a human in need thereof a pharmaceutical composition comprising 4-hydroxyphenylretinamide or 4-methoxyphenylretinamide, or a pharmaceutically acceptable salt thereof, whereby the method is for reducing the formation of or limiting the spread of geographic atrophy or photoreceptor degeneration in the at least one eye.

2. The method of claim 1, wherein the human is administered 4-methoxyphenylretinamide, or a pharmaceutically acceptable salt thereof.

3. The method of claim 1, wherein the human is administered 4-hydroxyphenylretinamide, or a pharmaceutically acceptable salt thereof.

4. The method of claim 1, wherein the pharmaceutical composition is in a form suitable for systemic administration.

5. The method of claim 1, wherein the pharmaceutical composition is in a form suitable for oral administration.

6. The method of claim 5, wherein the pharmaceutical composition is in the form of a tablet, powder, pill, dragee, capsule, liquid, gel, syrup, elixir, slurry, or suspension.

7. The method of claim 5, wherein the pharmaceutical composition further comprises: (a) lysophosphatidylcholine, monoglyceride and a fatty acid; (b) flour, a sweetener, and a humectant; or (c) corn oil and a non-ionic surfactant.

* * * * *